United States Patent
Marubashi et al.

(10) Patent No.: US 11,134,721 B2
(45) Date of Patent: Oct. 5, 2021

(54) POWER SUPPLY UNIT FOR AEROSOL INHALER

(71) Applicant: Japan Tobacco Inc., Tokyo (JP)

(72) Inventors: Keiji Marubashi, Tokyo (JP); Hajime Fujita, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 17/191,711

(22) Filed: Mar. 4, 2021

(65) Prior Publication Data

US 2021/0274852 A1 Sep. 9, 2021

(30) Foreign Application Priority Data

Mar. 5, 2020 (JP) .............................. JP2020-038193

(51) Int. Cl.
*H05B 1/02* (2006.01)
*A24F 40/57* (2020.01)
(Continued)

(52) U.S. Cl.
CPC .............. *A24F 40/57* (2020.01); *A24F 40/10* (2020.01); *A24F 40/20* (2020.01); *A24F 40/30* (2020.01);
(Continued)

(58) Field of Classification Search
CPC .......... A24F 40/57; A24F 40/10; A24F 40/20; A24F 40/30; A24F 40/51; H03B 3/0019;
(Continued)

(56) References Cited

U.S. PATENT DOCUMENTS 5,226,411 A * 7/1993 Levine .............. A61M 16/1085
128/203.26
10,869,508 B2 * 12/2020 Huang ................... H05B 6/108
(Continued)

FOREIGN PATENT DOCUMENTS

| CN | 208354611 U | 1/2019 |
| JP | 2017-501805 A | 1/2017 |
| WO | 2015/100361 A1 | 7/2015 |

OTHER PUBLICATIONS

Decision to Grant dated Jun. 2, 2020, received for JP Application 2020-038193, 5 pages including English Translation.
(Continued)

*Primary Examiner* — Mark H Paschall
(74) *Attorney, Agent, or Firm* — Xsensus LLP

(57) ABSTRACT

A power supply unit for an aerosol inhaler includes: a first series circuit; a second series circuit connected in parallel with the first series circuit; a first operational amplifier including a non-inversion input terminal connected to one of a first node and a second node, and an inversion input terminal connected to the other of the first node and the second node; and an adjustment circuit connected to the first operational amplifier and configured to prevent a differential input value of the first operational amplifier from being equal to a potential of a negative power supply terminal of the first operational amplifier or a minimum value acquirable by the first operational amplifier, in a state where a potential of the node connected to the non-inversion input terminal is less than a potential of the node connected to the inversion input terminal.

14 Claims, 32 Drawing Sheets

(51) Int. Cl.
*H02J 7/00* (2006.01)
*G05F 1/56* (2006.01)
*A24F 40/51* (2020.01)
*A24F 40/30* (2020.01)
*A24F 40/20* (2020.01)
*A61M 15/00* (2006.01)
*A24F 40/10* (2020.01)
*H05B 3/00* (2006.01)

(52) U.S. Cl.
CPC ........... *A24F 40/51* (2020.01); *A61M 15/009* (2013.01); *G05F 1/56* (2013.01); *H02J 7/0063* (2013.01); *H05B 3/0019* (2013.01); *A61M 2205/8206* (2013.01); *H05B 2203/035* (2013.01)

(58) Field of Classification Search
CPC .......... G01F 1/56; H02J 7/0063; H05B 3/099; H05B 2203/035

USPC ........ 219/481, 482, 483, 486, 501, 505, 497
See application file for complete search history.

(56) References Cited

U.S. PATENT DOCUMENTS

2018/0042306 A1\* 2/2018 Atkins ................. H05B 1/0297
2020/0128878 A1\* 4/2020 Stura ........................ H05B 6/06
2021/0106774 A1\* 4/2021 Ezeoke ................... A24F 40/65

OTHER PUBLICATIONS

Search report dated Aug. 6, 2021, in corresponding European patent Application No. 21160986.2, 4 pages.

\* cited by examiner

POWER SUPPLY UNIT FOR AEROSOL INHALER

CROSS-REFERENCE TO RELATED APPLICATION

This application is based on and claims priority under 35 USC 119 from Japanese Patent Application No. 2020-038193 filed on Mar. 5, 2020, the contents of which are incorporated herein by reference.

TECHNICAL FIELD

The present invention relates to a power supply unit for an aerosol inhaler.

BACKGROUND ART

JP-T-2017-501805 (hereinafter, referred to as Patent Literature 1) discloses a circuit that measures a resistance value of a heater in a device that generates an inhalable aerosol.

Since an aerosol inhaler is held by a user in a mouth thereof when used, temperature management of a heater used to generate an aerosol is important. Improvement of generation efficiency of the aerosol is also required.

Although the measurement of the resistance value of the heater is disclosed in Patent Literature 1, a specific configuration thereof is not disclosed.

An object of the present invention is to provide a power supply unit for an aerosol inhaler capable of detecting a temperature of a load used to generate an aerosol with high accuracy.

SUMMARY OF INVENTION

A first aspect of the present invention relates to a power supply unit for an aerosol inhaler. The aerosol inhaler includes a power supply configured to discharge electricity to a load which is configured to heat an aerosol generation source and has a correlation between temperature and electric resistance values. The power supply unit for the aerosol inhaler includes: a first element connected in series to the load and having a first electric resistance value; a second series circuit which includes a second element having a second electric resistance value, and a third element connected in series to the second element and having a third electric resistance value, the second series circuit being connected in parallel with a first series circuit including the load and the first element; a first operational amplifier which includes a non-inversion input terminal connected to one of a first connection node between the load and the first element and a second connection node between the second element and the third element, and an inversion input terminal connected to the other of the first connection node and the second connection node; and a potential adjustment circuit connected to the first operational amplifier and configured to prevent a differential input value of the first operational amplifier from being equal to a potential of a negative power supply terminal of the first operational amplifier or a minimum value acquirable by the first operational amplifier, in a state where a first potential of the first connection node or the second connection node which is connected to the non-inversion input terminal is less than a second potential of the first connection node or the second connection node which is connected to the inversion input terminal.

A second aspect of the present invention relates to a power supply unit for an aerosol inhaler. The aerosol inhaler includes a power supply configured to discharge electricity to a load which is configured to heat an aerosol generation source and has a correlation between temperature and electric resistance values. The power supply unit includes: a first element connected in series to the load and having a first electric resistance value; a second series circuit, which includes a second element having a second electric resistance value, and a third element connected in series to the second element and having a third electric resistance value, the second series circuit being connected in parallel with a first series circuit including the load and the first element; a first operational amplifier, which includes a non-inversion input terminal connected to one of a first connection node between the load and the first element and a second connection node between the second element and the third element, and an inversion input terminal connected indirectly to the other of the first connection node and the second connection node; and a second operational amplifier, which includes: a non-inversion input terminal which is connected to the first connection node or the second connection node connected indirectly to the inversion input terminal; an inversion input terminal where a positive predetermined potential is input; and an output terminal connected to the inversion input terminal of the first operational amplifier.

According to the present invention, the temperature of the load used to generate the aerosol can be detected with high accuracy.

BRIEF DESCRIPTION OF DRAWINGS

Exemplary embodiments of the present invention will be described in detail based on the following figures, wherein.

DESCRIPTION OF EMBODIMENTS

Figure 1:
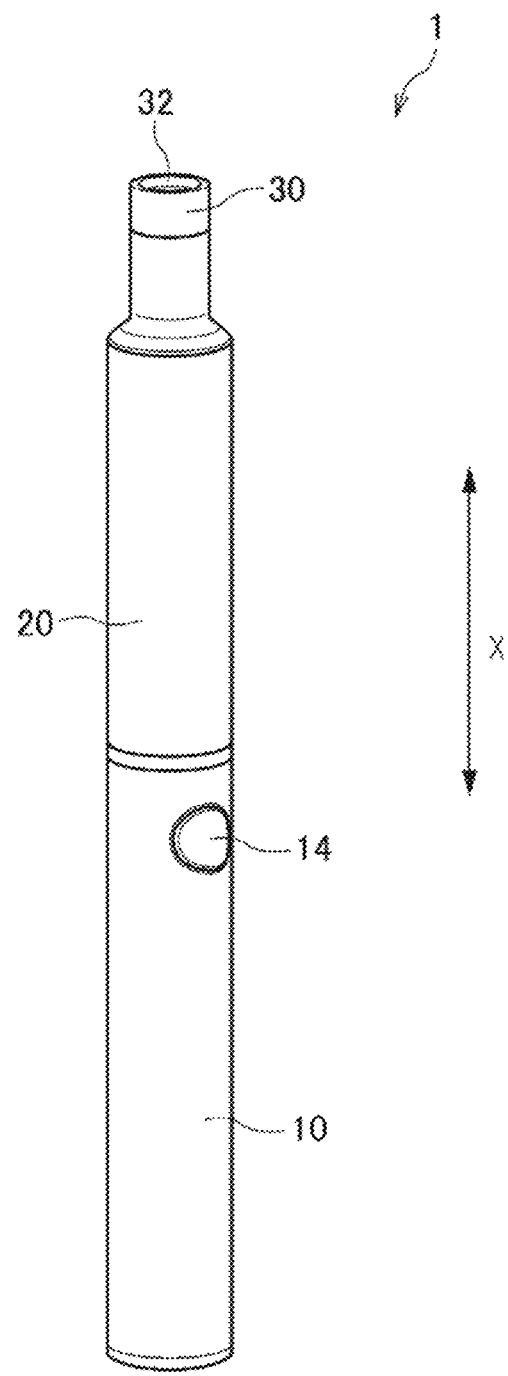
FIG. 1 is a perspective view of an aerosol inhaler equipped with a power supply unit of one embodiment of the present invention.

Hereinafter, a power supply unit for an aerosol inhaler according to an embodiment of the present invention will be described. First, the aerosol inhaler equipped with the power supply unit will be described with reference to FIGS. 1 and 2.

(Aerosol Inhaler)

An aerosol inhaler 1 is an instrument for inhaling a perfumed aerosol without burning, and has a rod shape extending along a predetermined direction (hereinafter referred to as a longitudinal direction X). In the aerosol inhaler 1, a power supply unit 10, a first cartridge 20, and a second cartridge 30 are provided in such an order along the longitudinal direction X. The first cartridge 20 can be attached to and detached from the power supply unit 10. The second cartridge 30 can be attached to and detached from the first cartridge 20. In other words, the first cartridge 20 and the second cartridge 30 are replaceable.

(Power Supply Unit)

As shown in FIGS. 3, 4, 5 and 6, the power supply unit 10 of the present embodiment accommodates, inside a cylindrical power supply unit case 11, a power supply 12, a charging IC 55A, a micro controller unit (MCU) 50, and various sensors, such as an intake sensor 15. The power supply 12 is a rechargeable secondary battery, an electric double layer capacitor or the like, and is preferably a lithium ion secondary battery. An electrolyte of the power supply 12 may include one of a gel electrolyte, an electrolytic solution, a solid electrolyte, an ionic liquid, or a combination thereof.

Figure 4:
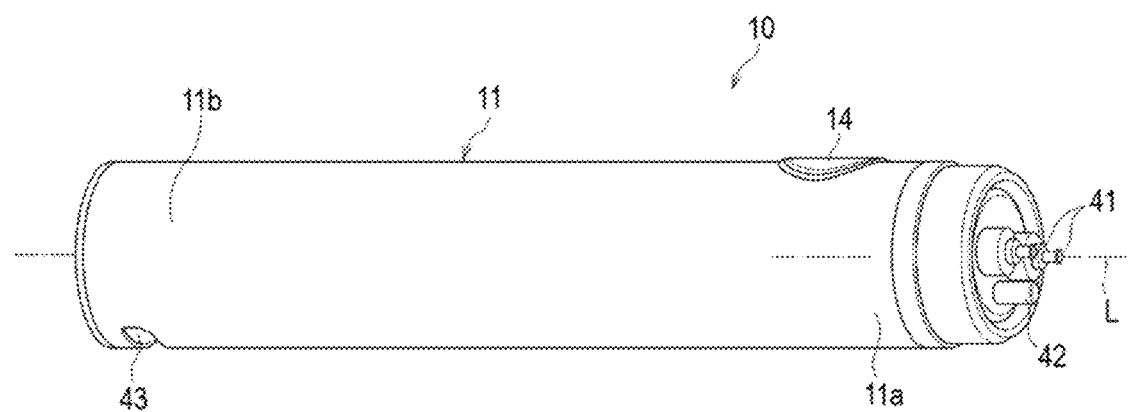
FIG. 4 is a perspective view of the power supply unit of the aerosol inhaler shown in FIG. 1.

As shown in FIG. 4, a discharge terminal 41 is provided on a top portion 11a located on one end side (side of the first cartridge 20) of the power supply unit case 11 in the longitudinal direction X. The discharge terminal 41 protrudes from an upper surface of the top portion 11a toward the first cartridge 20, and is configured to be electrically connectable to a load 21 of the first cartridge 20.

An air supply unit 42 configured to supply air to the load 21 of the first cartridge 20 is provided on the upper surface of the top portion 11a in the vicinity of the discharge terminal 41.

A charge terminal 43 that is electrically connectable to an external power supply (not shown) capable of charging the power supply 12 is provided on a bottom portion 11b located on the other end side (side opposite to the first cartridge 20) of the power supply unit case 11 in the longitudinal direction X. The charge terminal 43 is provided on a side surface of the bottom portion 11b, and is connectable with at least one of a USB (Universal Serial Bus) terminal, a micro USB terminal, and a Lightning (registered trademark) terminal, for example.

The charge terminal 43 may be a power receiving unit capable of receiving power transmitted from the external power supply in a non-contact manner. In such a case, the charge terminal 43 (power receiving unit) may include a power receiving coil. A method for transmitting power in a non-contact manner (wireless power transfer) may be an electromagnetic induction type or a magnetic resonance type. The charge terminal 43 may also be a power receiving unit capable of receiving power transmitted from the external power supply in a contactless manner. As another example, the charge terminal 43 may be connectable with at least one of a USB terminal, a micro USB terminal, and a Lightning terminal, and include the power receiving unit described above.

Figure 3:
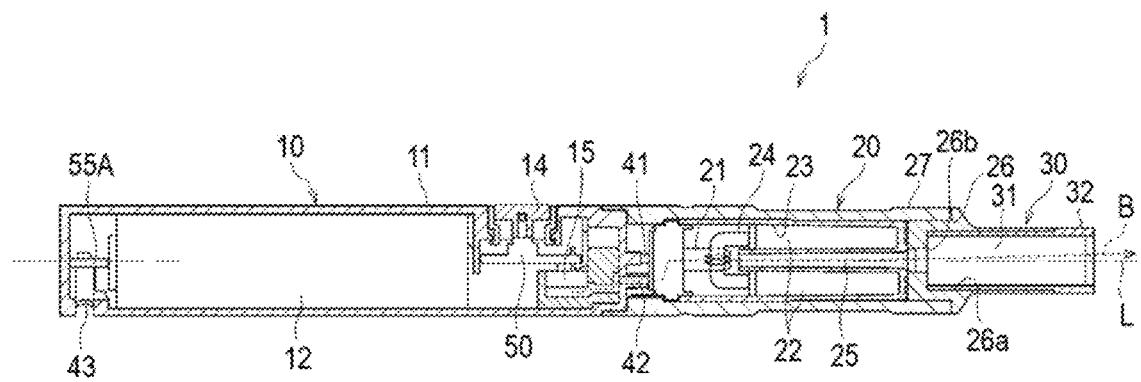
FIG. 3 is a cross-sectional view of the aerosol inhaler shown in FIG. 1.

An operation portion 14 that can be operated by a user is provided on the power supply unit case 11 so as to face a side opposite to the charge terminal 43 on a side surface of the top unit 11a. More specifically, the operation portion 14 and the charge terminal 43 have a point-symmetric relationship with respect to an intersection of a straight line connecting the operation portion 14 and the charge terminal 43 and a center line of the power supply unit 10 in the longitudinal direction X. The operation portion 14 includes a button type switch, a touch panel, or the like. As shown in FIG. 3, the intake sensor 15 that detects a puff operation is provided in the vicinity of the operation portion 14.

The charging IC 55A is arranged in proximity to the charge terminal 43, and controls charging of power input from the charge terminal 43 to the power supply 12. The charging IC 55A may also be arranged in the vicinity of the MCU 50.

Figure 5:
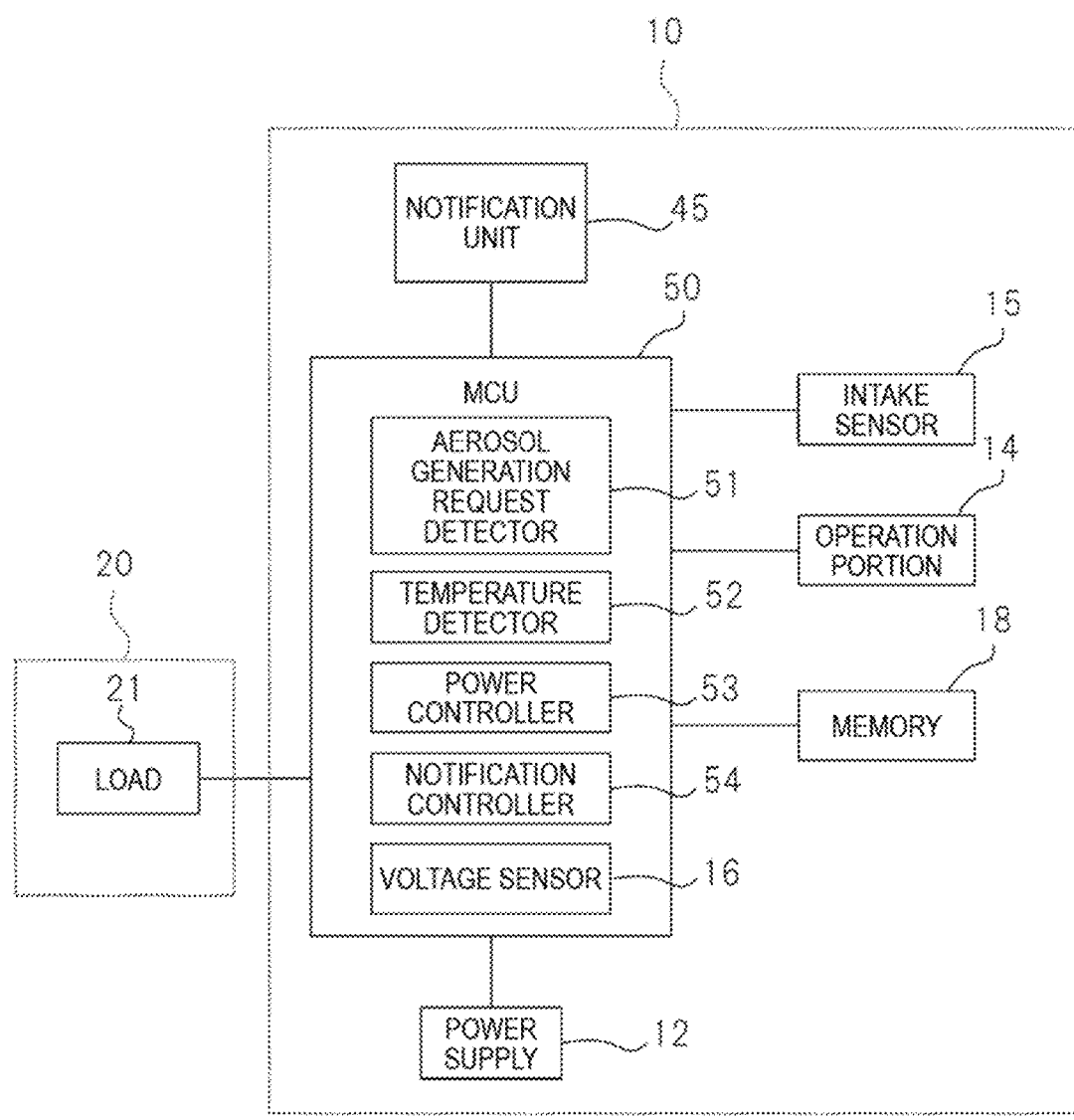
FIG. 5 is a block diagram showing a configuration of a main part the power supply unit of the aerosol inhaler shown in FIG. 1.

As shown in FIG. 5, the MCU 50 is connected to various sensor devices (such as the intake sensor 15 that detects the puff (intake) operation), the operation portion 14, a notification unit 45 to be described below, and a memory 18 that stores the number of times of puff operations, a time of energization to the load 21 or the like so as to perform various types of control of the aerosol inhaler 1. Specifically, the MCU 50 mainly includes a processor 55 (see FIG. 7), which will be described below, and further includes storage media, such as a random access memory (RAM) necessary for operations of the processor 55 and a read only memory (ROM) that stores various types of information. More specifically, the processor in the present specification is an electric circuit in which circuit elements such as semiconductor elements are combined.

The MCU 50 includes a voltage sensor 16 that measures a power supply voltage of the power supply 12. The voltage sensor 16 may include a first operational amplifier 56 and an ADC 57, which will be described later below. In the MCU 50, an output signal of the voltage sensor 16 is input to the processor 55. Instead of the configuration of the present embodiment, the voltage sensor 16 may also be provided outside the MCU 50 and connected to the MCU 50.

The power supply unit case 11 is provided with an air intake port (not shown) configured therein to take in outside air. The air intake port may be provided around the operation portion 14, or may be provided around the charge terminal 43.

(First Cartridge)

As shown in FIG. 3, inside a cylindrical cartridge case 27, the first cartridge 20 includes a reservoir 23 that stores an aerosol source 22, the electric load 21 that atomizes the aerosol source 22, a wick 24 that draws the aerosol source from the reservoir 23 to the load 21, an aerosol flow path 25 through which aerosol generated by the atomization of the aerosol source 22 flows toward the second cartridge 30, and an end cap 26 that accommodates a part of the second cartridge 30.

The reservoir 23 is partitioned to surround a periphery of the aerosol flow path 25, and stores the aerosol source 22. A porous body, such as a resin web or cotton, may be accommodated in the reservoir 23, and the aerosol source 22 may be impregnated in the porous body. The reservoir 23 may only store the aerosol source 22 without accommodating the porous body such as the resin web or cotton. The aerosol source 22 includes a liquid such as glycerin, propylene glycol or water.

The wick 24 is a liquid holding member that draws the aerosol source 22 from the reservoir 23 to the load 21 by utilizing a capillary phenomenon. The wick 24 is made of, for example, glass fiber or porous ceramic.

The load 21 atomizes the aerosol source 22 by heating the aerosol source 22 by power supplied from the power supply 12 via the discharge terminal 41 without burning. The load 21 is formed of an electric heating wire (coil) wound at a predetermined pitch.

The load 21 may be any element that can perform atomization by heating the aerosol source 22 to generate the aerosol. The load 21 is, for example, a heat generating element. Examples of the heat generating element include a heat generating resistor, a ceramic heater, an induction heating type heater, and the like. Hereinafter, an electric resistance value of the load 21 will be referred to as an electric resistance value $R_{HTR}$.

A load whose temperature and electric resistance values are correlated is used as the load 21. For example, a load having a positive temperature coefficient (PTC) characteristic, which causes the electric resistance value to increase as the temperature increases, is used as the load 21. The PTC characteristic is also referred to as a positive resistance temperature coefficient characteristic.

The aerosol flow path 25 is downstream of the load 21 and is provided on a center line L of the power supply unit 10. The end cap 26 includes: a cartridge accommodating portion 26a that accommodates a part of the second cartridge 30, and a communication path 26b that connects the aerosol flow path 25 and the cartridge accommodating portion 26a.

(Second Cartridge)

The second cartridge 30 stores a perfume source 31. The second cartridge 30 is detachably accommodated in the cartridge accommodating portion 26a provided in the end cap 26 of the first cartridge 20. An end portion, which is located on a side opposite to the side of the first cartridge 20, of the second cartridge 30 serves as a user inhale port 32. The inhale port 32 is not limited to be formed integrally with the second cartridge 30, and may also be detachable from the second cartridge 30. By forming the inhale port 32 separately from the power supply unit 10 and the first cartridge 20 in this way, the inhale port 32 can be kept hygienic.

The aerosol generated by atomizing the aerosol source 22 by the load 21 is passed through the perfume source 31 in the second cartridge 30, so that the aerosol is imparted with a perfume. Chopped tobacco or a molded body obtained by molding a tobacco raw material into particles can be used as a raw material piece that forms the perfume source 31. The perfume source 31 may also be formed of a plant other than tobacco (for example, mint, Chinese herb, or herb). The perfume source 31 may also be provided with a fragrance such as menthol.

According to the aerosol inhaler 1 of the present embodiment, a perfumed aerosol can be generated by the aerosol source 22, the perfume source 31, and the load 21. That is, the aerosol source 22 and the perfume source 31 constitute an aerosol generation source that generates the aerosol.

The aerosol generation source of the aerosol inhaler 1 is a portion that is replaced and used by the user. As this portion, for example, one first cartridge 20 and one or a plurality of (for example, five) second cartridges 30 are provided to the user as a set.

In addition to a configuration in which the aerosol source 22 and the perfume source 31 are separated from each other, a configuration in which the aerosol source 22 and the perfume source 31 are integrally formed, a configuration in which the perfume source 31 is omitted and substances that can be included in the perfume source 31 are added to the aerosol source 22, or a configuration in which a medicine or the like is added to the aerosol source 22 instead of the perfume source 31 may also be employed as the configuration of the aerosol generation source used in the aerosol inhaler 1.

In a case where the aerosol inhaler 1 includes the aerosol generation source in which the aerosol source 22 and the perfume source 31 are integrally formed, for example, one or a plurality of (for example, 20) aerosol generation sources are provided as a set to the user.

In a case where the aerosol inhaler 1 only includes the aerosol source 22 as the aerosol generation source, for example, one or a plurality of (for example, 20) aerosol generation sources are provided as a set to the user.

According to the aerosol inhaler 1 configured in this way, as indicated by arrow B in FIG. 3, air flowing in from the intake port (not shown) provided in the power supply unit case 11 passes through the vicinity of the load 21 of the first cartridge 20 from the air supply unit 42. The load 21 atomizes the aerosol source 22 drawn by the wick 24 from the reservoir 23. The aerosol generated by atomization flows through the aerosol flow path 25 together with the air flowing in from the intake port, and is supplied to the second cartridge 30 via the communication path 26b. The aerosol supplied to the second cartridge 30 passes through the perfume source 31 so as to be perfumed, and is then supplied to the inhale port 32.

The aerosol inhaler 1 is provided with the notification unit 45 that notifies various types of information (see FIG. 5). The notification unit 45 may include a light emitting element, a vibrating element, or a sound output element. The notification unit 45 may also be a combination of two or more elements among the light emitting element, the vibrating element, and the sound output element. The notification unit 45 may be provided in any one of the power supply unit 10, the first cartridge 20, and the second cartridge 30, and is preferably provided in the power supply unit 10. For example, a configuration in which a periphery of the operation portion 14 is translucent and emits light by a light emitting element such as an LED is employed.

(First Embodiment of Electric Circuit)

Figure 2:
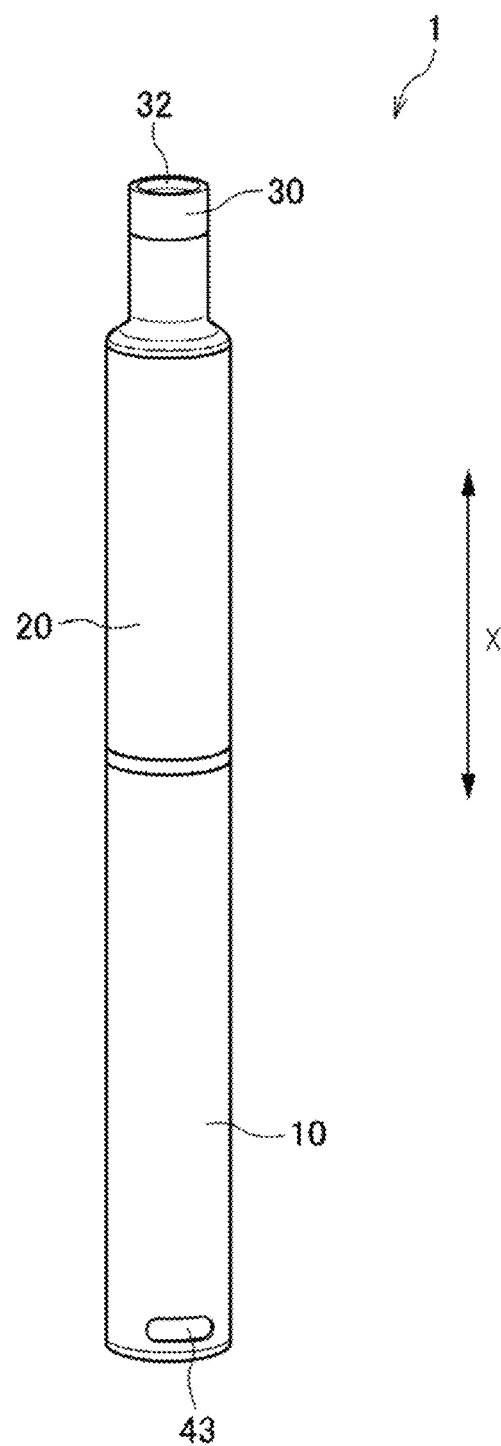
FIG. 2 is another perspective view of the aerosol inhaler shown in FIG. 1.
Figure 6:
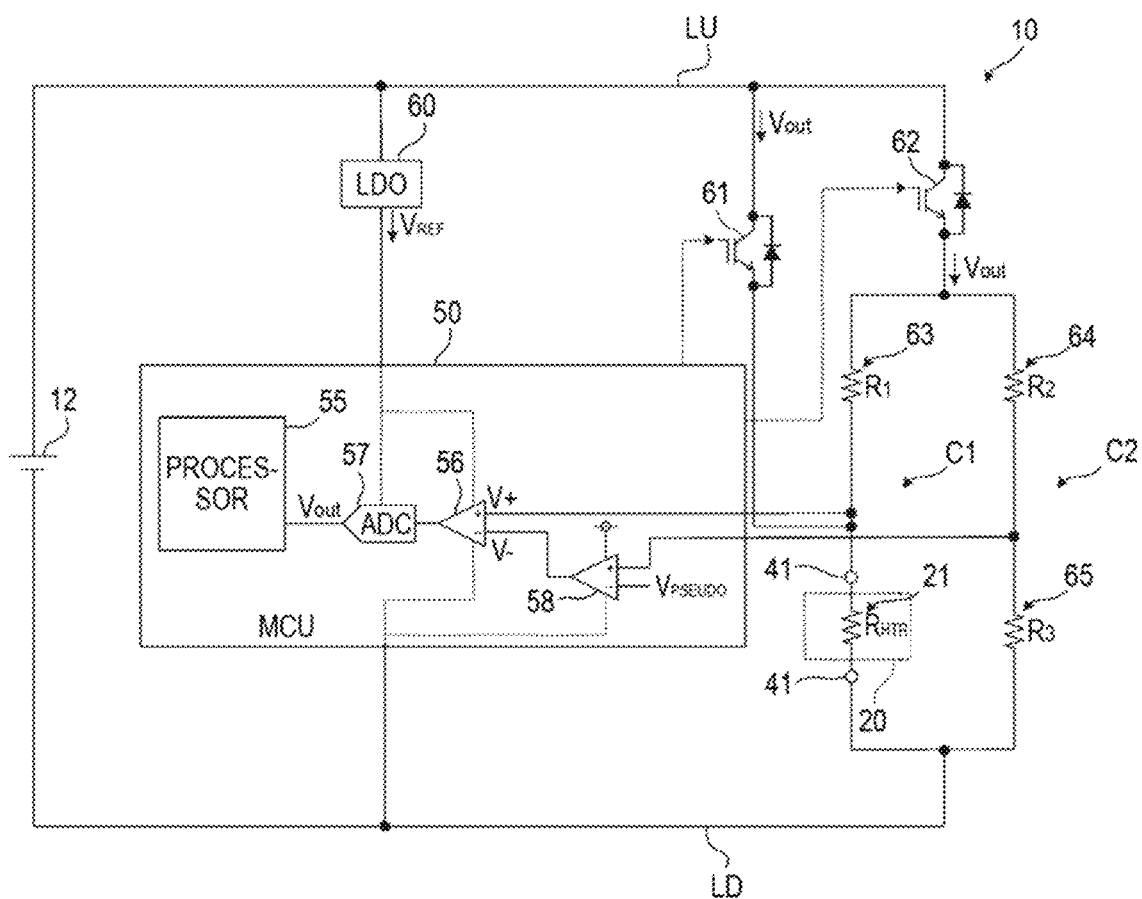
FIG. 6 is a schematic diagram showing a first embodiment of a circuit configuration of the power supply unit of the aerosol inhaler shown in FIG. 1.

FIG. 6 is a schematic diagram showing a first embodiment of a circuit configuration of the power supply unit of the aerosol inhaler shown in FIG. 1. As shown in FIG. 6, the power supply unit 10 includes, as main circuit configurations, the power supply 12, the discharge terminal 41 where the first cartridge 20 including the load 21 is detachably attached, the MCU 50, a low drop out (LDO) regulator 60, a switch 62, a first element 63 having a first electric resistance value $R_1$, a second element 64 having a second electric resistance value $R_2$ and a third element 65 having a third electric resistance value $R_3$.

Each of the first element 63, the second element 64, and the third element 65 is an element having an electric resistance value, for example, a resistor, a diode, or a transistor. In the example of FIG. 6, the first element 63, the second element 64, and the third element 65 are resistors.

The switch 62 is a switching element such as a transistor that switches between blocking and conduction of a wiring path. In the example of FIG. 6, the switch 62 is a normally-off type insulated gate bipolar transistor (IGBT) that is turned on (conducted) upon receiving a high-level turn-on command signal supplied from the MCU 50 and is turned off (blocked) upon receiving a low-level turn-off command signal supplied from the MCU 50. The switch 61 is a normally-off type IGBT, like the switch 62. A field effect transistor (FET) may also be used as the switch 61 or the switch 62 instead of the IGBT.

The LDO regulator 60 and the MCU 50 are connected in series to the power supply 12. The LDO regulator 60 steps down and outputs a voltage from the power supply 12. An output voltage of the LDO regulator 60 (hereinafter, referred to as a reference voltage $V_{REF}$) is supplied to the MCU 50 as an operation voltage of the MCU 50. Among a main positive bus LU and a main negative bus LD, the main positive bus LU is a line on a high potential side, and the main negative bus line LD is a line on a low potential side. In the example of FIG. 6, the main positive bus LU is a line having a highest potential in the electric circuit of the power supply unit 10. The main negative bus LD is a line having a lower potential than the main positive bus LU. In the example of FIG. 6, the main negative bus LD is a line having a lowest potential (specifically, 0 V) in the electric circuit of the power supply unit 10.

The MCU 50 is connected to the LDO regulator 60 and the main negative bus LD that is connected to a negative electrode of the power supply 12. The MCU 50 is also connected to the switch 61 and the switch 62, and controls on and off of the switch 61 and the switch 62. Hereinafter, a voltage applied to a bridge circuit constituted by a first series circuit C1 and a second series circuit C2 in a state where the switch 61 is turned off while the switch 62 is turned on and a voltage applied to a connection node between the first element 63 and the load 21 in a state where the switch 61 is turned on while the switch 62 is turned off will be referred to as a voltage $V_{OUT}$, respectively. The voltage $V_{OUT}$ may be the same as the reference voltage $V_{REF}$.

In a state where the first cartridge 20 is attached to the power supply unit 10, the first element 63 and the load 21 are connected in series to form the first series circuit C1. The second element 64 and the third element 65 are connected in series to form the second series circuit C2.

The first series circuit C1 and the second series circuit C2 are connected in parallel between the main positive bus LU and the main negative bus LD. Specifically, a collector of the switch 62 is connected to the main positive bus LU, and the first element 63 and the second element 64 are connected in parallel to an emitter of the switch 62. The load 21 and the third element 65 are connected in parallel to the main negative bus LD. The load 21 is connected to the first element 63, and the third element 65 is connected to the second element 64.

The first series circuit C1 is connected to the MCU 50. Specifically, in the first series circuit C1, a first connection node between the first element 63 and the load 21 is connected to the MCU 50. An emitter of the switch 61 is connected between the first connection node and the load 21 in the first series circuit C1. A collector of the switch 61 is connected to the main positive bus LU.

The second series circuit C2 is connected to the MCU 50. Specifically, in the second series circuit C2, a second connection node between the second element 64 and the third element 65 is connected to the MCU 50.

The MCU 50 includes the first operational amplifier 56, the analog-to-digital converter (ADC) 57, the processor 55, and a second operational amplifier 58 whose amplification factor is 1. In all embodiments, at least one of the first operational amplifier 56, the ADC 57, and the second operational amplifier 58 may be provided outside the MCU 50.

The first operational amplifier 56 includes a non-inversion input terminal (+) and an inversion input terminal (−), amplifies a differential input value obtained by subtracting a potential $V_-$ input to the inversion input terminal from a potential $V_+$ input to the non-inversion input terminal by a predetermined amplification factor A and outputs the amplified differential input value. The differential input value changes when the electric resistance value of the load 21 changes in accordance with the temperature thereof. Similarly, an output signal of the first operational amplifier 56 changes when the electric resistance value of the load 21 changes in accordance with the temperature thereof. In the following description, unless otherwise specified, the first operational amplifier 56 is treated as an input-output rail-to-rail type operational amplifier.

The first operational amplifier 56 includes a pair of power supply terminals. As an example, the reference voltage $V_{REF}$ is supplied from the LDO regulator 60 to the power supply terminal on the high potential side (hereinafter, referred to as a positive power supply terminal). The power supply terminal on the low potential side (hereinafter, referred to as a negative power supply terminal) is connected to the main negative bus LD.

When the power supply terminal of the first operational amplifier 56 is connected in this way, an upper limit value of a range of the differential input value that can be amplified by the first operational amplifier 56 (hereinafter referred to as an amplification range) is a potential of the positive power supply terminal (reference voltage $V_{REF}$ as an example), and a lower limit value of the amplification range is a potential of the negative power supply terminal (0V). Accordingly, when the differential input value is below 0 V, the differential input value is clipped to 0 V (such a phenomenon is referred to as a lower limit clip). Similarly, when the differential input value is above the reference voltage $V_{REF}$, the differential input value is clipped to the reference voltage $V_{REF}$ (such a phenomenon is referred to as an upper limit clip). If the potential (reference voltage $V_{REF}$) of the positive power supply terminal of the first operational amplifier 56 coincides with the voltage $V_{OUT}$, occurrence of the upper limit clip can be prevented. Therefore, it is particularly important to devise prevention of occurrence of the lower limit clip.

When the first operational amplifier 56 is not the input-output rail-to-rail type operational amplifier, the upper limit value of the amplification range is lower than that of the input-output rail-to-rail type operational amplifier, and the lower limit value of the amplification range is higher than that of the input-output rail-to-rail type operational amplifier. In other words, the amplification range of the first operational amplifier 56 which is not the input-output rail-to-rail type operational amplifier is narrower than the amplification range of the input-output rail-to-rail type first operational amplifier 56. Therefore, it should be noted that when the first operational amplifier 56 that is not the input-output rail-to-rail type operational amplifier is used, the upper limit clip and the lower limit clip occur easily.

The first series circuit C1 is connected to the non-inversion input terminal of the first operational amplifier 56. Specifically, the non-inversion input terminal of the first operational amplifier 56 is connected to the first connection node between the first element 63 and the load 21 in the first series circuit C1.

The second series circuit C2 is connected indirectly to the inversion input terminal of the first operational amplifier 56. Specifically, the inversion input terminal of the first operational amplifier 56 is connected, via the second operational amplifier 58, to the second connection node between the second element 64 and the third element 65 in the second series circuit C2.

A non-inversion input terminal of the second operational amplifier 58 is connected to the second connection node between the second element 64 and the third element 65 in the second series circuit C2. An inversion input terminal of the second operational amplifier 58 is connected to a circuit that supplies a predetermined potential $V_{PSEUDO}$. An output terminal of the second operational amplifier 58 is connected to the inversion input terminal of the first operational amplifier 56. For example, the reference voltage $V_{REF}$ is supplied to a positive power supply terminal of the second operational amplifier 58. A negative power supply terminal of the second operational amplifier 58 is connected to, for example, the main negative bus LD.

The second operational amplifier 58 functions to lower the lower limit value of the amplification range of the first operational amplifier 56 (that is, the potential of the negative power supply terminal of the first operational amplifier 56) in a pseudo manner. Due to presence of the second operational amplifier 58, the differential input value of the first operational amplifier 56 is raised by the predetermined potential $V_{PSEUDO}$. As a result, even when a potential of the first connection node between the first element 63 and the load 21 is less than a potential of the second connection node between the second element 64 and the third element 65, it is possible to prevent the occurrence of the lower limit clip, and it is possible to detect the temperature of the load 21 with high accuracy.

Figure 7:
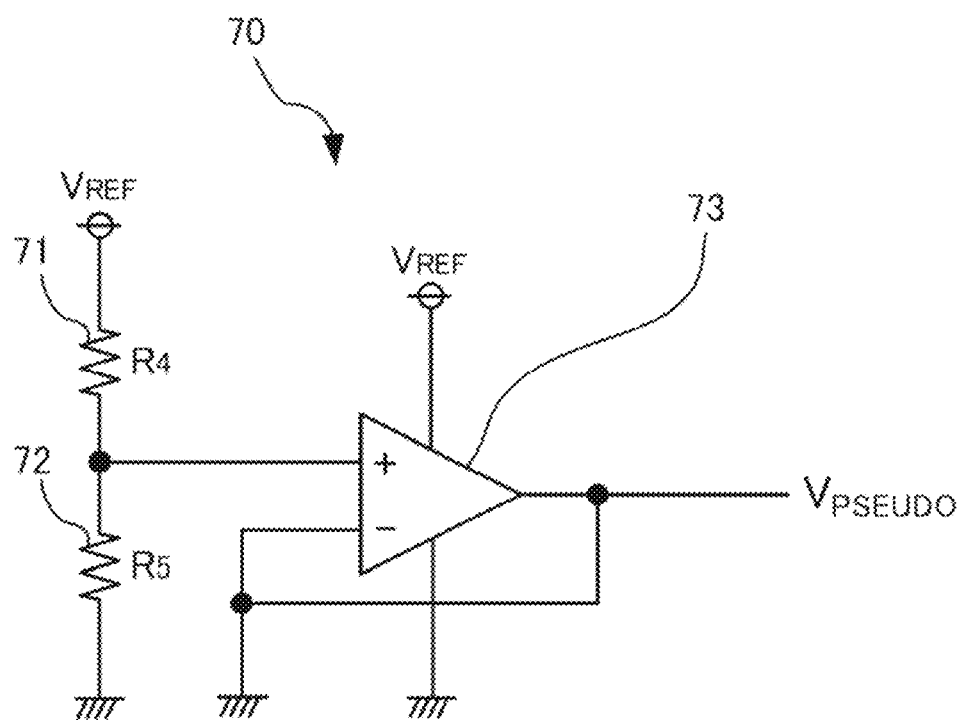
FIG. 7 shows an example of a supply circuit of a predetermined potential $V_{PSEUDO}$ of the power supply unit of the first embodiment shown in FIG. 6.

FIG. 7 shows an example of a supply circuit of the predetermined potential $V_{PSEUDO}$ of the power supply unit of a first embodiment shown in FIG. 6. This circuit includes a fourth element 71 which has a fourth electric resistance value $R_4$, a fifth element 72 which has a fifth electric resistance value $R_5$, and an operational amplifier 73.

Each of the fourth element 71 and the fifth element 72 is an element having an electric resistance value, for example, a resistor, a diode, or a transistor. In the example of FIG. 7, the fourth element 71 and the fifth element 72 are resistors. The fourth element 71 and the fifth element 72 are connected in series. A circuit that supplies the reference voltage $V_{REF}$ (for example, the LDO regulator 60) is connected to a terminal, which is located on a side opposite to the side of the fifth element 72, of the fourth element 71. The main negative bus LD is connected to a terminal, which is located on a side opposite to the side of the fourth element 71, of the fifth element 72.

A connection node between the fourth element 71 and the fifth element 72 is connected to a non-inversion input terminal of the operational amplifier 73. An inversion input terminal and an output terminal of the operational amplifier 73 are connected without going through any element that has an electric resistance value. A connection node between the inversion input terminal and the output terminal of the operational amplifier 73 is connected to the main negative bus LD. As a result, the operational amplifier 73 functions as a voltage follower that directly outputs the differential input value without amplification. The predetermined potential $V_{PSEUDO}$, which is a potential of the output terminal of the operational amplifier 73 shown in FIG. 7, is expressed by the following formula (A).

$$V_{PSEUDO} = \{R_4/(R_4+R_5)\} \cdot V_{REF} \qquad (A)$$

According to the circuit shown in FIG. 7, the predetermined potential $V_{PSEUDO}$ can be generated by dividing the reference voltage $V_{REF}$ which serves as an input voltage. According to such a generation circuit, it is easy to set the predetermined potential $V_{PSEUDO}$ to a desired value by adjusting the fourth electric resistance value $R_4$ and the fifth electric resistance value $R_5$. In order to simplify the circuit, it is also possible to directly use the reference voltage $V_{REF}$ as the predetermined potential $V_{PSEUDO}$. The supply circuit of the predetermined potential $V_{PSEUDO}$ is not limited to FIG. 7, and may also be an LDO regulator or a DC/DC converter that is separate from the LDO regulator 60. That is, the predetermined potential $V_{PSEUDO}$ may also be generated by stepping down the reference voltage $V_{REF}$ serving as the input voltage.

The ADC 57 converts the output signal of the first operational amplifier 56 into a digital signal and outputs the digital signal. The ADC 57 is operated with the reference voltage $V_{REF}$.

As shown in FIG. 5, the MCU 50 includes, as functional blocks implemented by the processor 55 executing programs stored in the ROM, an aerosol generation request detector 51, a temperature detector 52, a power controller 53, and a notification controller 54.

The aerosol generation request detector 51 detects an aerosol generation request based on an output result of the intake sensor 15. The intake sensor 15 is configured to output a value of a pressure (internal pressure) change in the power supply unit 10 caused by inhale of the user through the inhale port 32. The intake sensor 15 is, for example, a pressure sensor that outputs an output value (for example, a voltage value or a current value) corresponding to an internal pressure that changes in accordance with a flow rate of air inhaled from the intake port (not shown) toward the inhale port 32 (that is, the puff operation of the user). The intake sensor 15 may be constituted by a condenser microphone or the like. The intake sensor 15 may output an analog value, or may output a digital value converted from the analog value.

The temperature detector 52 detects the temperature of the load 21 based on the output signal of the first operational amplifier 56 shown in FIG. 6. When the switch 61 is turned off while the switch 62 is turned on, currents flow in the first series circuit C1 and the second series circuit C2 respectively, and the temperature detector 52 detects the temperature of the load 21 based on the output signal of the first operational amplifier 56 at this time.

The notification controller 54 controls the notification unit 45 to notify various types of information. For example, the notification controller 54 controls the notification unit 45 to notify replacement timing of the second cartridge 30 in response to detection of the replacement timing of the second cartridge 30. The notification controller 54 detects and notifies the replacement timing of the second cartridge 30 based on the cumulative number of times of puff operations or cumulative time of energization to the load 21 stored in the memory 18. The notification controller 54 is not limited to only notify the replacement timing of the second cartridge 30, and may also notify replacement timing of the first cartridge 20, replacement timing of the power supply 12, charging timing of the power supply 12 and the like.

In a state where one unused second cartridge 30 is set, when the puff operation is performed a predetermined number of times or when the cumulative time of energization to the load 21 reaches a predetermined value (for example, 120 seconds) due to the puff operation, the notification controller 54 determines that the second cartridge 30 has been used up (that is, a remaining amount is zero or empty), and notifies the replacement timing of the second cartridge 30.

When it is determined that all the second cartridges 30 included in the above one set have been used up, the notification controller 54 may determine that one first cartridge 20 included in the one set has been used up (that is, the remaining amount is zero or empty) and notify the replacement timing of the first cartridge 20.

When the aerosol generation request detector 51 detects the aerosol generation request, the power controller 53 turns on or off the switch 61 and the switch 62 so as to control discharge of the power supply 12 performed via the discharge terminal 41. By turning on the switch 61 and turning off the switch 62, the power controller 53 causes a current to flow through the load 21 to discharge electricity to the load 21 so as to generate the aerosol.

When the temperature of the load 21 detected by the temperature detector 52 exceeds a predetermined upper limit temperature $T_{MAX}$, the power controller 53 performs control to stop heating of the load 21 (discharge to the load 21). When a temperature of the power supply 12 detected by a thermistor (not shown) or the like is lower than a predetermined lower limit temperature $T_{MIN}$, the power controller 53 performs control to disallow the heating of the load 21 (discharge to the load 21). When the temperature of the power supply 12 is near the lower limit temperature $T_{MIN}$ or lower than the lower limit temperature $T_{MIN}$, the temperature of the power supply 12 and the temperature of the load 21 are substantially equal. That is, in the aerosol inhaler 1, the load 21 operates in an operating temperature range that is equal to or higher than the lower limit temperature $T_{MIN}$ and equal to or lower than the upper limit temperature $T_{MAX}$.

An operation of the electric circuit shown in FIG. 6 will be described. Upon detecting the aerosol generation request, the processor 55 of the MCU 50 sends a turn-on command to the switch 61, and sends a turn-off command to the switch 62. In response to such commands, the switch 61 is turned on, and the switch 62 is turned off. For example, by minimizing the electric resistance value $R_{HTR}$ of the load 21 in the bridge circuit, a large current can flow through the load 21 while a current flowing through the first element 63, the second element 64, and the third element 65 becomes zero or substantially zero in a state where the switch 61 is turned on while the switch 62 is turned off. As a result, the load 21 is heated to generate the aerosol.

After a lapse of a predetermined time from a start of the heating of the load 21, the processor 55 sends the turn-off command to the switch 61, and sends the turn-on command to the switch 62. When the switch 61 is turned off while the switch 62 is turned on in response to such commands, currents flow to the first series circuit C1 and the second series circuit C2. The differential input value is amplified by the first operational amplifier 56, subjected to digital conversion performed by the ADC 57, and input to the processor 55. The processor 55 detects the temperature of the load 21 based on an input signal from the ADC 57.

After detecting the temperature of the load 21, the processor 55 sends the turn-on command to the switch 61, and sends the turn-off command to the switch 62 to start generation of the aerosol again. By repeating the above operations, the temperature of the load 21 is detected at high frequency during the generation of the aerosol in response to the aerosol generation request.

Hereinafter, a configuration capable of improving detection accuracy of the temperature of the load 21 in the first embodiment shown in FIG. 6 will be described. In order to improve the detection accuracy of the temperature of the load, it is required that the upper limit clip and the lower limit clip (in particular, the lower limit clip) do not occur in the operating temperature range of the load 21.

In the power supply unit 10 of the first embodiment, a value of the predetermined potential $V_{PSEUDO}$ is determined in such a manner that the differential input value of the first operational amplifier 56 is larger than the potential of the negative power supply terminal of the first operational amplifier 56 in a state where a potential of the first connection node between the first element 63 and the load 21 is less than a potential of the second connection node between the second element 64 and the third element 65 while the temperature of the load 21 is within the operating temperature range.

Figure 8:
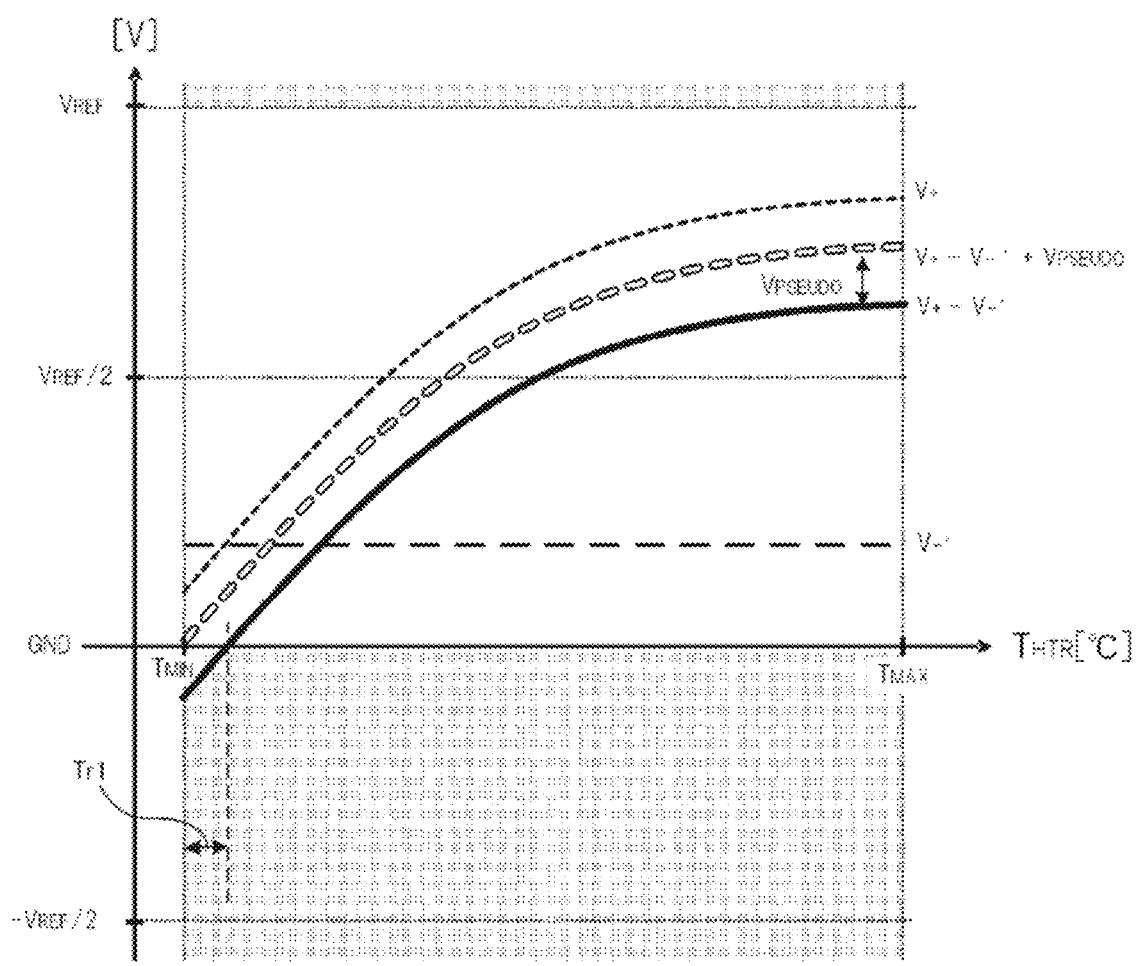
FIG. 8 is a graph showing an example of a differential input value of a first operational amplifier 56 in a power supply unit 10 of the first embodiment shown in FIG. 6.

FIG. 8 is a graph showing an example of the differential input value of the first operational amplifier 56 in the power supply unit 10 of the first embodiment shown in FIG. 6. In FIG. 8, and FIGS. 9, 11, 13 and 15 to be described below, a vertical axis represents a voltage (potential) while a horizontal axis represents the temperature of the load 21.

Figure 9:
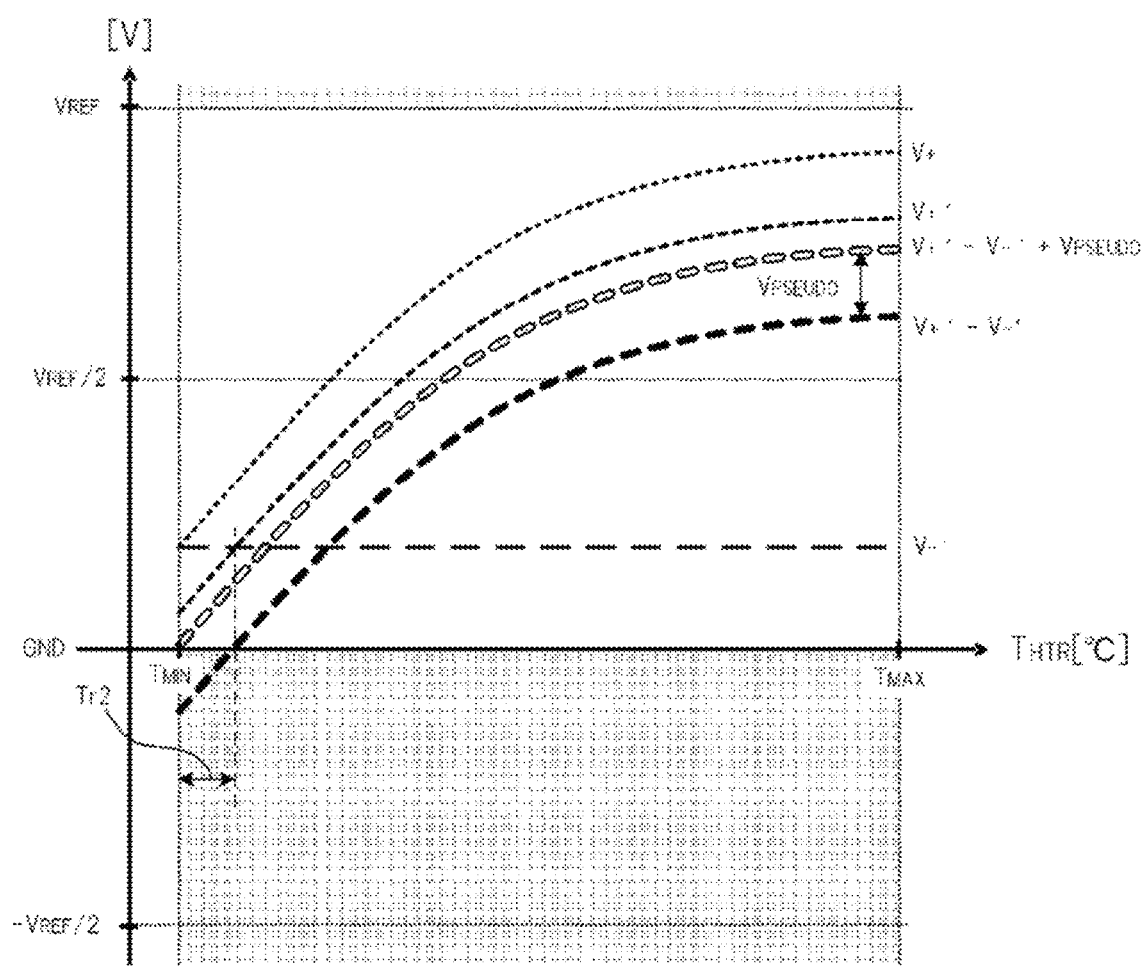
FIG. 9 is a graph showing another example of the differential input value of the first operational amplifier 56 in the power supply unit 10 of the first embodiment shown in FIG. 6.

In FIGS. 8 and 9, a graph denoted by "$V_+$" represents the potential of the first connection node between the first element 63 and the load 21. In FIGS. 8 and 9, a graph denoted by "$V_-$" represents the potential of the second connection node between the second element 64 and the third element 65. In FIG. 8, a graph denoted by "$V_+ - V_-' + V_{PSEUDO}$" represents the differential input value of the first operational amplifier 56.

In the first embodiment shown in FIG. 6, a configuration in which the second connection node and the inversion input terminal of the first operational amplifier 56 are directly connected without the second operational amplifier 58 is described as a first reference circuit configuration. In FIG. 8, a graph denoted by "$V_+ - V_-$" represents the differential input value of the first operational amplifier 56 in the first reference circuit configuration. In the example shown in FIG. 8, in a temperature range Tr1 in the operating temperature range, the potential "$V_+$" of the first connection node is less than the potential "$V_-$" of the second connection node. Therefore, in the first reference circuit configuration, the lower limit clip occurs in the operating temperature range.

Meanwhile, in the first embodiment shown in FIG. 6, in the temperature range Tr1, the value of the predetermined potential $V_{PSEUDO}$ is determined in such a manner that the differential input value of the first operational amplifier 56 is larger than 0 V. Further, in the first embodiment shown in FIG. 6, the value of the predetermined potential $V_{PSEUDO}$ is determined in such a manner that the differential input value of the first operational amplifier 56 is smaller than the potential of the positive power supply terminal (reference voltage $V_{REF}$) at the upper limit temperature $T_{MAX}$ of the operating temperature range. By determining the predetermined potential $V_{PSEUDO}$ in this way, occurrence of the lower limit clip and the upper limit clip in the first operational amplifier 56 is prevented in the operating temperature range. Therefore, the detection accuracy of the temperature of the load 21 can be improved.

According to the first embodiment shown in FIG. 6, a configuration in which the potential "$V_+$" of the first connection node is less than the potential "$V_-$" of the second connection node in the operating temperature range can be adopted as the bridge circuit. Therefore, restrictions on electric resistance values of each element of the bridge circuit can be relaxed, and a degree of freedom in design can be improved.

The state where the potential "$V_+$" of the first connection node is less than the potential "$V_-$" of the second connection node may also be caused by a manufacturing error of the electric resistance value $R_{HTR}$ of the load 21. The electric resistance value $R_{HTR}$ of the load 21 can generally have a manufacturing error of about ±10%. Therefore, for example, even when the bridge circuit can be designed in such a manner that the potential "$V_+$" of the first connection node is equal to or higher than the potential "$V_-$" of the second connection node in the operating temperature range, the state where the potential "$V_+$" of the first connection node is less than the potential "$V_-$" of the second connection node may still occur due to the manufacturing error. Therefore, it is desirable that the value of the predetermined potential $V_{PSEUDO}$ is determined in consideration of the manufacturing error of the electric resistance value $R_{HTR}$ of the load 21.

FIG. 9 is a graph showing another example of the differential input value of the first operational amplifier 56 in the power supply unit 10 of the first embodiment shown in FIG. 6. In the example shown in FIG. 9, it is assumed that the electric resistance value $R_{HTR}$ of the load 21 is designed in such a manner that the potential "$V_+$" of the first connection node and the potential "$V_-$" of the second connection node are equal in a state where the temperature of the load 21 is equal to the lower limit temperature $T_{MIN}$. By designing in this way, the amplification factor A of the first operational amplifier 56 can be increased, and thus a detection resolution of the temperature of the load 21 can be improved.

In FIG. 9, a graph denoted by "$V_+'$" indicates the potential of the first connection node when there is an error of −10% in the electric resistance value $R_{HTR}$ of the load 21 as compared with a design value. As described above, when there is an error of −10% in the electric resistance value $R_{HTR}$ of the load 21, the differential input value of the first operational amplifier 56 in the first reference circuit configuration is as shown in a graph "$V_+' - V_-'$" in FIG. 9, and the lower limit clip occurs in a temperature range Tr2 in the operating temperature range.

In the first embodiment, the value of the predetermined potential $V_{PSEUDO}$ is determined in such a manner that the differential input value of the first operational amplifier 56 is larger than 0 V in the temperature range Tr2 in which the potential of the first connection node is less than the potential of the second connection node in the case where there an error of −10% in the electric resistance value $R_{HTR}$ of the load 21 as compared with the design value.

In the first embodiment, when there is an error of −10% in the electric resistance value $R_{HTR}$ of the load 21 while the temperature of the load 21 is equal to the upper limit temperature $T_{MAX}$, the value of the predetermined potential $V_{PSEUDO}$ is determined in such a manner that the differential input value of the first operational amplifier 56 is less than the potential of the positive power supply terminal of the first operational amplifier 56. A graph shown by "$V_+' - V_-' + V_{PSEUDO}$" shown in FIG. 9 shows the differential input value of the first operational amplifier 56 when there is an error of −10% in the electric resistance value $R_{HTR}$ of the load 21.

As described above, by determining the predetermined potential $V_{PSEUDO}$ in consideration of the manufacturing error of the load 21, the differential input value of the first operational amplifier 56 is between the potential of the negative power supply terminal and the potential of the positive power supply terminal in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved.

(First Modification of First Embodiment of Electric Circuit)

Figure 10:
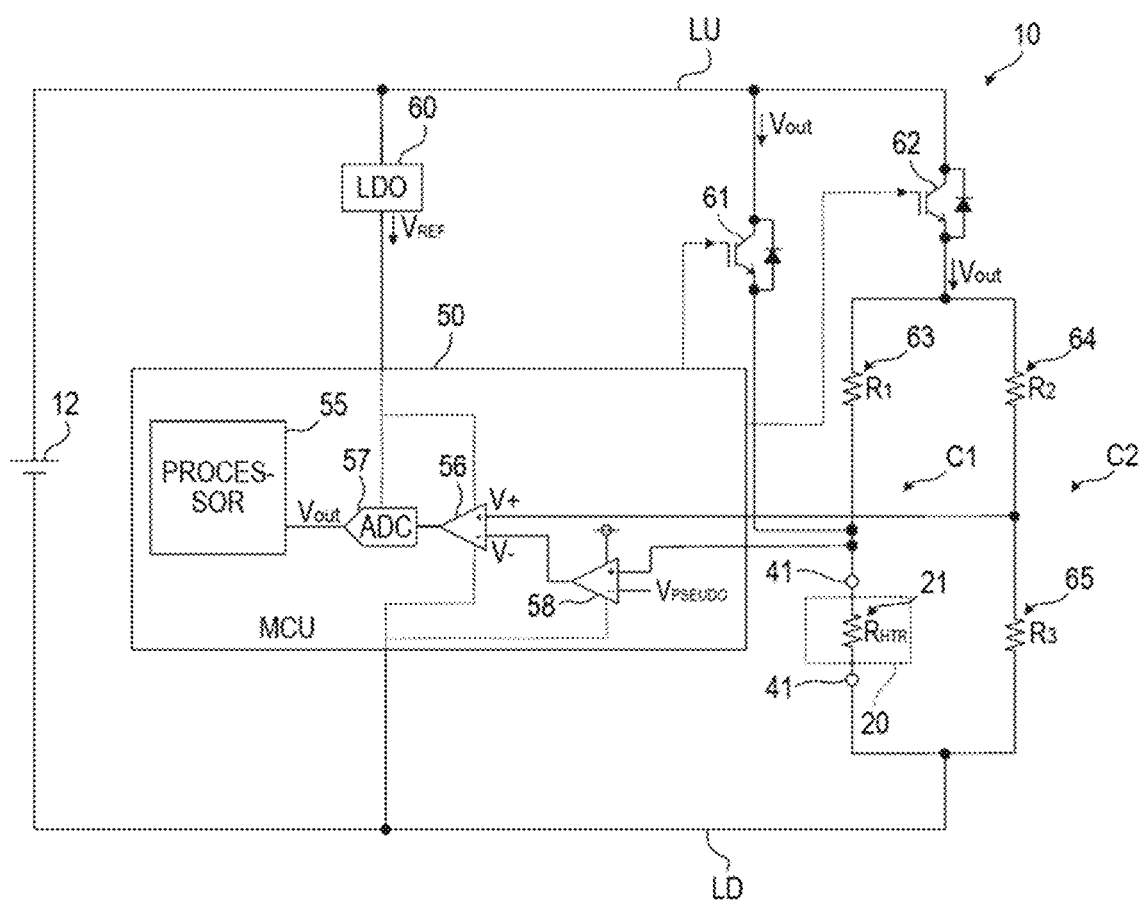
FIG. 10 is a schematic view showing a first modification of a circuit configuration of the power supply unit 10 of the first embodiment shown in FIG. 6.

FIG. 10 is a schematic view showing a first modification of the circuit configuration of the power supply unit 10 of the first embodiment shown in FIG. 6. The power supply unit 10 shown in FIG. 10 is the same as the circuit configuration of FIG. 6 except that a connection relationship between the first operational amplifier 56, the second operational amplifier 58 and the bridge circuit is changed. In the power supply unit 10 shown in FIG. 10, the non-inversion input terminal of the second operational amplifier 58 is connected to the first connection node between the first element 63 and the load 21. The non-inversion input terminal of the first operational amplifier 56 is connected to the second connection node between the second element 64 and the third element 65.

In the power supply unit 10 shown in FIG. 10, the value of the predetermined potential $V_{PSEUDO}$ is determined in such a manner that the differential input value of the first operational amplifier 56 is larger than the potential of the negative power supply terminal of the first operational amplifier 56 in a state where the potential of the second connection node is less than the potential of the first connection node while the temperature of the load 21 is within the operating temperature range.

Figure 11:
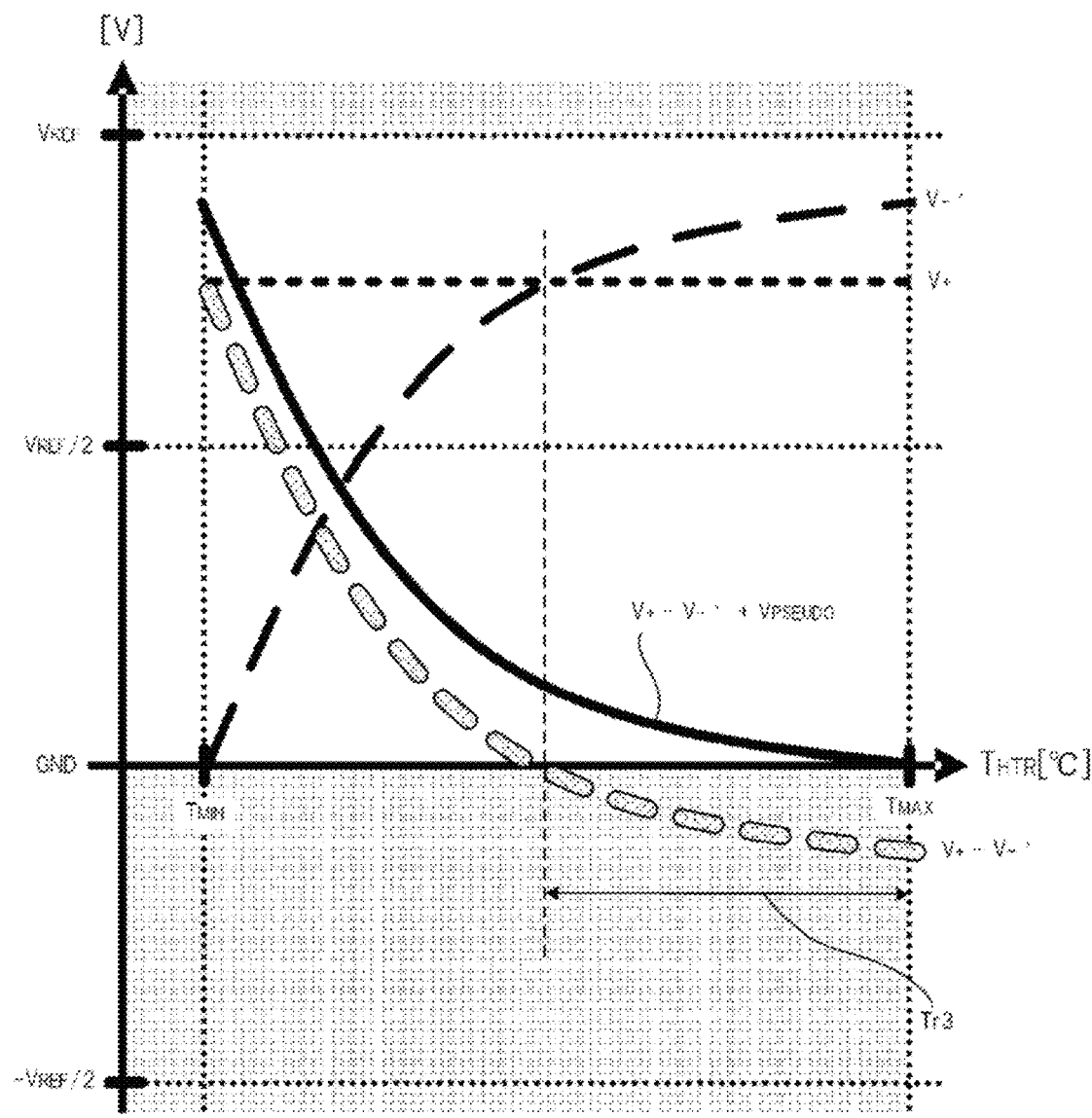
FIG. 11 is a graph showing an example of the differential input value of the first operational amplifier 56 in the power supply unit 10 shown in FIG. 10.

FIG. 11 is a graph showing an example of the differential input value of the first operational amplifier 56 in the power supply unit 10 shown in FIG. 10. In FIG. 11, a graph denoted by "$V_+$" represents the potential of the second connection node between the second element 64 and the third element 65. In FIG. 11, a graph denoted by "$V_-'$" represents the potential of the first connection node between the first element 63 and the load 21. In FIG. 11, a graph denoted by "$V_+ - V_-' + V_{PSEUDO}$" represents the differential input value of the first operational amplifier 56.

In the power supply unit 10 shown in FIG. 10, a configuration in which the first connection node and the inversion input terminal of the first operational amplifier 56 are directly connected without the second operational amplifier 58 is described as a second reference circuit configuration. In FIG. 11, a graph denoted by "$V_+ - V_-'$" represents the differential input value of the first operational amplifier 56 in the second reference circuit configuration.

As an example, in the power supply unit 10 shown in FIG. 10, the electric resistance value $R_{HTR}$ of the load 21 is designed in such a manner that the potential "$V_+$" of the second connection node and the potential "$V_-'$" of the first connection node are equal in a state where the temperature of the load 21 is equal to the upper limit temperature $T_{MAX}$. FIG. 11 shows an example in which there is an error of +10% in the electric resistance value $R_{HTR}$ of the load 21.

Since there is an error of +10% in the electric resistance value $R_{HTR}$ of the load 21, in the example shown in FIG. 11, the potential "$V_+$" of the second connection node is less than the potential "$V_-$" of the first connection node in a temperature range Tr3 in the operating temperature range. Therefore, in the case of the second reference circuit configuration, the lower limit clip occurs in the temperature range Tr3 in the operating temperature range. When there is an error of +10% in the electric resistance value $R_{HTR}$ of the load 21, the lower limit clip does not occur.

In the power supply unit 10 shown in FIG. 10, in the temperature range Tr3, the value of the predetermined potential $V_{PSEUDO}$ is determined in such a manner that the differential input value of the first operational amplifier 56 is larger than 0 V. Further, in the power supply unit 10 shown in FIG. 10, the value of the predetermined potential $V_{PSEUDO}$ is determined in such a manner that the differential input value of the first operational amplifier 56 is smaller than the potential of the positive power supply terminal (reference voltage $V_{REF}$) in a state where there is an error of +10% in the electric resistance value $R_{HTR}$ of the load 21 while the temperature of the load 21 is equal to the lower limit temperature $T_{MIN}$. Further, in the power supply unit 10 shown in FIG. 10, the value of the predetermined potential $V_{PSEUDO}$ is determined in such a manner that the differential input value of the first operational amplifier 56 is smaller than the potential of the positive power supply terminal (reference voltage $V_{REF}$) in a state where there is an error of −10% in the electric resistance value $R_{HTR}$ of the load 21 while the temperature of the load 21 is equal to the lower limit temperature $T_{MIN}$.

By determining the predetermined potential $V_{PSEUDO}$ in this way, the differential input value of the first operational amplifier 56 is between the potential of the negative power supply terminal and the potential of the positive power supply terminal in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved.

(Second Modification of First Embodiment of Electric Circuit)

Figure 12:
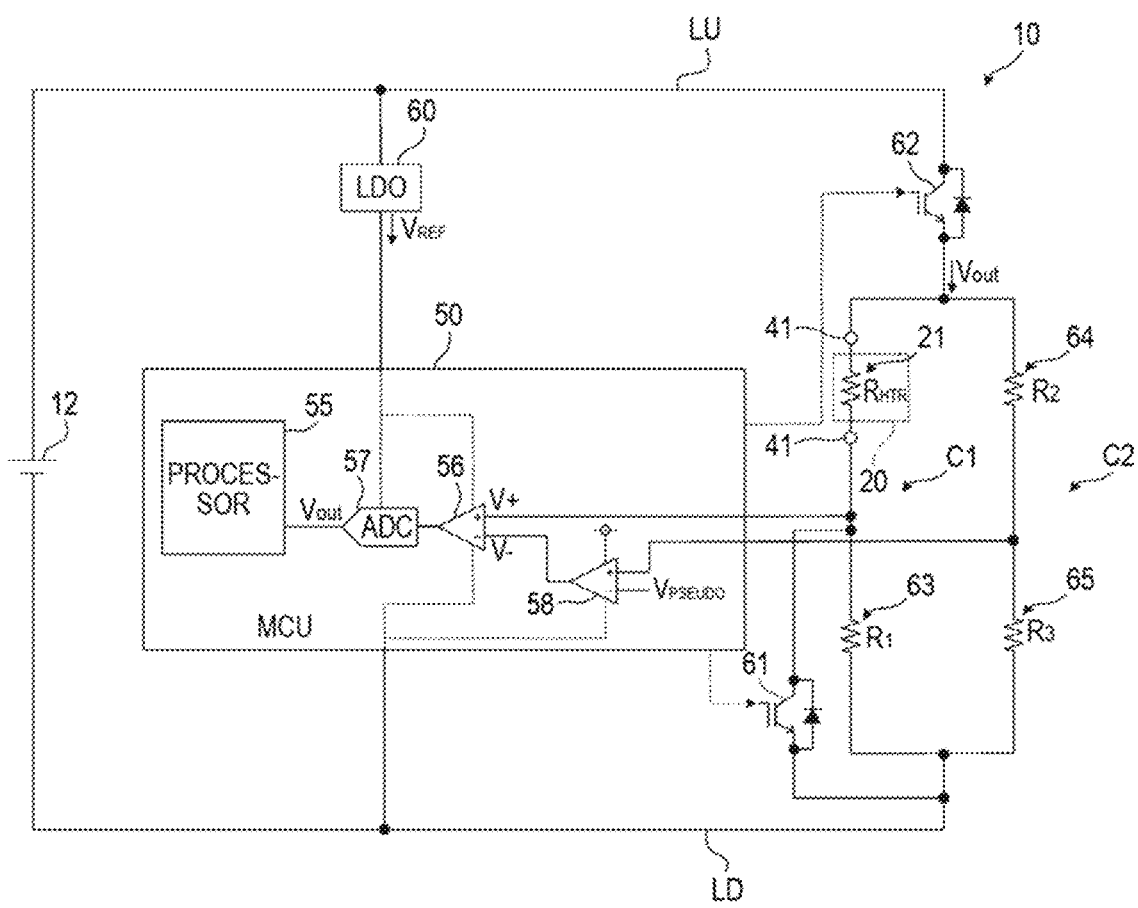
FIG. 12 is a schematic view showing a second modification of the circuit configuration of the power supply unit 10 of the first embodiment shown in FIG. 6.

FIG. 12 is a schematic view showing a second modification of the circuit configuration of the power supply unit 10 of the first embodiment shown in FIG. 6. The power supply unit 10 shown in FIG. 12 is the same as the circuit configuration of FIG. 6 except that positions of the first element 63 and the load 21 are reversed in the first series circuit C1 while a position of the switch 61 is changed.

The switch 61 is connected between the first connection node and the main negative bus LD. In the power supply unit 10 shown in FIG. 12, the load 21 is heated when the switch 61 and the switch 62 are both turned on. The temperature of the load 21 is detected when the switch 61 is turned off while the switch 62 is turned on.

In the power supply unit 10 shown in FIG. 12, the value of the predetermined potential $V_{PSEUDO}$ is determined in such a manner that the differential input value of the first operational amplifier 56 is larger than the potential of the negative power supply terminal of the first operational amplifier 56 in a state where the potential of the first connection node is less than the potential of the second connection node while the temperature of the load 21 is within the operating temperature range.

Figure 13:
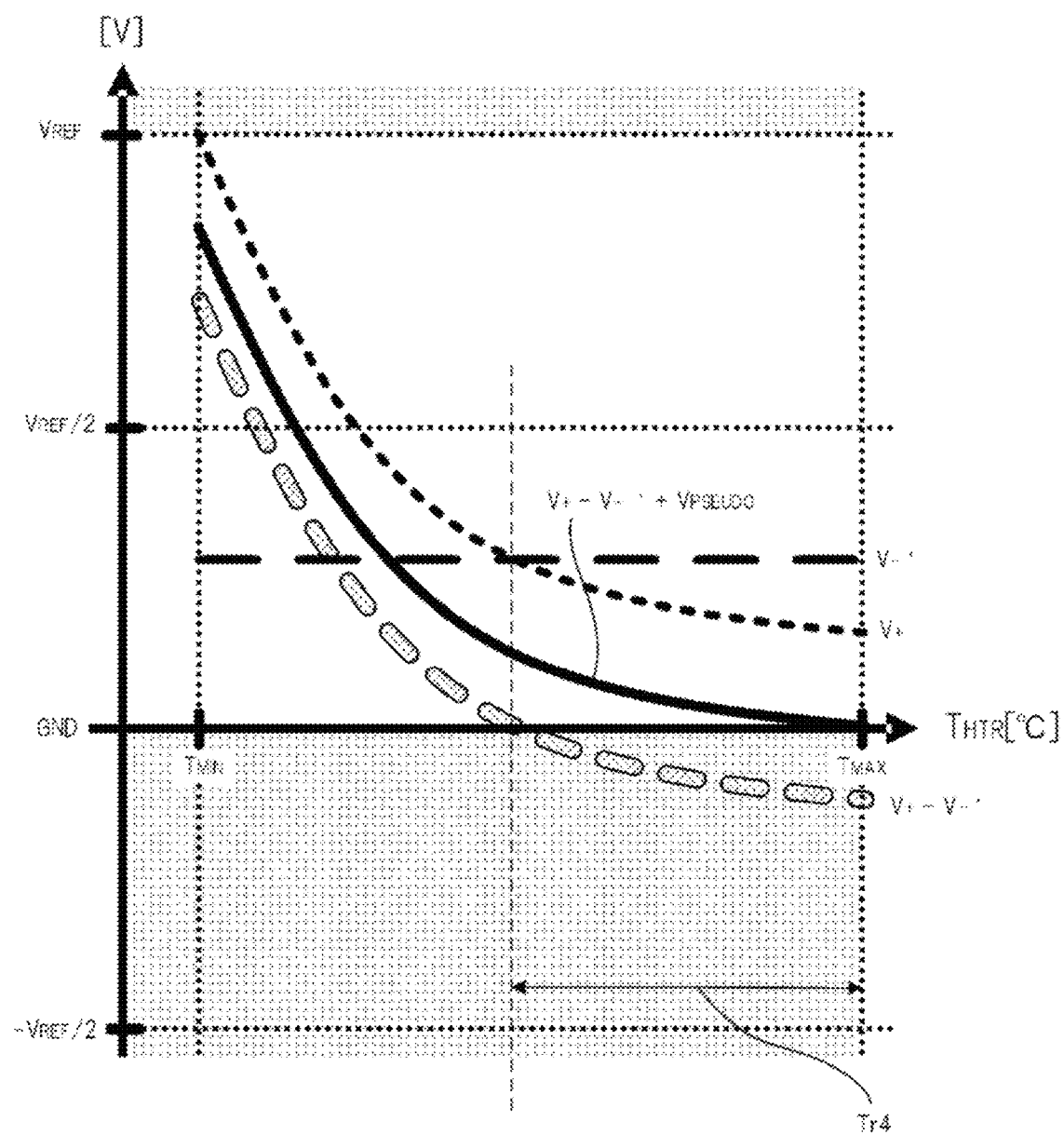
FIG. 13 is a graph showing an example of the differential input value of the first operational amplifier 56 in the power supply unit 10 shown in FIG. 12.

FIG. 13 is a graph showing an example of the differential input value of the first operational amplifier 56 in the power supply unit 10 shown in FIG. 12. In FIG. 13, a graph denoted by "$V_+$" represents the potential of the first connection node between the first element 63 and the load 21. In FIG. 13, a graph denoted by "$V_-$" represents the potential of the second connection node between the second element 64 and the third element 65. In FIG. 13, a graph denoted by "$V_+ - V_-' + V_{PSEUDO}$" represents the differential input value of the first operational amplifier 56.

In the power supply unit 10 shown in FIG. 13, a configuration in which the second connection node and the inversion input terminal of the first operational amplifier 56 are directly connected without the second operational amplifier 58 is described as a third reference circuit configuration. In FIG. 13, a graph denoted by "$V_+ - V_-$" represents the differential input value of the first operational amplifier 56 in the third reference circuit configuration.

As an example, in the power supply unit 10 shown in FIG. 12, the electric resistance value $R_{HTR}$ of the load 21 is designed in such a manner that the potential "$V_+$" of the first connection node and the potential "$V_-$" of the second connection node are equal in a state where the temperature of the load 21 is equal to the upper limit temperature $T_{MAX}$. FIG. 13 shows an example in which there is an error of −10% in the electric resistance value $R_{HTR}$ of the load 21.

Since there is an error of −10% in the electric resistance value $R_{HTR}$ of the load 21, in the example shown in FIG. 13, the potential "$V_+$" of the first connection node is less than the potential "V_−" of the second connection node in a temperature range Tr4 in the operating temperature range. Therefore, in the case of the third reference circuit configuration, the lower limit clip occurs in the temperature range Tr4 in the operating temperature range. When there is an error of +10% in the electric resistance value $R_{HTR}$ of the load 21, the lower limit clip does not occur.

In the power supply unit 10 shown in FIG. 12, in the temperature range Tr4, the value of the predetermined potential $V_{PSEUDO}$ is determined in such a manner that the differential input value of the first operational amplifier 56 is larger than 0 V. Further, in the power supply unit 10 shown in FIG. 12, the value of the predetermined potential $V_{PSEUDO}$ is determined in such a manner that the differential input value of the first operational amplifier 56 is smaller than the potential of the positive power supply terminal (reference voltage $V_{REF}$) in a state where there is an error of −10% in the electric resistance value $R_{HTR}$ of the load 21 while the temperature of the load 21 is equal to the lower limit temperature $T_{MIN}$. Further, in the power supply unit 10 shown in FIG. 12, the value of the predetermined potential $V_{PSEUDO}$ is determined in such a manner that the differential input value of the first operational amplifier 56 is smaller than the potential of the positive power supply terminal (reference voltage $V_{REF}$) in a state where there is an error of +10% in the electric resistance value $R_{HTR}$ of the load 21 while the temperature of the load 21 is equal to the lower limit temperature $T_{MIN}$.

By determining the predetermined potential $V_{PSEUDO}$ in this way, the differential input value of the first operational amplifier 56 is between the potential of the negative power supply terminal and the potential of the positive power supply terminal in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved.

(Third Modification of First Embodiment of Electric Circuit)

Figure 14:
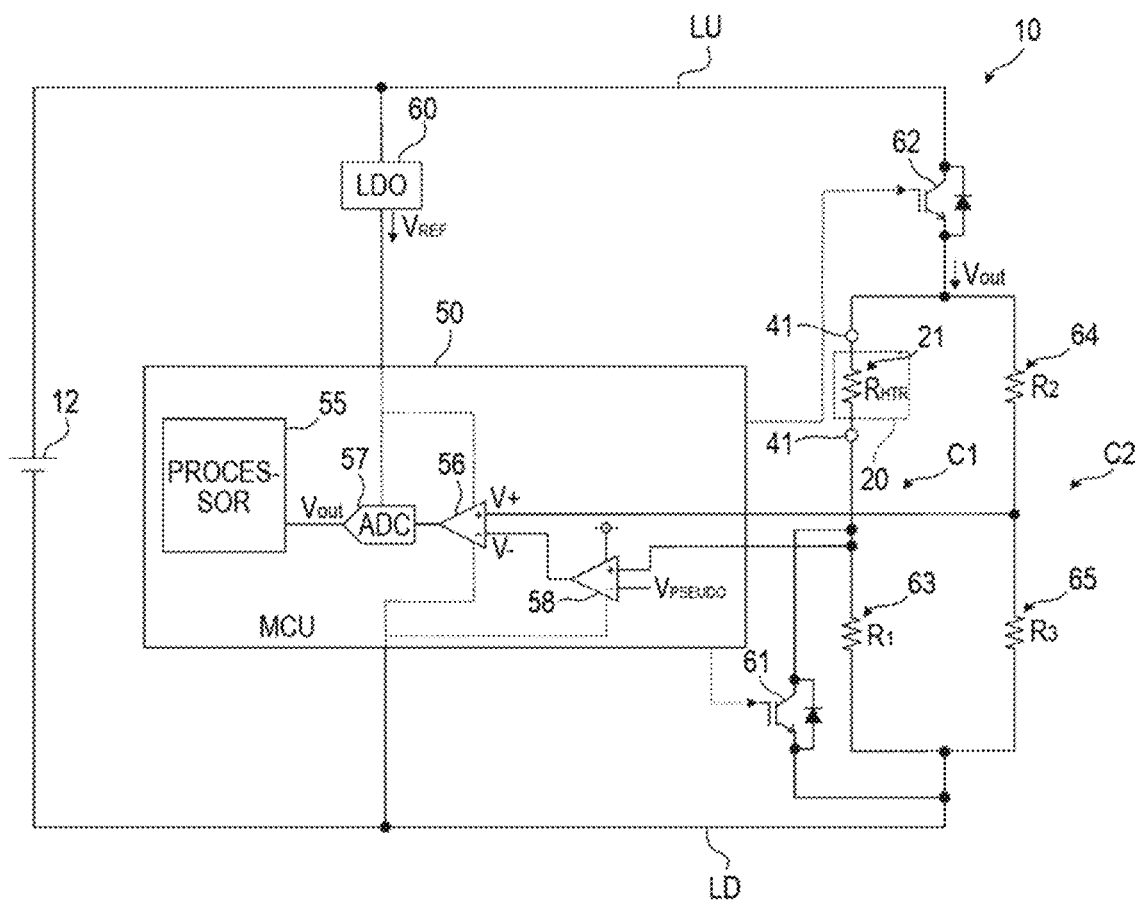
FIG. 14 is a schematic view showing a third modification of the circuit configuration of the power supply unit of the first embodiment shown in FIG. 6.

FIG. 14 is a schematic view showing a third modification of the circuit configuration of the power supply unit of the first embodiment shown in FIG. 6. The power supply unit 10 shown in FIG. 14 is the same as the circuit configuration of FIG. 12 except that the connection relationship between the first operational amplifier 56, the second operational amplifier 58 and the bridge circuit is changed. In the power supply unit 10 shown in FIG. 14, the non-inversion input terminal of the second operational amplifier 58 is connected to the first connection node between the first element 63 and the load 21. The non-inversion input terminal of the first operational amplifier 56 is connected to the second connection node between the second element 64 and the third element 65.

In the power supply unit 10 shown in FIG. 14, the value of the predetermined potential $V_{PSEUDO}$ is determined in such a manner that the differential input value of the first operational amplifier 56 is larger than the potential of the negative power supply terminal of the first operational amplifier 56 in a state where the potential of the second connection node is less than the potential of the first connection node while the temperature of the load 21 is within the operating temperature range.

Figure 15:
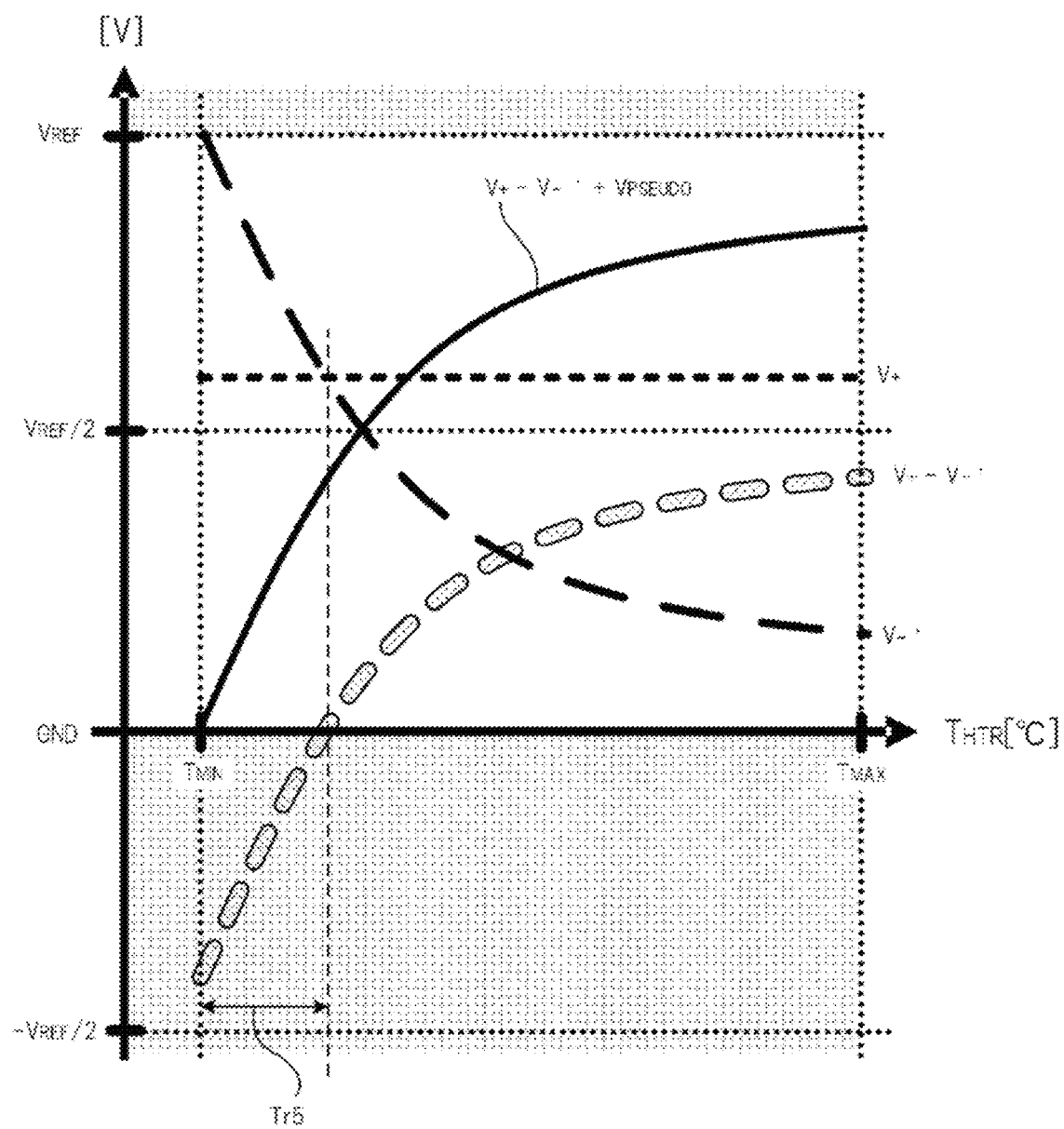
FIG. 15 is a graph showing an example of the differential input value of the first operational amplifier 56 in the power supply unit 10 shown in FIG. 14.

FIG. 15 is a graph showing an example of the differential input value of the first operational amplifier 56 in the power supply unit 10 shown in FIG. 14. In FIG. 15, a graph denoted by "$V_+$" represents the potential of the second connection node between the second element 64 and the third element 65. In FIG. 15, a graph denoted by "$V_−'$" represents the potential of the first connection node between the first element 63 and the load 21. In FIG. 15, a graph denoted by "$V_+-V_−'+V_{PSEUDO}$" represents the differential input value of the first operational amplifier 56.

In the power supply unit 10 shown in FIG. 14, the configuration in which the first connection node and the inversion input terminal of the first operational amplifier 56 are directly connected without the second operational amplifier 58 is described as a fourth reference circuit configuration. In FIG. 15, a graph denoted by "$V_+-V_−'$" represents the differential input value of the first operational amplifier 56 in the fourth reference circuit configuration.

As an example, in the power supply unit 10 shown in FIG. 14, the electric resistance value $R_{HTR}$ of the load 21 is designed in such a manner that the potential "$V_+$" of the second connection node and the potential "$V_−'$" of the first connection node are equal in a state where the temperature of the load 21 is equal to the lower limit temperature $T_{MIN}$. FIG. 15 shows an example in which there is an error of +10% in the electric resistance value $R_{HTR}$ of the load 21.

Since there is an error of +10% in the electric resistance value $R_{HTR}$ of the load 21, in the example shown in FIG. 15, the potential "$V_+$" of the second connection node is less than the potential "$V_−'$" of the first connection node in a temperature range Tr5 in the operating temperature range. Therefore, in the case of the fourth reference circuit configuration, the lower limit clip occurs in the temperature range Tr5 in the operating temperature range. When there is an error of −10% in the electric resistance value $R_{HTR}$ of the load 21, the lower limit clip does not occur.

In the power supply unit 10 shown in FIG. 14, in the temperature range Tr5, the value of the predetermined potential $V_{PSEUDO}$ is determined in such a manner that the differential input value of the first operational amplifier 56 is larger than 0 V. Further, in the power supply unit 10 shown in FIG. 14, the value of the predetermined potential $V_{PSEUDO}$ is determined in such a manner that the differential input value of the first operational amplifier 56 is smaller than the potential of the positive power supply terminal (reference voltage $V_{REF}$) in a state where there is an error of +10% in the electric resistance value $R_{HTR}$ of the load 21 while the temperature of the load 21 is equal to the upper limit temperature $T_{MAX}$. Further, in the power supply unit 10 shown in FIG. 14, the value of the predetermined potential $V_{PSEUDO}$ is determined in such a manner that the differential input value of the first operational amplifier 56 is smaller than the potential of the positive power supply terminal (reference voltage $V_{REF}$) in a state where there is an error of −10% in the electric resistance value $R_{HTR}$ of the load 21 while the temperature of the load 21 is equal to the upper limit temperature $T_{MAX}$.

By determining the predetermined potential $V_{PSEUDO}$ in this way, the differential input value of the first operational amplifier 56 is between the potential of the negative power supply terminal and the potential of the positive power supply terminal in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved.

In the first embodiment, the value of the predetermined potential $V_{PSEUDO}$ may also be a value equal to the potential of the negative power supply terminal of the first operational amplifier 56 in a state where: 1. there is a manufacturing error in the electric resistance value $R_{HTR}$ of the load 21, 2. the temperature of the load 21 is outside the operating temperature range, and 3. a potential of a connection node of a series circuit on a side, which is connected to the non-inversion input terminal of the first operational amplifier 56, of the bridge circuit is less than a potential of a connection node of a series circuit on a side which is connected to the inversion input terminal of the first operational amplifier 56. That is, the occurrence of the lower limit clip in the first operational amplifier 56 may be allowed outside the operating temperature range. In this way, an increase in the value of the predetermined potential $V_{PSEUDO}$ can be prevented, and a size of the circuit can be reduced.

Even when the first operational amplifier 56 is not an input-output rail-to-rail type operational amplifier, the occurrence of the lower limit clip and the upper limit clip can be prevented by setting the predetermined potential $V_{PSEUDO}$ to an appropriate value. In such a case, the lower limit clip may still occur even if the differential input value is larger than the potential of the negative power supply terminal. Similarly, the upper limit clip may still occur even if the differential input value is lower than the potential of the positive power supply terminal. In the following description, the differential input value at which the lower limit clip occurs in the first operational amplifier 56 that is not the input-output rail-to-rail type operational amplifier is described as a minimum value that can be acquired by the first operational amplifier 56. The differential input value at which the upper limit clip occurs in the first operational amplifier 56 that is not the input-output rail-to-rail type operational amplifier is described as a maximum value that can be acquired by the first operational amplifier 56. Specifically, in the above-described embodiment, the predetermined potential $V_{PSEUDO}$ may be set in such a manner that the differential input value is larger than the minimum value that can be acquired by the first operational amplifier 56. However, it should also be noted that the predetermined potential must be set in such a manner that the differential input value is smaller than the maximum value that can be acquired by the first operational amplifier 56.

(Second Embodiment of Electric Circuit)

Figure 16:
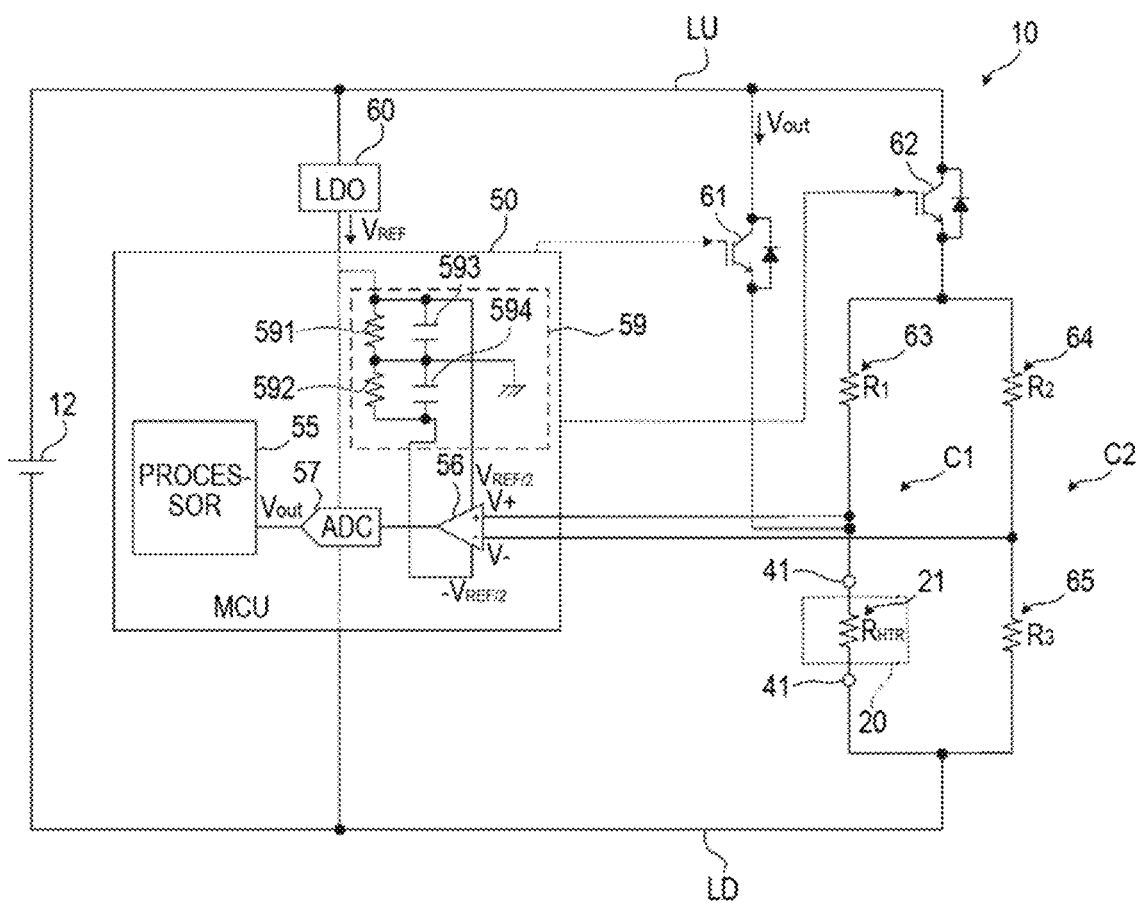
FIG. 16 is a schematic diagram showing a second embodiment of the circuit configuration of the power supply unit of the aerosol inhaler shown in FIG. 1.

FIG. 16 is a schematic diagram showing a second embodiment of the circuit configuration of the power supply unit of the aerosol inhaler shown in FIG. 1. The power supply unit 10 shown in FIG. 16 has the same configuration as that of FIG. 6 except that: 1. the inversion input terminal of the first operational amplifier 56 is directly connected to the second connection node between the second element 64 and the third element 65, 2. a rail splitter circuit 59 constituted by a resistor 591, a resistor 592, a condenser 593, and a condenser 594 is added, and 3. a potential is supplied from the rail splitter circuit 59 to the two power supply terminals of the first operational amplifier 56.

The rail splitter circuit 59 generates, from the reference voltage $V_{REF}$ (input voltage) generated by the LDO regulator 60, two potentials having the same absolute value and different positive and negative values (a positive potential of ($V_{REF}/2$) and a negative potential of ($-V_{REF}/2$)). The positive potential ($V_{REF}/2$) generated by the rail splitter circuit 59 is input to the positive power supply terminal of the first operational amplifier 56, and the negative potential ($-V_{REF}/2$) generated by the rail splitter circuit 59 is input to the negative power supply terminal of the first operational amplifier 56. In the rail splitter circuit 59, the absolute value of the generated potential can be adjusted by adjusting at least one of electric resistance values of the resistors 591, 592 and the input voltage.

According to the power supply unit 10 of the second embodiment shown in FIG. 16, the lower limit value of the amplification range of the first operational amplifier 56 can be shifted in a negative direction by the rail splitter circuit 59. Therefore, in a state where the temperature of the load 21 is within the operating temperature range while the potential of the first connection node is less than the potential of the second connection node, the occurrence of the lower limit clip in the first operational amplifier 56 can be prevented in the operating temperature range by determining at least one of the electric resistance values of the resistors 591, 592 and the input voltage in such a manner that the differential input value of the first operational amplifier 56 is larger than the negative potential generated by the rail splitter circuit 59.

In a state where the temperature of the load 21 is within the operating temperature range while the potential of the first connection node is equal to or higher than the potential of the second connection node, the occurrence of the upper limit clip in the first operational amplifier 56 can be prevented in the operating temperature range by determining at least one of the electric resistance values of the resistors 591, 592 and the input voltage in such a manner that the differential input value of the first operational amplifier 56 is smaller than the positive potential generated by the rail splitter circuit 59.

Figure 17:
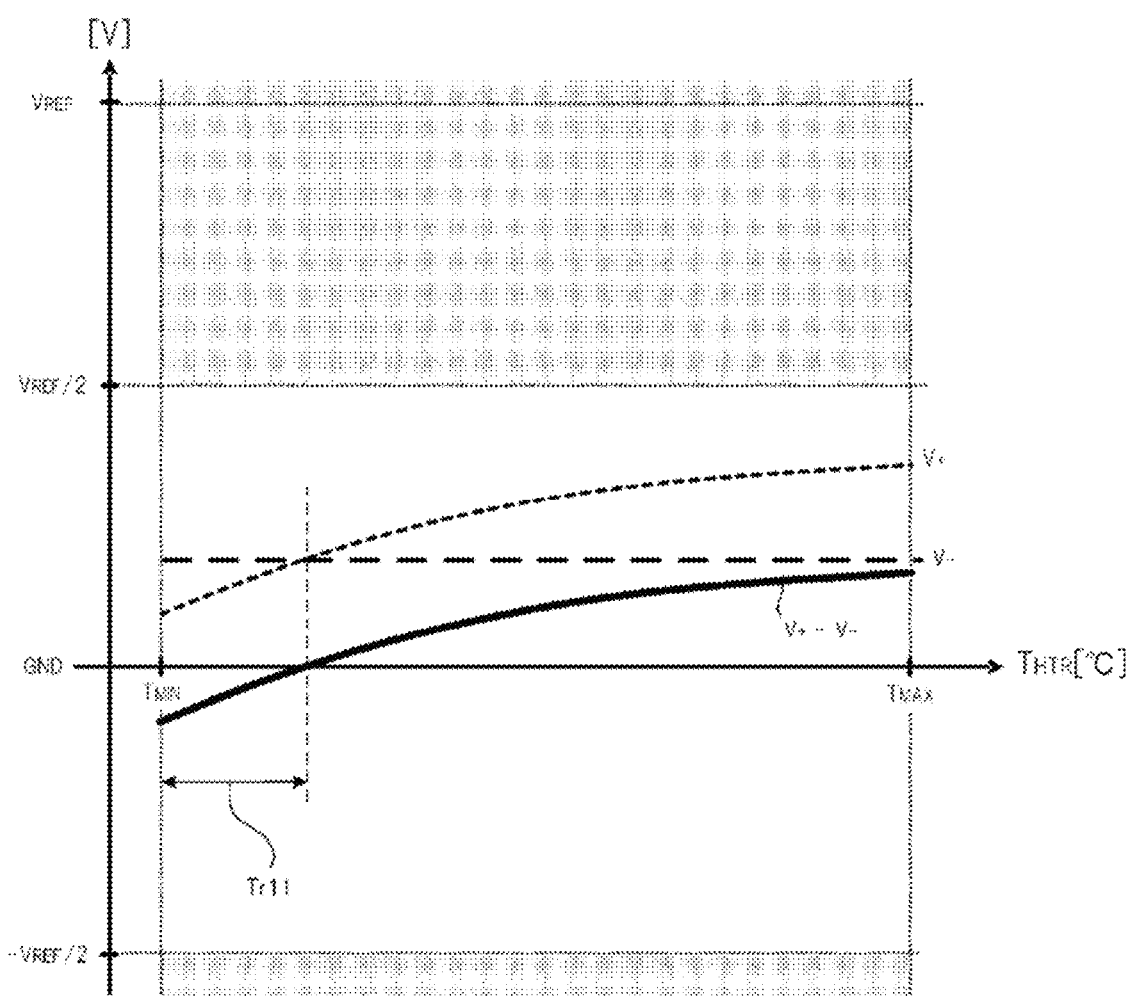
FIG. 17 is a graph showing an example of the differential input value of the first operational amplifier 56 in the power supply unit 10 of the second embodiment shown in FIG. 16.

FIG. 17 is a graph showing an example of the differential input value of the first operational amplifier 56 in the power supply unit 10 of the second embodiment shown in FIG. 16. In FIG. 17, and FIGS. 18, 20, 22 and 24 to be described below, the vertical axis represents the voltage (potential) while the horizontal axis represents the temperature of the load 21.

Figure 18:
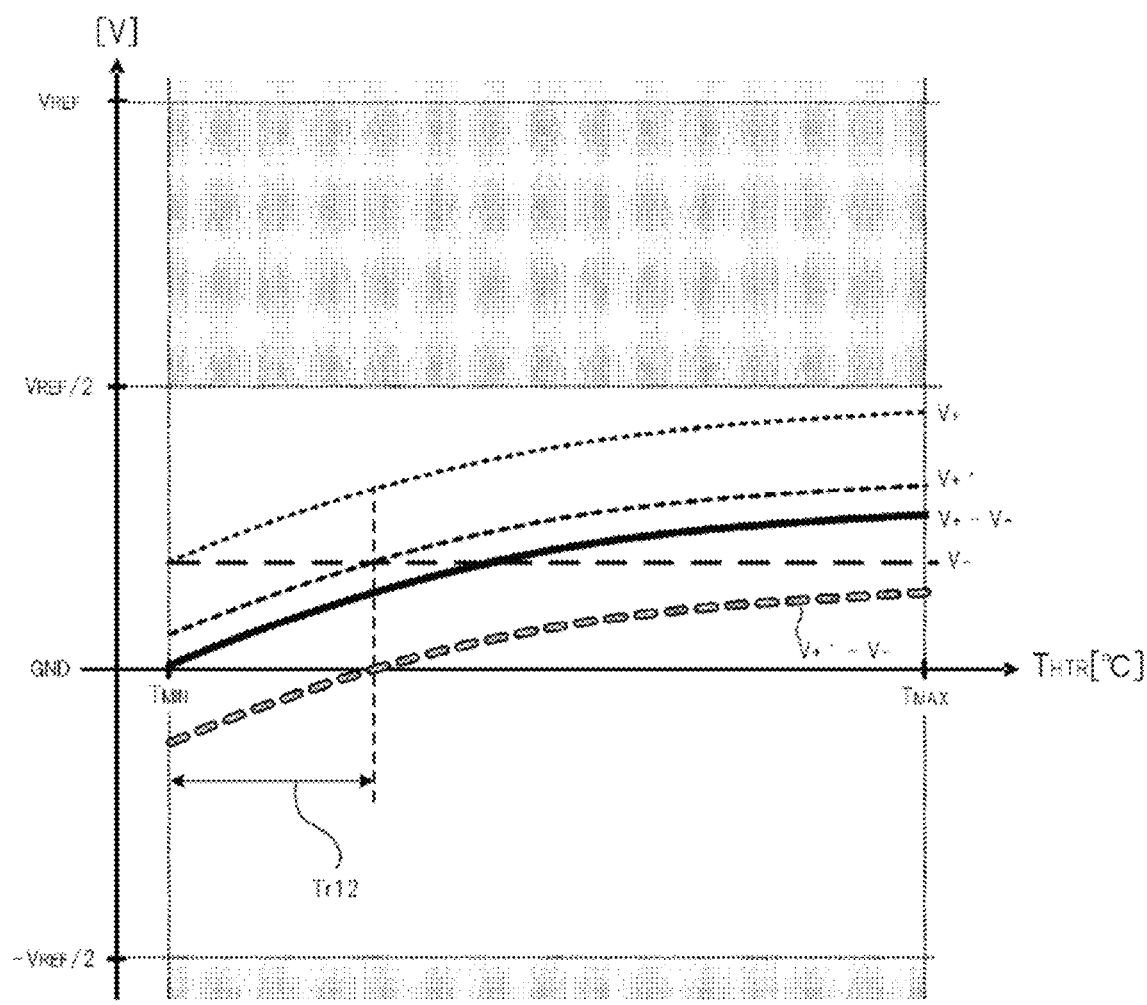
FIG. 18 is a graph showing another example of the differential input value of the first operational amplifier 56 in the power supply unit 10 of the second embodiment shown in FIG. 16.

In FIGS. 17 and 18, a graph denoted by "$V_+$" represents the potential of the first connection node between the first element 63 and the load 21. In FIGS. 17 and 18, a graph denoted by "$V_-$" represents the potential of the second connection node between the second element 64 and the third element 65. In FIG. 17, a graph denoted by "$V_+$-$V_-$" represents the differential input value of the first operational amplifier 56.

In the second embodiment shown in FIG. 16, in a temperature range Tr11 in the operating temperature range, the potential "$V_+$" of the first connection node is less than the potential "$V_-$" of the second connection node. In order to prevent the lower limit clip, in the temperature range Tr11, the value (absolute value) of the negative potential generated by the rail splitter circuit 59 may be determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier). In the second embodiment shown in FIG. 16, in a range excluding the temperature range Tr11 in the operating temperature range, the value (absolute value) of the positive potential generated by the rail splitter circuit 59 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier). By determining the values of the potentials generated by the rail splitter circuit 59 in this way, the occurrence of the lower limit clip and the upper limit clip in the first operational amplifier 56 is prevented in the operating temperature range. Therefore, the detection accuracy of the temperature of the load 21 can be improved.

According to the second embodiment shown in FIG. 16, a configuration in which the potential "$V_+$" of the first connection node is less than the potential "$V_-$" of the second connection node in the operating temperature range can be adopted as the bridge circuit. Therefore, the restrictions on the electric resistance values of each element of the bridge circuit can be relaxed, and the degree of freedom in design can be improved.

The state where the potential "$V_+$" of the first connection node is less than the potential "$V_-$" of the second connection node may be caused by the manufacturing error of the electric resistance value $R_{HTR}$ of the load 21. Therefore, the values of the potentials generated by the rail splitter circuit 59 are desirably designed in consideration of the manufacturing error of the electric resistance value $R_{HTR}$ of the load 21.

FIG. 18 is a graph showing another example of the differential input value of the first operational amplifier 56 in the power supply unit 10 of the second embodiment shown in FIG. 16. In the example shown in FIG. 18, it is assumed that the electric resistance value $R_{HTR}$ of the load 21 is designed in such a manner that the potential "$V_+$" of the first connection node and the potential "$V_-$" of the second connection node are equal in a state where the temperature of the load 21 is equal to the lower limit temperature $T_{MIN}$. In FIG. 18, a graph denoted by "$V_+$-$V_-$" represents the differential input value of the first operational amplifier 56 when there is no error in the electric resistance value $R_{HTR}$ of the load 21.

In FIG. 18, a graph denoted by "$V_+'$" indicates the potential of the first connection node when there is an error of −10% in the electric resistance value $R_{HTR}$ of the load 21 as compared with the design value. As described above, when there is an error of −10% in the electric resistance value $R_{HTR}$ of the load 21, the differential input value of the first operational amplifier 56 is as shown in a graph "$V_+'$-$V_-$" in FIG. 18.

In the example of FIG. 18, in a temperature range Tr12 in the operating temperature range, the potential "$V_+'$" of the first connection node is less than the potential "$V_-$" of the second connection node. In order to prevent the lower limit clip, in the temperature range Tr12, the value (absolute value) of the negative potential generated by the rail splitter circuit 59 may be determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier). In the example of FIG. 18, in a range excluding the temperature range Tr12 in the operating temperature range, the value (absolute value) of the positive potential generated by the rail splitter circuit 59 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

When there is an error of +10% in the electric resistance value $R_{HTR}$ of the load 21 as compared with the design value, the potential "$V_+'$" of the first connection node is not less than the potential "$V_-$" of the second connection node in the operating temperature range. Therefore, in a state where the temperature of the load 21 is within the operating temperature range while the potential "$V_+'$" of the first connection node is equal to or higher than the potential "$V_-$" of the second connection node, the values (absolute value) of the potentials generated by the rail splitter circuit 59 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

In this way, in the power supply unit 10 of the second embodiment, the value of the negative potential generated by the rail splitter circuit 59 is determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier) in a state where: 1. there is an error of −10% in the electric resistance value $R_{HTR}$ of the load 21, 2. the temperature of the load 21 is within the operating temperature range, and 3. the potential "$V_+$" of the first connection node is less than the potential "$V_-$" of the second connection node. In the power supply unit 10 of the second embodiment, the value of the negative potential generated by the rail splitter circuit 59 is determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier) in a state where: 1. there is an error of −10% in the electric resistance value $R_{HTR}$ of the load 21, 2. the temperature of the load 21 is within the operating temperature range, and 3. the potential "$V_+$" of the first connection node is equal to or higher than the potential "$V_-$" of the second connection node or a state where: 1. there is an error of +10% in the electric resistance value $R_{HTR}$ of the load 21, 2. the temperature of the load 21 is within the operating temperature range, and 3. the potential "$V_+$" of the first connection node is equal to or higher than the potential "$V_-$" of the second connection node.

As described above, by determining the values of the potentials generated by the rail splitter circuit 59 in consideration of the manufacturing error of the load 21, the differential input value of the first operational amplifier 56 is between the potential of the negative power supply terminal (or the minimum value) and the potential of the positive power supply terminal (or the maximum value) in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved.

(First Modification of Second Embodiment of Electric Circuit)

Figure 19:
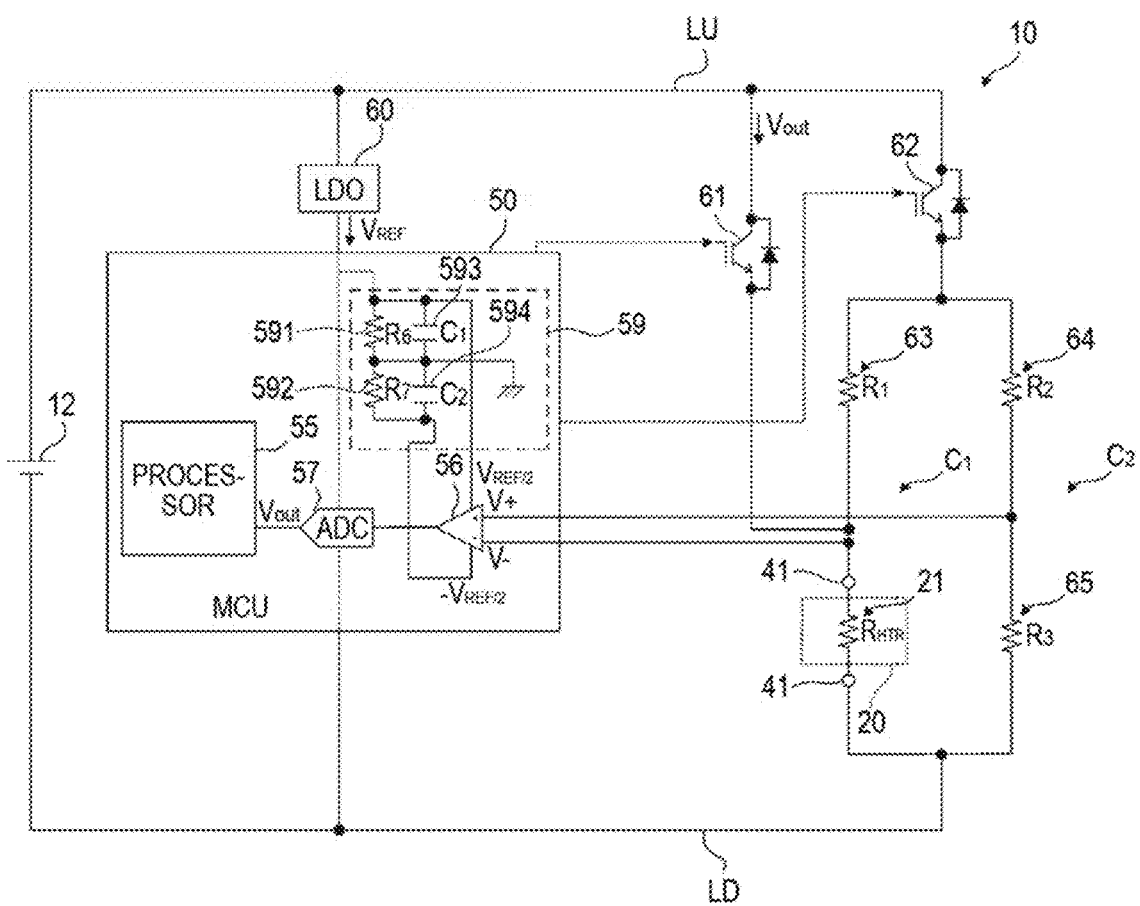
FIG. 19 is a schematic view showing a first modification of the circuit configuration of the power supply unit 10 of the second embodiment shown in FIG. 16.

FIG. 19 is a schematic view showing a first modification of the circuit configuration of the power supply unit 10 of the second embodiment shown in FIG. 16. The power supply unit 10 shown in FIG. 19 is the same as the circuit configuration of FIG. 16 except that a connection relationship between the first operational amplifier 56 and the bridge circuit is changed. In the power supply unit 10 shown in FIG. 19, the inversion input terminal of the first operational amplifier 56 is connected to the first connection node between the first element 63 and the load 21. The non-inversion input terminal of the first operational amplifier 56 is connected to the second connection node between the second element 64 and the third element 65.

Figure 20:
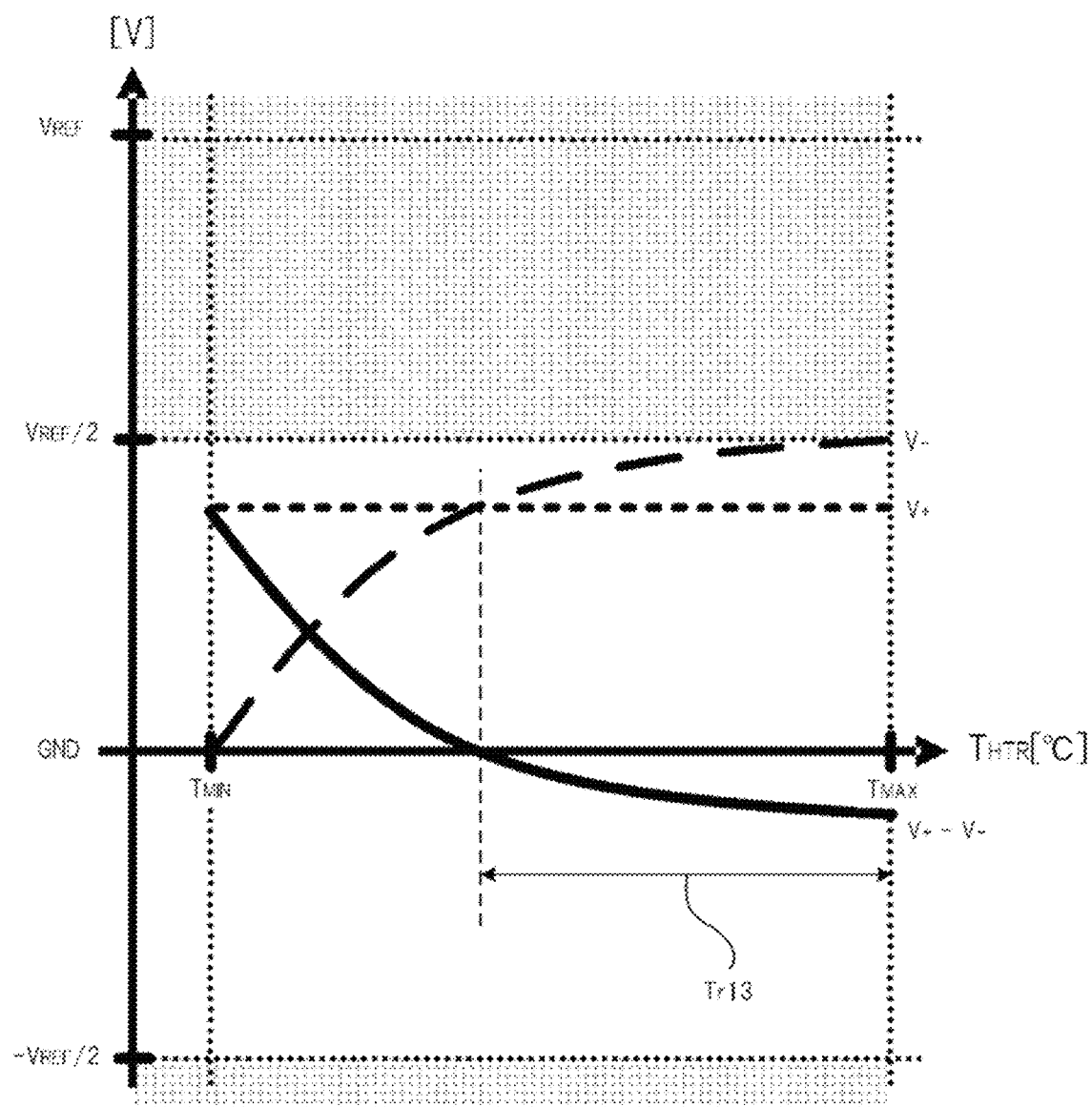
FIG. 20 is a graph showing an example of the differential input value of the first operational amplifier 56 in the power supply unit 10 shown in FIG. 19.

FIG. 20 is a graph showing an example of the differential input value of the first operational amplifier 56 in the power supply unit 10 shown in FIG. 19. In FIG. 20, a graph denoted by "$V_+$" represents the potential of the second connection node between the second element 64 and the third element 65. In FIG. 20, a graph denoted by "$V_-$" represents the potential of the first connection node between the first element 63 and the load 21. In FIG. 20, a graph denoted by "$V_+-V_-$" represents the differential input value of the first operational amplifier 56.

As an example, in the power supply unit 10 shown in FIG. 10, the electric resistance value $R_{HTR}$ of the load 21 is designed in such a manner that the potential "$V_+$" of the second connection node and the potential "$V_-$" of the first connection node are equal in the state where the temperature of the load 21 is equal to the upper limit temperature $T_{MAX}$. FIG. 20 shows an example in which there is an error of +10% in the electric resistance value $R_{HTR}$ of the load 21.

Since there is an error of +10% in the electric resistance value $R_{HTR}$ of the load 21, in the example shown in FIG. 20, the potential "$V_+$" of the first connection node is less than the potential "$V_-$" of the second connection node in a temperature range Tr13 in the operating temperature range. In order to prevent the lower limit clip, in the temperature range Tr13, the value (absolute value) of the negative potential generated by the rail splitter circuit 59 may be determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier). In the example of FIG. 20, in a range excluding the temperature range Tr13 in the operating temperature range, the value (absolute value) of the positive potential generated by the rail splitter circuit 59 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

When there is an error of −10% in the electric resistance value $R_{HTR}$ of the load 21 as compared with the design value, the potential "$V_+$" of the first connection node is not less than the potential "$V_-$" of the second connection node in the operating temperature range. Therefore, in a state where the temperature of the load 21 is within the operating temperature range while the potential "$V_+$" of the first connection node is equal to or higher than the potential "$V_-$" of the second connection node, the values (absolute value) of the potentials generated by the rail splitter circuit 59 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

In this way, in the power supply unit 10 of the first modification of the second embodiment, the value of the negative potential generated by the rail splitter circuit 59 is determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier) in a state where: 1. there is an error of +10% in the electric resistance value $R_{HTR}$ of the load 21, 2. the temperature of the load 21 is within the operating temperature range, and 3. the potential "$V_+$" of the second connection node is less than the potential "$V_-$" of the first connection node. In the power supply unit 10 of the first modification of the second embodiment, the value of the negative potential generated by the rail splitter circuit 59 is determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier) in a state where: 1. there is an error of +10% in the electric resistance value $R_{HTR}$ of the load 21, 2. the temperature of the load 21 is within the operating temperature range, and 3. the potential "$V_+$" of the second connection node is equal to or higher than the potential "$V_-$" of the first connection node or a state where: 1. there is an error of −10% in the electric resistance value $R_{HTR}$ of the load 21, 2. the temperature of the load 21 is within the operating temperature range, and 3. the potential "$V_+$" of the second connection node is equal to or higher than the potential "$V_-$" of the first connection node.

As described above, by determining the values of the potentials generated by the rail splitter circuit 59 in consideration of the manufacturing error of the load 21, the differential input value of the first operational amplifier 56 is between the potential of the negative power supply terminal (or the minimum value) and the potential of the positive power supply terminal (or the maximum value) in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved.

(Second Modification of Second Embodiment of Electric Circuit)

Figure 21:
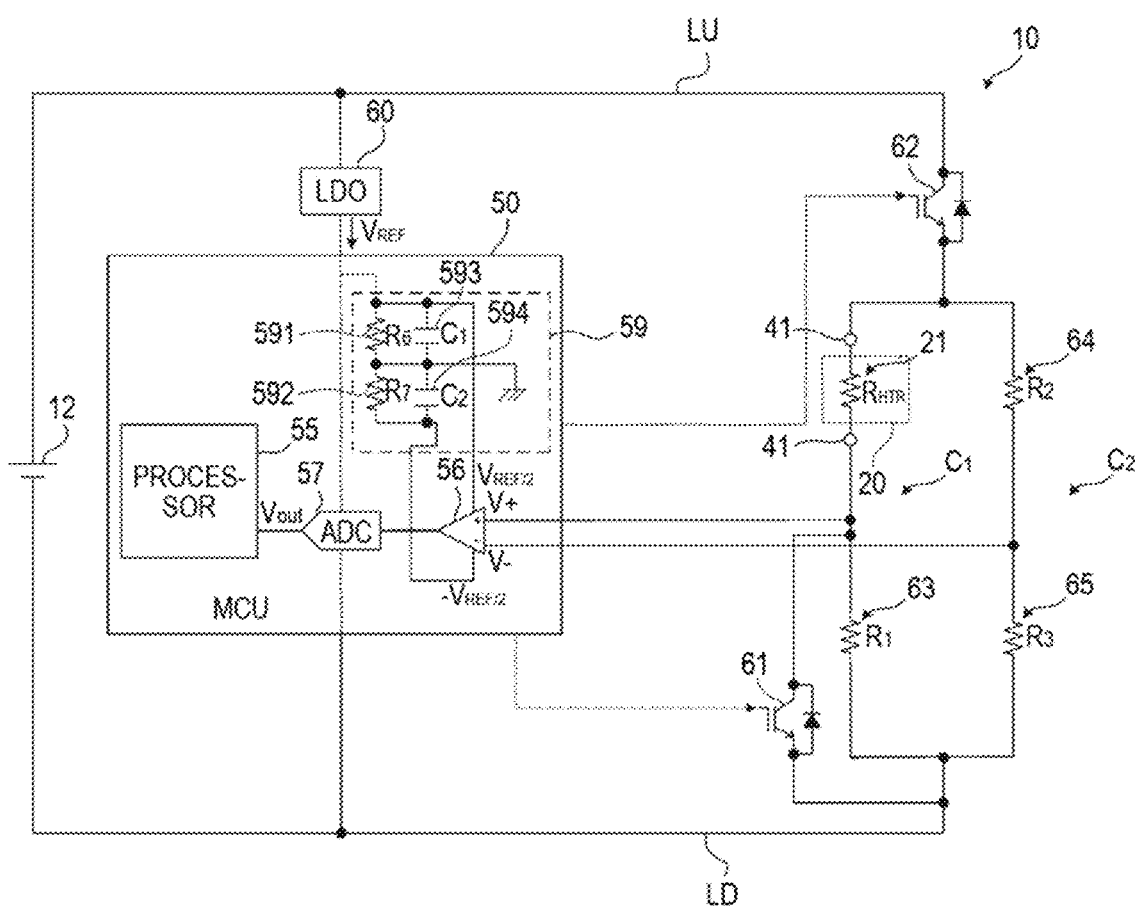
FIG. 21 is a schematic view showing a second modification of the circuit configuration of the power supply unit 10 of the second embodiment shown in FIG. 16.

FIG. 21 is a schematic view showing a second modification of the circuit configuration of the power supply unit 10 of the second embodiment shown in FIG. 16. The power supply unit 10 shown in FIG. 21 is the same as the circuit configuration of FIG. 16 except that the positions of the first element 63 and the load 21 are reversed in the first series circuit C1 while the position of the switch 61 is changed.

The switch 61 is connected between the first connection node and the main negative bus LD. In the power supply unit 10 shown in FIG. 21, the load 21 is heated when the switch 61 and the switch 62 are both turned on. The temperature of the load 21 is detected when the switch 61 is turned off while the switch 62 is turned on.

Figure 22:
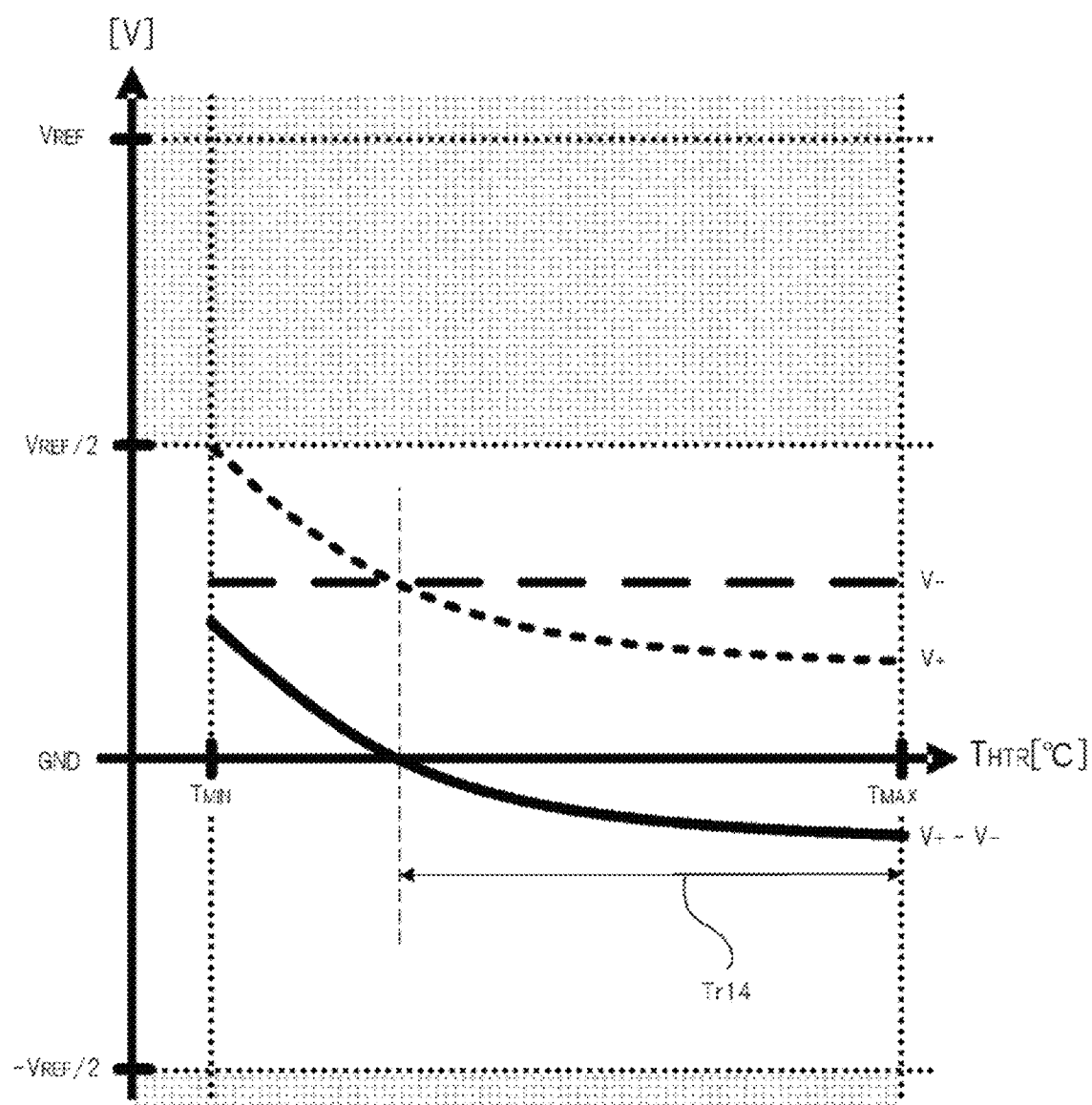
FIG. 22 is a graph showing an example of the differential input value of the first operational amplifier 56 in the power supply unit 10 shown in FIG. 21.

FIG. 22 is a graph showing an example of the differential input value of the first operational amplifier 56 in the power supply unit 10 shown in FIG. 21. In FIG. 22, a graph denoted by "$V_+$" represents the potential of the first connection node between the first element 63 and the load 21. In FIG. 22, a graph denoted by "$V_-$" represents the potential of the second connection node between the second element 64 and the third element 65. In FIG. 22, a graph denoted by "$V_+-V_-$" represents the differential input value of the first operational amplifier 56.

As an example, in the power supply unit 10 shown in FIG. 21, the electric resistance value $R_{HTR}$ of the load 21 is designed in such a manner that the potential "$V_+$" of the first connection node and the potential "$V_-$" of the second connection node are equal in a state where the temperature of the load 21 is equal to the upper limit temperature $T_{MAX}$. FIG. 22 shows an example in which there is an error of −10% in the electric resistance value $R_{HTR}$ of the load 21.

Since there is an error of −10% in the electric resistance value $R_{HTR}$ of the load 21, in the example shown in FIG. 22, the potential "$V_+$" of the first connection node is less than the potential "$V_-$" of the second connection node in a temperature range Tr14 in the operating temperature range. In order to prevent the lower limit clip, in the temperature range Tr14, the value (absolute value) of the negative potential generated by the rail splitter circuit 59 may be determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier). In the example of FIG. 22, in a range excluding the temperature range Tr14 in the operating temperature range, the value (absolute value) of the positive potential generated by the rail splitter circuit 59 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

When there is an error of +10% in the electric resistance value $R_{HTR}$ of the load 21 as compared with the design value, the potential "$V_+$" of the first connection node is not less than the potential "$V_-$" of the second connection node in the operating temperature range. Therefore, in a state where the temperature of the load 21 is within the operating temperature range while the potential "$V_+$" of the first connection node is equal to or higher than the potential "$V_-$" of the second connection node, the values (absolute value) of the potentials generated by the rail splitter circuit 59 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

In this way, in the power supply unit 10 of the second modification of the second embodiment, the value of the negative potential generated by the rail splitter circuit 59 is determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier) in the state where: 1. there is an error of −10% in the electric resistance value $R_{HTR}$ of the load 21, 2. the temperature of the load 21 is within the operating temperature range, and 3. the potential "$V_+$" of the first connection node is less than the potential "$V_-$" of the second connection node. In the power supply unit 10 of the second modification of the second embodiment, the value of the negative potential generated by the rail splitter circuit 59 is determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier) in the state where: 1. there is an error of −10% in the electric resistance value $R_{HTR}$ of the load 21, 2. the temperature of the load 21 is within the operating temperature range, and 3. the potential "$V_+$" of the first connection node is equal to or higher than the potential "$V_-$" of the second connection node or the state where: 1. there is an error of +10% in the electric resistance value $R_{HTR}$ of the load 21, 2. the temperature of the load 21 is within the operating temperature range, and 3. the potential "$V_+$" of the first connection node is equal to or higher than the potential "$V_-$" of the second connection node.

As described above, by determining the values of the potentials generated by the rail splitter circuit 59 in consideration of the manufacturing error of the load 21, the differential input value of the first operational amplifier 56 is between the potential of the negative power supply terminal (or the minimum value) and the potential of the positive power supply terminal (or the maximum value) in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved.

(Third Modification of Second Embodiment of Electric Circuit)

Figure 23:
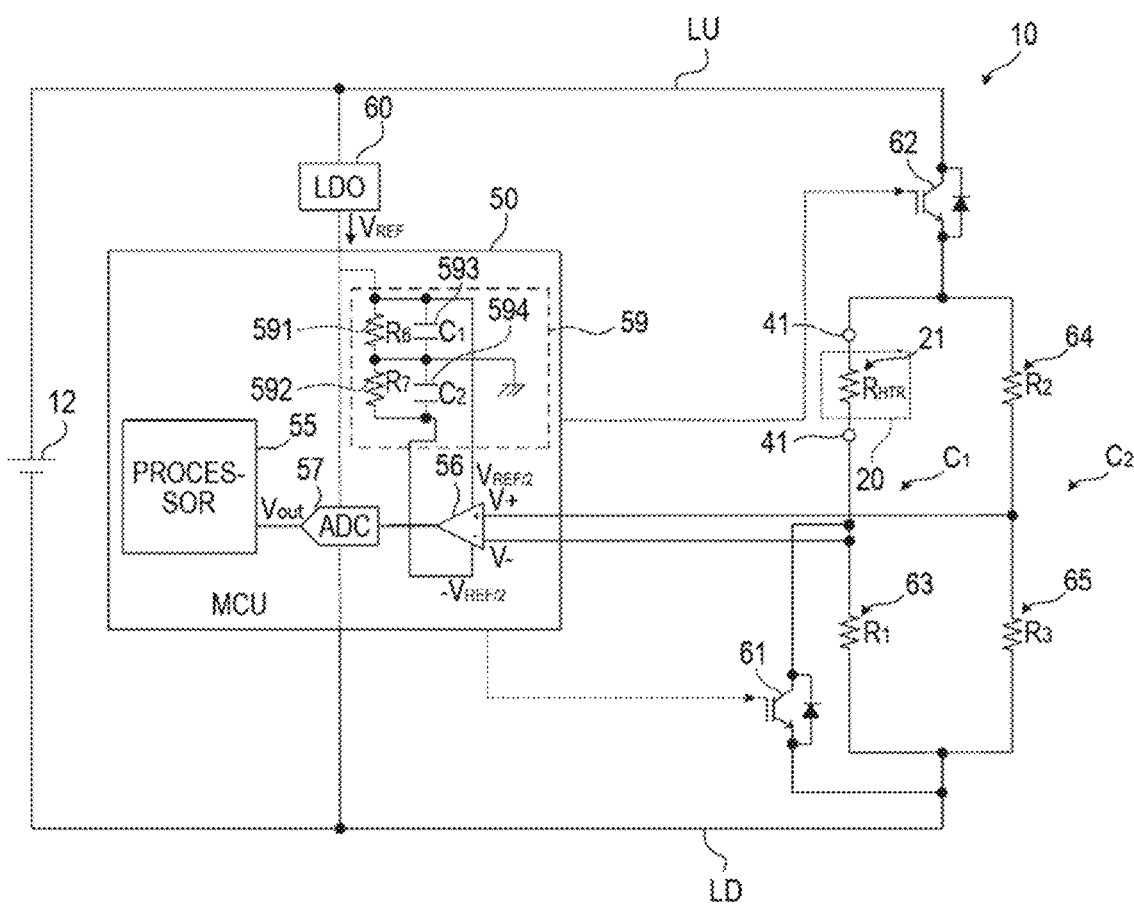
FIG. 23 is a schematic view showing a third modification of the circuit configuration of the power supply unit of the second embodiment shown in FIG. 16.

FIG. 23 is a schematic view showing a third modification of the circuit configuration of the power supply unit of the second embodiment shown in FIG. 16. The power supply unit 10 shown in FIG. 23 is the same as the circuit configuration of FIG. 21 except that the connection relationship between the first operational amplifier 56 and the bridge circuit is changed. In the power supply unit 10 shown in FIG. 23, the inversion input terminal of the first operational amplifier 56 is connected to the first connection node between the first element 63 and the load 21. The non-inversion input terminal of the first operational amplifier 56 is connected to the second connection node between the second element 64 and the third element 65.

Figure 24:
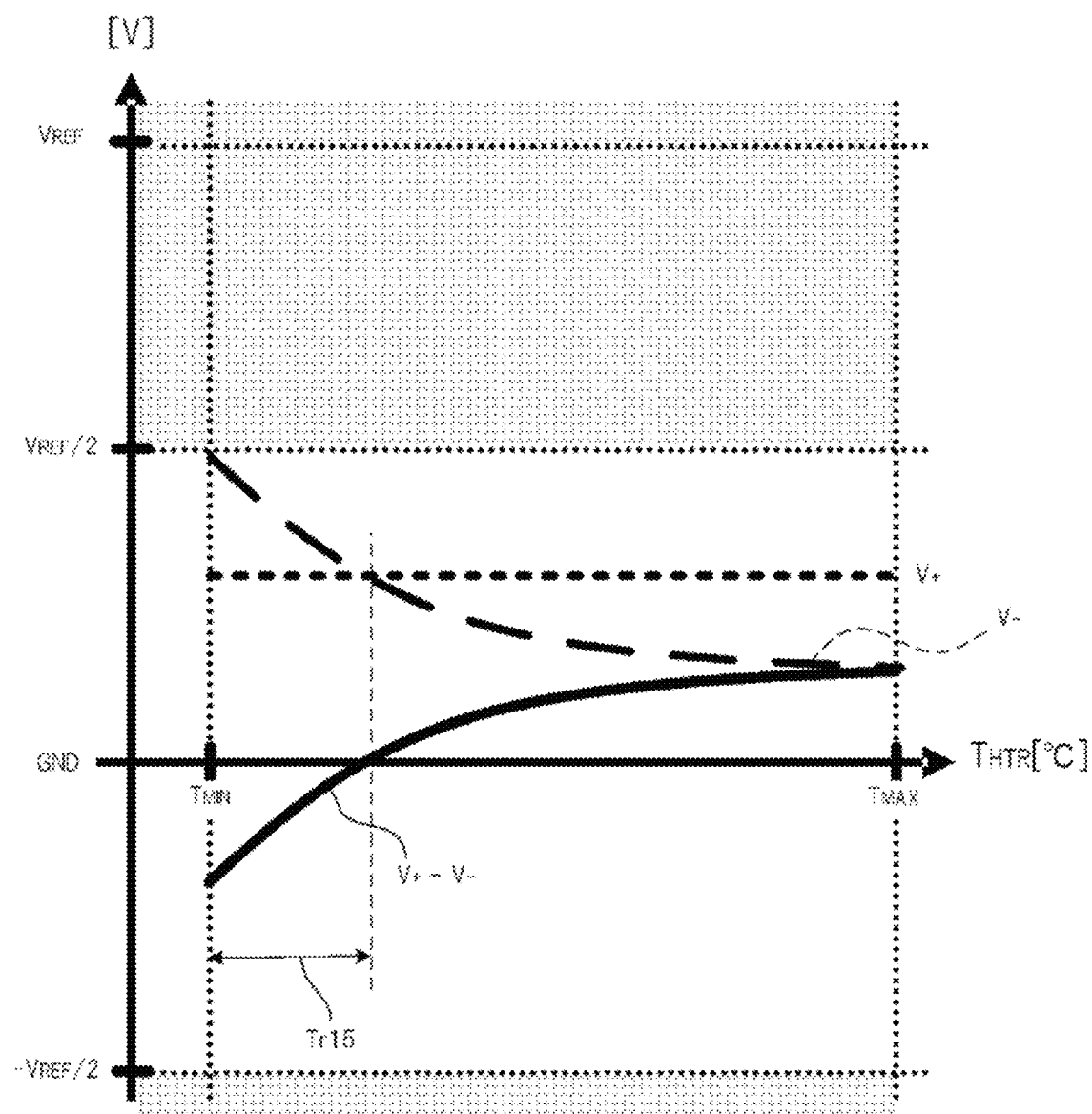
FIG. 24 is a graph showing an example of the differential input value of the first operational amplifier 56 in the power supply unit 10 shown in FIG. 23.

FIG. 24 is a graph showing an example of the differential input value of the first operational amplifier 56 in the power supply unit 10 shown in FIG. 23. In FIG. 24, a graph denoted by "$V_+$" represents the potential of the second connection node between the second element 64 and the third element 65. In FIG. 24, a graph denoted by "$V_-$" represents the potential of the first connection node between the first element 63 and the load 21. In FIG. 24, a graph denoted by "$V_+ - V_-$" represents the differential input value of the first operational amplifier 56.

As an example, in the power supply unit 10 shown in FIG. 23, the electric resistance value $R_{HTR}$ of the load 21 is designed in such a manner that the potential "$V_+$" of the second connection node and the potential "$V_-$" of the first connection node are equal in the state where the temperature of the load 21 is equal to the lower limit temperature $T_{MIN}$. FIG. 24 shows an example in which there is an error of +10% in the electric resistance value $R_{HTR}$ of the load 21.

Since there is an error of +10% in the electric resistance value $R_{HTR}$ of the load 21, in the example shown in FIG. 24, the potential "$V_+$" of the second connection node is less than the potential "$V_-$" of the first connection node in a temperature range Tr15 in the operating temperature range. In order to prevent the lower limit clip, in the temperature range Tr15, the value (absolute value) of the negative potential generated by the rail splitter circuit 59 may be determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier). In the example of FIG. 24, in a range excluding the temperature range Tr15 in the operating temperature range, the value (absolute value) of the positive potential generated by the rail splitter circuit 59 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

When there is an error of −10% in the electric resistance value $R_{HTR}$ of the load 21 as compared with the design value, the potential "$V_+$" of the second connection node is not less than the potential "$V_-$" of the first connection node in the operating temperature range. Therefore, in the state where the temperature of the load 21 is within the operating temperature range while the potential "$V_+$" of the second connection node is equal to or higher than the potential "$V_-$" of the first connection node, the values (absolute value) of the potentials generated by the rail splitter circuit 59 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

In this way, in the power supply unit 10 of the third modification of the second embodiment, the value of the negative potential generated by the rail splitter circuit 59 is determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier) in the state where: 1. there is an error of +10% in the electric resistance value $R_{HTR}$ of the load 21, 2. the temperature of the load 21 is within the operating temperature range, and 3. the potential "$V_+$" of the second connection node is less than the potential "$V_-$" of the first connection node. In the power supply unit 10 of the third modification of the second embodiment, the value of the negative potential generated by the rail splitter circuit 59 is determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier) in the state where: 1. there is an error of +10% in the electric resistance value $R_{HTR}$ of the load 21, 2. the temperature of the load 21 is within the operating temperature range, and 3. the potential "$V_+$" of the second connection node is equal to or higher than the potential "$V_-$" of the first connection node in the state where: 1. there is an error of −10% in the electric resistance value $R_{HTR}$ of the load 21, 2. the temperature of the load 21 is within the operating temperature range, and 3. the potential "$V_+$" of the second connection node is equal to or higher than the potential "$V_-$" of the first connection node.

As described above, by determining the values of the potentials generated by the rail splitter circuit 59 in consideration of the manufacturing error of the load 21, the differential input value of the first operational amplifier 56 is between the potential of the negative power supply terminal (or the minimum value) and the potential of the positive power supply terminal (or the maximum value) in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved. As described above, when the first operational amplifier 56 is not the input-output rail-to-rail type operational amplifier, the values (absolute value) of the potentials generated by the rail splitter circuit 59 may be determined in such a manner that the differential input value is between the maximum value and the minimum value that can be acquired by the first operational amplifier 56.

(Third Embodiment of Electric Circuit)

Figure 25:
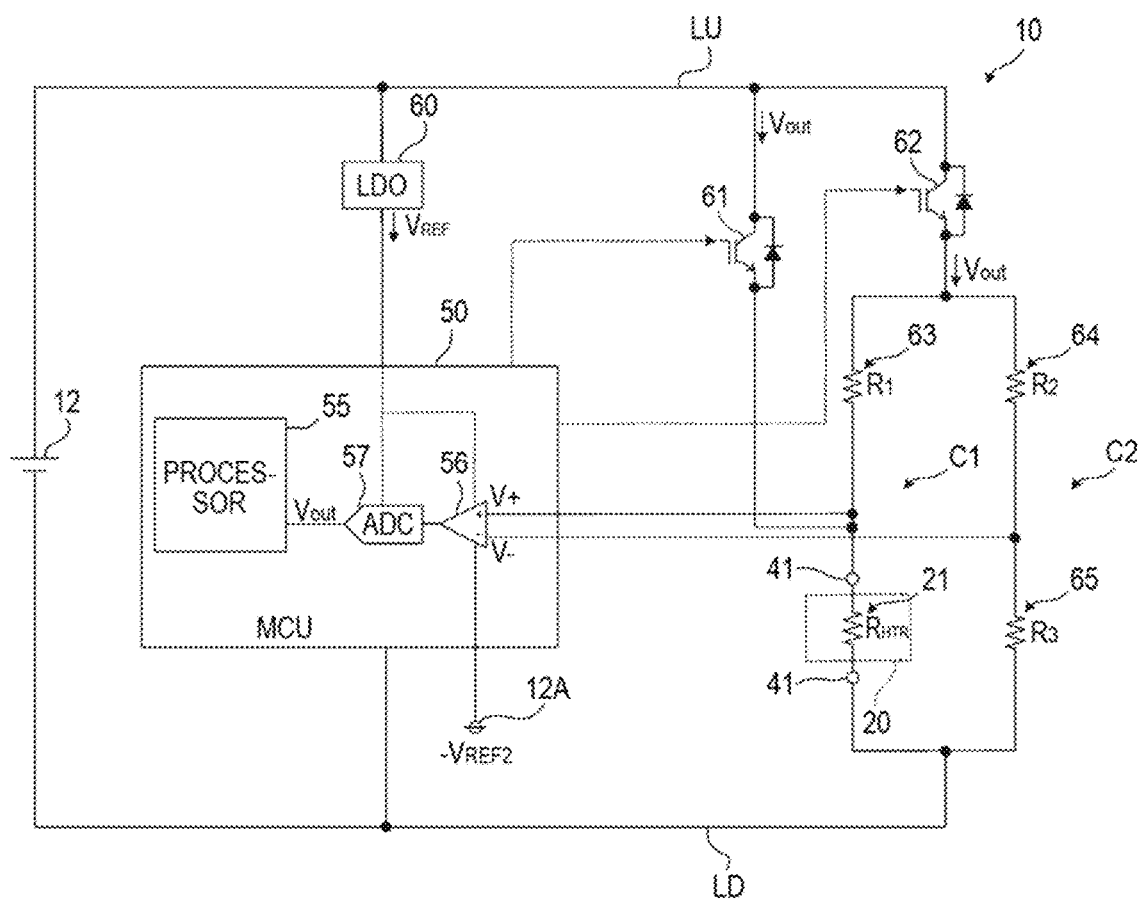
FIG. 25 is a schematic diagram showing a third embodiment of the circuit configuration of the power supply unit of the aerosol inhaler shown in FIG. 1.

FIG. 25 is a schematic diagram showing a third embodiment of the circuit configuration of the power supply unit of the aerosol inhaler shown in FIG. 1. The power supply unit 10 shown in FIG. 25 has the same configuration as that of FIG. 6 except that the inversion input terminal of the first operational amplifier 56 is directly connected to the second connection node between the second element 64 and the third element 65 while a negative power supply 12A that supplies a negative potential ("$-V_{REF2}$" whose absolute value is smaller than the reference voltage in the example of FIG. 25) is connected to the negative power supply terminal of the first operational amplifier 56.

According to the power supply unit 10 of the third embodiment shown in FIG. 25, the lower limit value of the amplification range of the first operational amplifier 56 can be extended in the negative direction by the negative power supply 12A. Therefore, in a state where the temperature of the load 21 is within the operating temperature range while the potential of the first connection node is less than the potential of the second connection node, the occurrence of the lower limit clip in the first operational amplifier 56 can be prevented in the operating temperature range by determining the potential supplied from the negative power supply 12A in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier).

Figure 26:
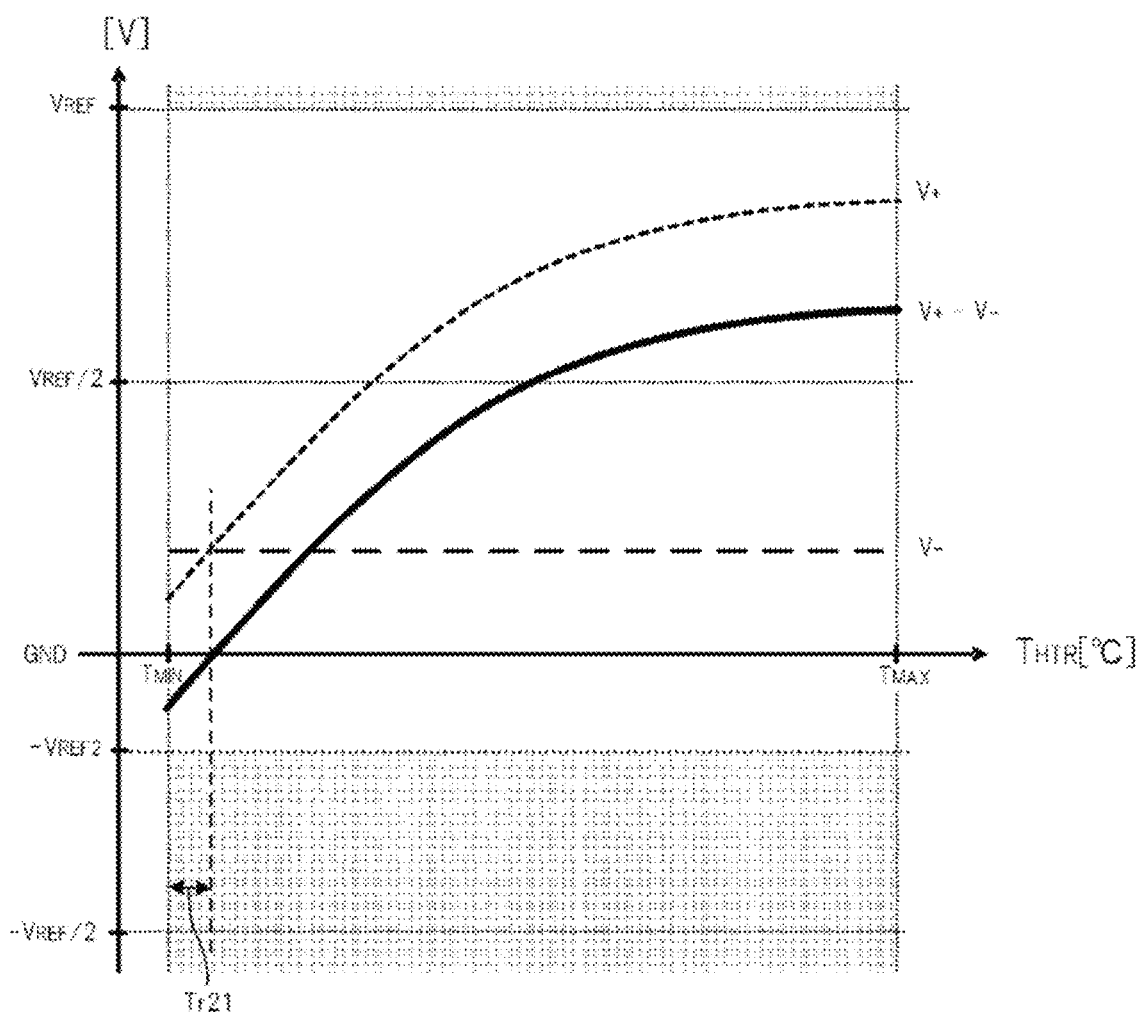
FIG. 26 is a graph showing an example of the differential input value of the first operational amplifier 56 in the power supply unit 10 of the third embodiment shown in FIG. 25.

FIG. 26 is a graph showing an example of the differential input value of the first operational amplifier 56 in the power supply unit 10 of the third embodiment shown in FIG. 25. In FIG. 26, and FIGS. 27, 29, 31 and 33 to be described below, the vertical axis represents the voltage (potential) while the horizontal axis represents the temperature of the load 21.

Figure 27:
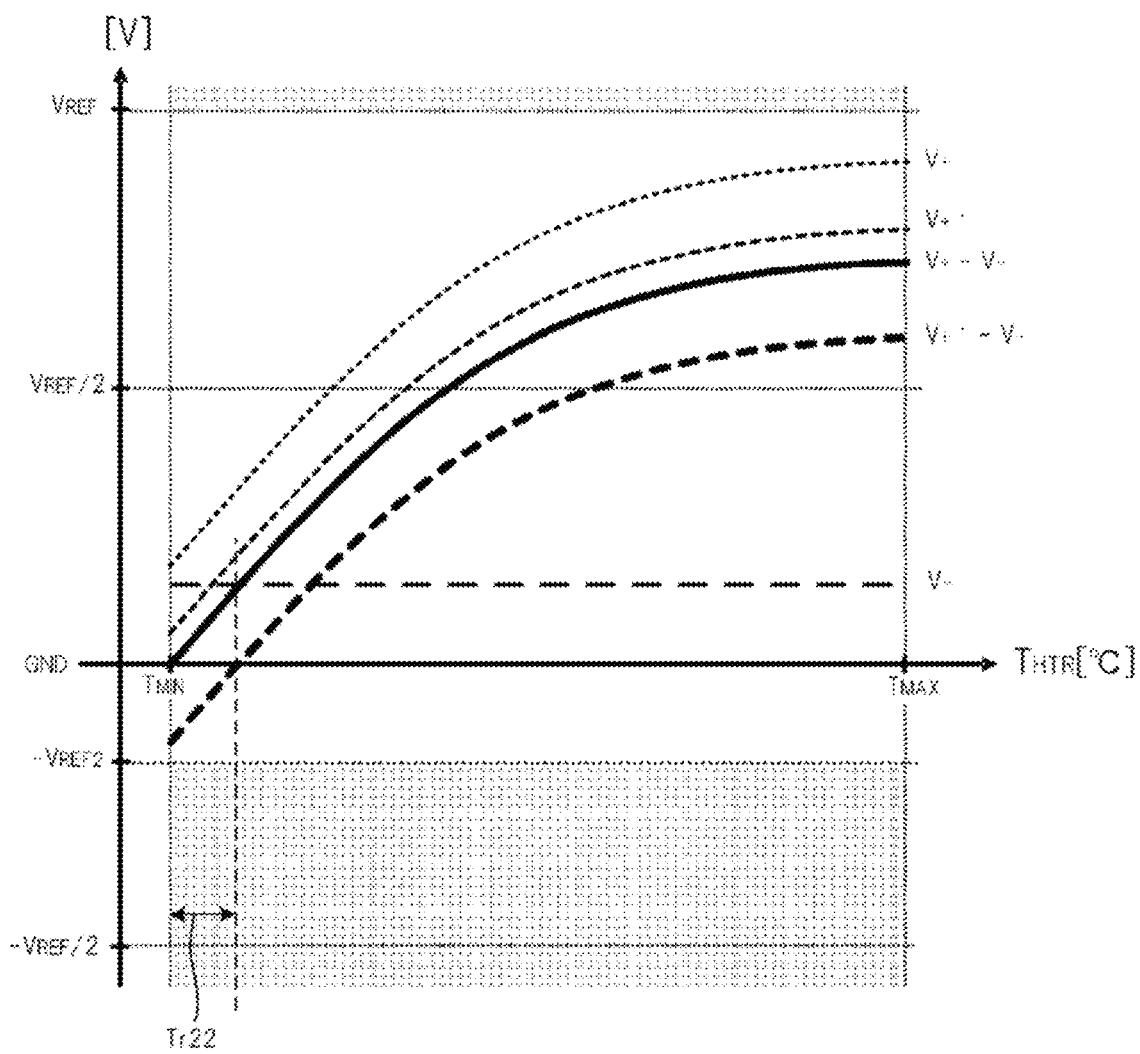
FIG. 27 is a graph showing another example of the differential input value of the first operational amplifier 56 in the power supply unit 10 of the third embodiment shown in FIG. 25.

In FIGS. 26 and 27, a graph denoted by "$V_+$" represents the potential of the first connection node between the first element 63 and the load 21. In FIGS. 26 and 27, a graph denoted by "$V_-$" represents the potential of the second connection node between the second element 64 and the third element 65. In FIG. 26, a graph denoted by "$V_+−V_-$" represents the differential input value of the first operational amplifier 56.

In the third embodiment shown in FIG. 25, in a temperature range Tr21 in the operating temperature range, the potential "$V_+$" of the first connection node is less than the potential "$V_-$" of the second connection node. In order to prevent the lower limit clip, in the temperature range Tr21, the potential of the negative power supply 12A may be determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier). In the third embodiment shown in FIG. 25, in a range excluding the temperature range Tr21 in the operating temperature range, the potential of the positive power supply terminal may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier). By determining the values of the potentials of the positive power supply terminal and the negative power supply terminal in this way, the occurrence of the lower limit clip and the upper limit clip in the first operational amplifier 56 is prevented in the operating temperature range. Therefore, the detection accuracy of the temperature of the load 21 can be improved.

According to the third embodiment shown in FIG. 25, the configuration in which the potential "$V_+$" of the first connection node is less than the potential "$V_-$" of the second connection node in the operating temperature range can be adopted as the bridge circuit. Therefore, the restrictions on the electric resistance values of each element of the bridge circuit can be relaxed, and the degree of freedom in design can be improved. A degree of freedom in setting the potential of the positive power supply terminal of the first operational amplifier 56 can also be improved.

The state where the potential "$V_+$" of the first connection node is less than the potential "$V_-$" of the second connection node may be caused by the manufacturing error of the electric resistance value $R_{HTR}$ of the load 21. Therefore, the value of the potential of the negative power supply 12A is desirably designed in consideration of the manufacturing error of the electric resistance value $R_{HTR}$ of the load 21.

FIG. 27 is a graph showing another example of the differential input value of the first operational amplifier 56 in the power supply unit 10 of the third embodiment shown in FIG. 25. In the example shown in FIG. 27, it is assumed that the electric resistance value $R_{HTR}$ of the load 21 is designed in such a manner that the potential "$V_+$" of the first connection node and the potential "$V_-$" of the second connection node are equal in the state where the temperature of the load 21 is equal to the lower limit temperature $T_{MIN}$. In FIG. 27, a graph denoted by "$V_+-V_-$" represents the differential input value of the first operational amplifier 56 when there is no error in the electric resistance value $R_{HTR}$ of the load 21.

In FIG. 27, a graph denoted by "$V_+'$" indicates the potential of the first connection node when there is an error of −10% in the electric resistance value $R_{HTR}$ of the load 21 as compared with the design value. As described above, when there is an error of −10% in the electric resistance value $R_{HTR}$ of the load 21, the differential input value of the first operational amplifier 56 is as shown in a graph "$V_+'-V_-$" in FIG. 27.

In the example of FIG. 27, in a temperature range Tr22 in the operating temperature range, the potential "$V_+'$" of the first connection node is less than the potential "$V_-$" of the second connection node. In order to prevent the lower limit clip, in the temperature range Tr22, the potential of the negative power supply 12A may be determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier). In the example of FIG. 27, in a range excluding the temperature range Tr22 in the operating temperature range, the potential of the positive power supply terminal may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

When there is an error of +10% in the electric resistance value $R_{HTR}$ of the load 21 as compared with the design value, the potential "$V_+'$" of the first connection node is not less than the potential "$V_-$" of the second connection node in the operating temperature range. Therefore, in the state where the temperature of the load 21 is within the operating temperature range while the potential "$V_+$" of the first connection node is equal to or higher than the potential "$V_-$" of the second connection node, the potential of the positive power supply terminal may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

In this way, in the power supply unit 10 of the third embodiment, the value of the potential of the negative power supply 12A is determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier) in a state where: 1. there is an error of −10% in the electric resistance value $R_{HTR}$ of the load 21, 2. the temperature of the load 21 is within the operating temperature range, and 3. the potential "$V_+$" of the first connection node is less than the potential "$V_-$" of the second connection node. In the power supply unit 10 of the third embodiment, the potential of the positive power supply terminal of the first operational amplifier 56 is determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier) in the state where: 1. there is an error of −10% in the electric resistance value $R_{HTR}$ of the load 21, 2. the temperature of the load 21 is within the operating temperature range, and 3. the potential "$V_+$" of the first connection node is equal to or higher than the potential "$V_-$" of the second connection node or the state where: 1. there is an error of +10% in the electric resistance value $R_{HTR}$ of the load 21, 2. the temperature of the load 21 is within the operating temperature range, and 3. the potential "$V_+$" of the first connection node is equal to or higher than the potential "$V_-$" of the second connection node.

As described above, by determining the values of the potentials of the positive power supply terminal and the negative power supply terminal of the first operational amplifier 56 in consideration of the manufacturing error of the load 21, the differential input value of the first operational amplifier 56 is between the potential of the negative power supply terminal and the potential of the positive power supply terminal in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved.

(First Modification of Third Embodiment of Electric Circuit)

Figure 28:
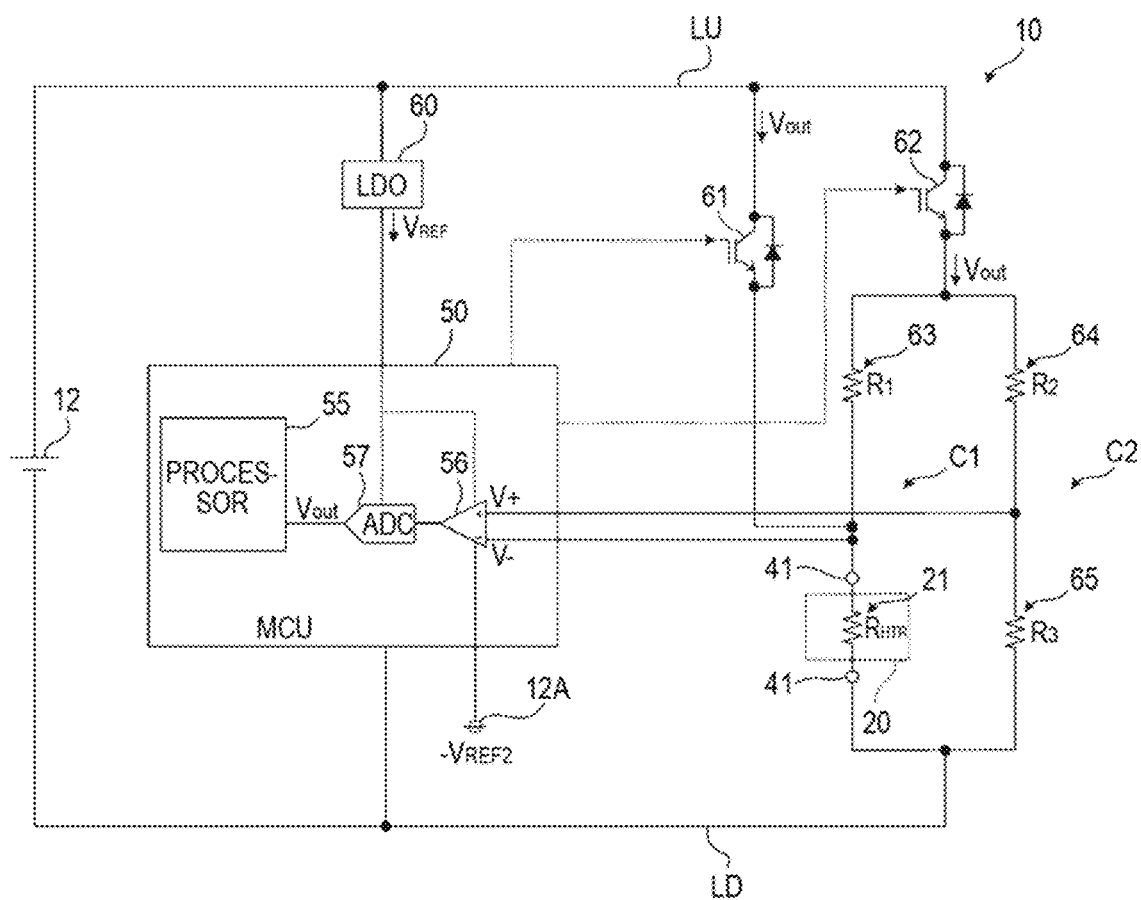
FIG. 28 is a schematic view showing a first modification of the circuit configuration of the power supply unit 10 of the third embodiment shown in FIG. 25.

FIG. 28 is a schematic view showing a first modification of the circuit configuration of the power supply unit 10 of the third embodiment shown in FIG. 25. The power supply unit 10 shown in FIG. 28 is the same as the circuit configuration of FIG. 25 except that the connection relationship between the first operational amplifier 56 and the bridge circuit is changed. In the power supply unit 10 shown in FIG. 28, the inversion input terminal of the first operational amplifier 56 is connected to the first connection node between the first element 63 and the load 21. The non-inversion input terminal of the first operational amplifier 56 is connected to the second connection node between the second element 64 and the third element 65.

Figure 29:
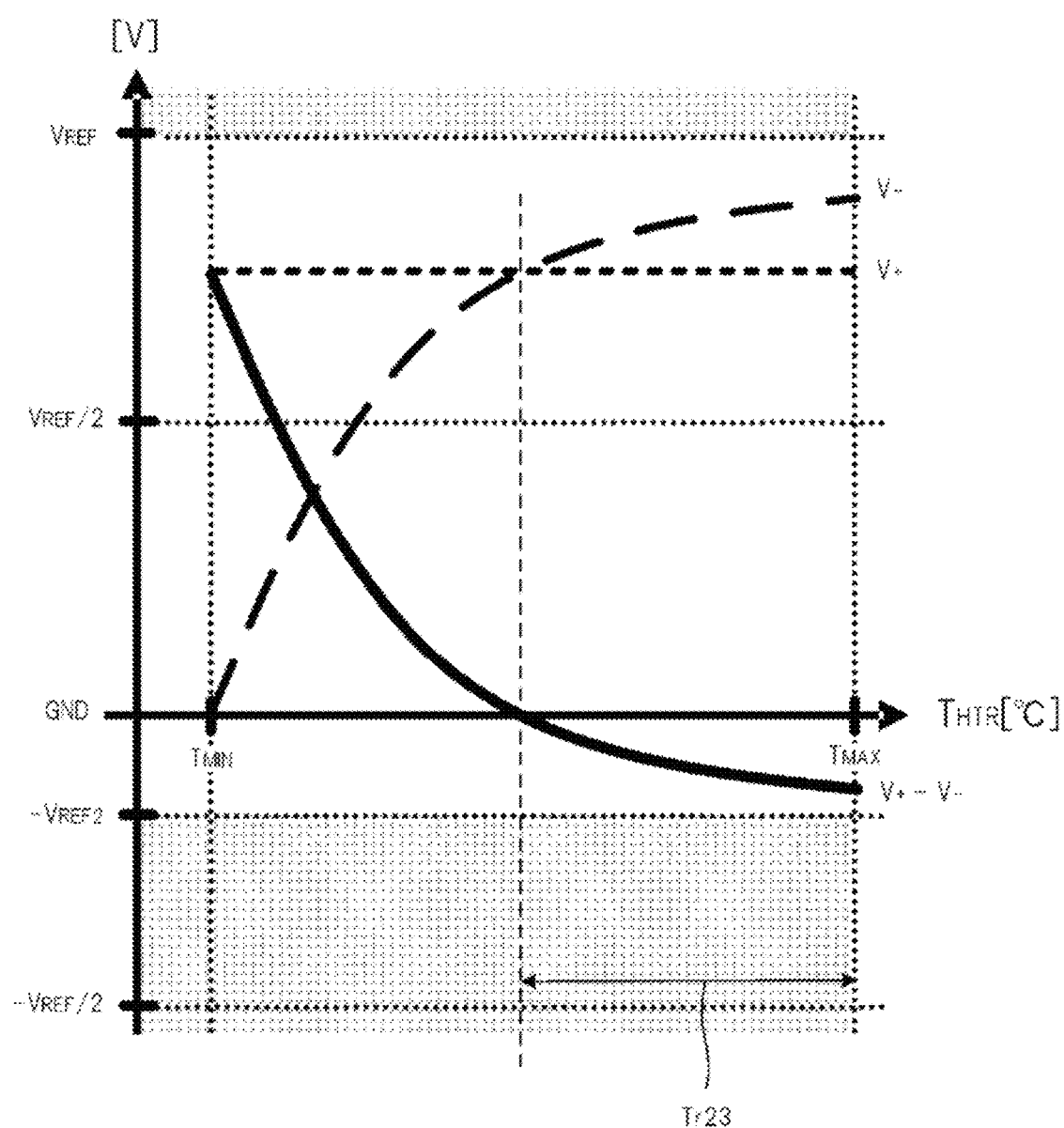
FIG. 29 is a graph showing an example of the differential input value of the first operational amplifier 56 in the power supply unit 10 shown in FIG. 28.

FIG. 29 is a graph showing an example of the differential input value of the first operational amplifier 56 in the power supply unit 10 shown in FIG. 28. In FIG. 29, a graph denoted by "$V_+$" represents the potential of the second connection node between the second element 64 and the third element 65. In FIG. 29, a graph denoted by "$V_-$" represents the potential of the first connection node between the first element 63 and the load 21. In FIG. 29, a graph denoted by "$V_+ - V_-$" represents the differential input value of the first operational amplifier 56.

As an example, in the power supply unit 10 shown in FIG. 28, the electric resistance value $R_{HTR}$ of the load 21 is designed in such a manner that the potential "$V_+$" of the second connection node and the potential "$V_-$" of the first connection node are equal in the state where the temperature of the load 21 is equal to the upper limit temperature $T_{MAX}$. FIG. 29 shows an example in which there is an error of +10% in the electric resistance value $R_{HTR}$ of the load 21.

Since there is an error of +10% in the electric resistance value $R_{HTR}$ of the load 21, in the example shown in FIG. 29, the potential "$V_+$" of the first connection node is less than the potential "$V_-$" of the second connection node in a temperature range Tr23 in the operating temperature range. In order to prevent the lower limit clip, in the temperature range Tr23, the potential of the negative power supply 12A may be determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier). In the example of FIG. 29, in a range excluding the temperature range Tr23 in the operating temperature range, the potential of the positive power supply terminal of the first operational amplifier 56 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

When there is an error of −10% in the electric resistance value $R_{HTR}$ of the load 21 as compared with the design value, the potential "$V_+$" of the first connection node is not less than the potential "$V_-$" of the second connection node in the operating temperature range. Therefore, in the state where the temperature of the load 21 is within the operating temperature range while the potential "$V_+$" of the first connection node is equal to or higher than the potential "$V_-$" of the second connection node, the potential of the positive power supply terminal of the first operational amplifier 56 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

In this way, in the power supply unit 10 of the first modification of the third embodiment, the value of the potential of the negative power supply 12A is determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier) in the state where: 1. there is an error of +10% in the electric resistance value $R_{HTR}$ of the load 21, 2. the temperature of the load 21 is within the operating temperature range, and 3. the potential "$V_+$" of the second connection node is less than the potential "$V_-$" of the first connection node. In the power supply unit 10 of the first modification of the third embodiment, the value of the potential of the positive power supply terminal of the first operational amplifier 56 is determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier) in the state where: 1. there is an error of +10% in the electric resistance value $R_{HTR}$ of the load 21, 2. the temperature of the load 21 is within the operating temperature range, and 3. the potential "$V_+$" of the second connection node is equal to or higher than the potential "$V_-$" of the first connection node or the state where: 1. there is an error of −10% in the electric resistance value $R_{HTR}$ of the load 21, 2. the temperature of the load 21 is within the operating temperature range, and 3. the potential "$V_+$" of the second connection node is equal to or higher than the potential "$V_-$" of the first connection node.

As described above, by determining the values of the potentials of the power supply terminals of the first operational amplifier 56 in consideration of the manufacturing error of the load 21, the differential input value of the first operational amplifier 56 is between the potential of the negative power supply terminal and the potential of the positive power supply terminal in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved.

(Second Modification of Third Embodiment of Electric Circuit)

Figure 30:
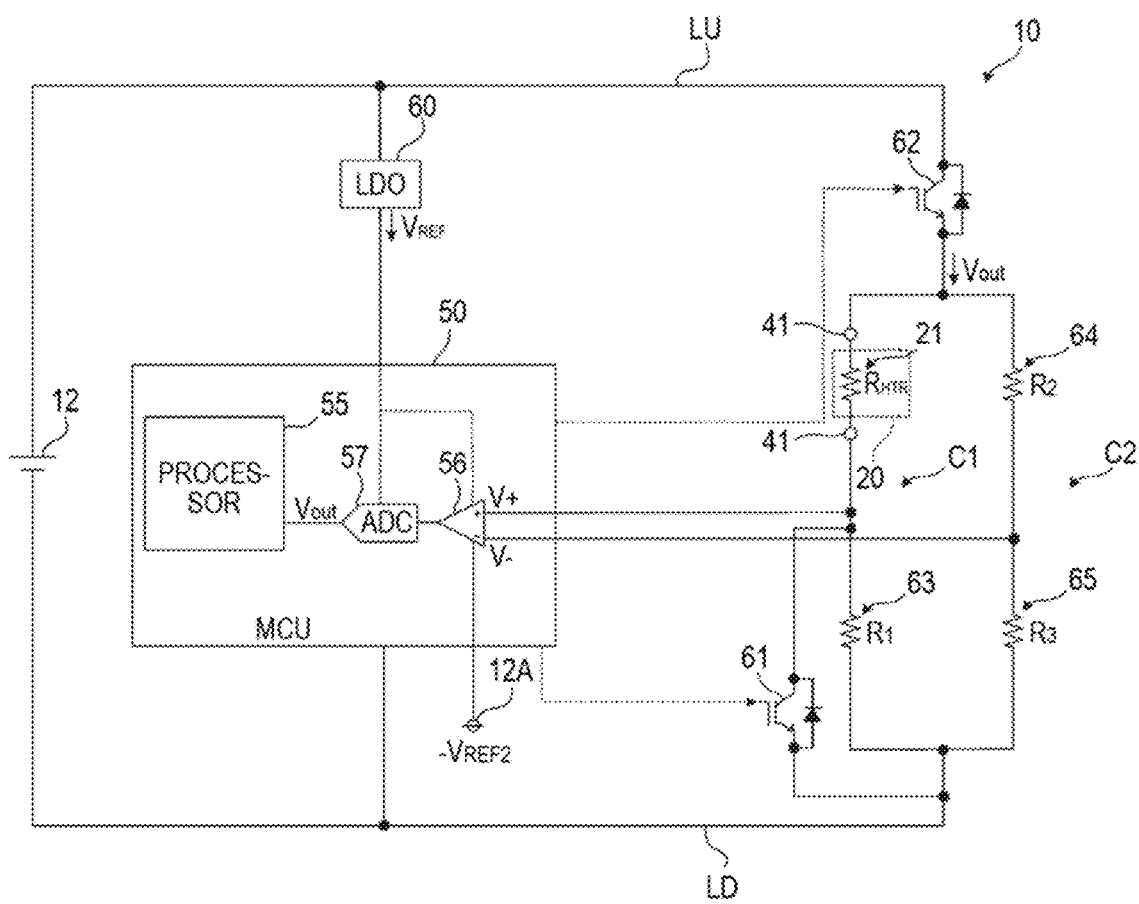
FIG. 30 is a schematic view showing a second modification of the circuit configuration of the power supply unit 10 of the third embodiment shown in FIG. 25.

FIG. 30 is a schematic view showing a second modification of the circuit configuration of the power supply unit 10 of the third embodiment shown in FIG. 25. The power supply unit 10 shown in FIG. 30 is the same as the circuit configuration of FIG. 25 except that the positions of the first element 63 and the load 21 are reversed in the first series circuit C1 while the position of the switch 61 is changed.

The switch 61 is connected between the first connection node and the main negative bus LD. In the power supply unit 10 shown in FIG. 30, the load 21 is heated when the switch 61 and the switch 62 are both turned on. The temperature of the load 21 is detected when the switch 61 is turned off while the switch 62 is turned on.

Figure 31:
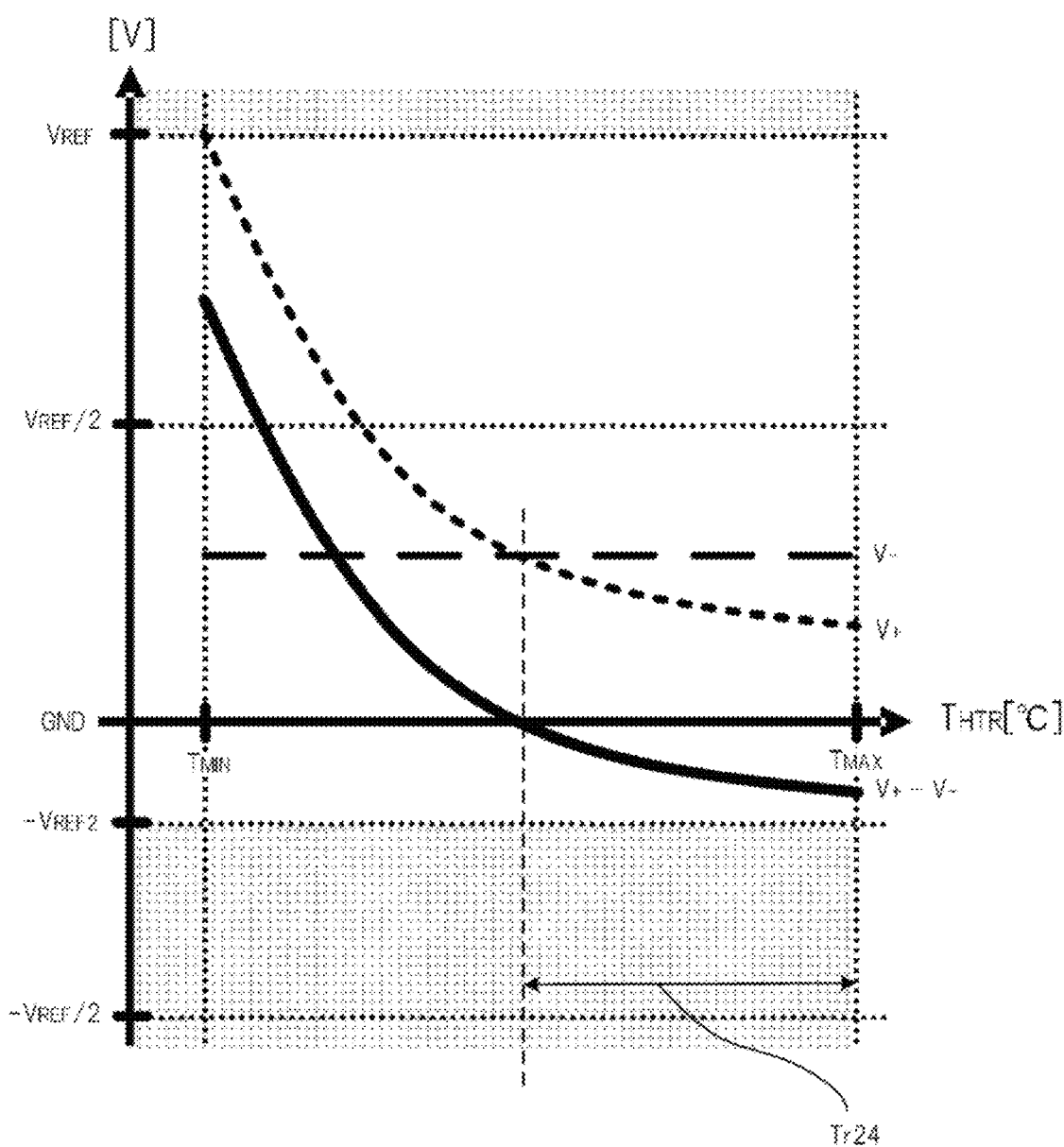
FIG. 31 is a graph showing an example of the differential input value of the first operational amplifier 56 in the power supply unit 10 shown in FIG. 30.

FIG. 31 is a graph showing an example of the differential input value of the first operational amplifier 56 in the power supply unit 10 shown in FIG. 30. In FIG. 31, a graph denoted by "$V_+$" represents the potential of the first connection node between the first element 63 and the load 21. In FIG. 31, a graph denoted by "$V_-$" represents the potential of the second connection node between the second element 64 and the third element 65. In FIG. 31, a graph denoted by "$V_+ - V_-$" represents the differential input value of the first operational amplifier 56.

As an example, in the power supply unit 10 shown in FIG. 30, the electric resistance value $R_{HTR}$ of the load 21 is designed in such a manner that the potential "$V_+$" of the first connection node and the potential "$V_-$" of the second connection node are equal in the state where the temperature of the load 21 is equal to the upper limit temperature $T_{MAX}$. FIG. 31 shows an example in which there is an error of −10% in the electric resistance value $R_{HTR}$ of the load 21.

Since there is an error of −10% in the electric resistance value $R_{HTR}$ of the load 21, in the example shown in FIG. 31, the potential "$V_+$" of the first connection node is less than the potential "$V_-$" of the second connection node in a temperature range Tr24 in the operating temperature range. In order to prevent the lower limit clip, in the temperature range Tr24, the potential of the negative power supply 12A may be determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier). In the example of FIG. 31, in a range excluding the temperature range Tr24 in the operating temperature range, the potential of the positive power supply terminal of the first operational amplifier 56 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

When there is an error of +10% in the electric resistance value $R_{HTR}$ of the load 21 as compared with the design value, the potential "$V_+$" of the first connection node is not less than the potential "$V_-$" of the second connection node in the operating temperature range.

Therefore, in the state where the temperature of the load 21 is within the operating temperature range while the potential "$V_+$" of the first connection node is equal to or higher than the potential "$V_-$" of the second connection node, the potential of the positive power supply terminal of the first operational amplifier 56 may be determined in such a manner that the differential input value of the first operational amplifier 56 is smaller than the potential of the positive power supply terminal.

In this way, in the power supply unit 10 of the second modification of the third embodiment, the value of the potential of the negative power supply 12A is determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier) in the state where: 1. there is an error of −10% in the electric resistance value $R_{HTR}$ of the load 21, 2. the temperature of the load 21 is within the operating temperature range, and 3. the potential "$V_+$" of the first connection node is less than the potential "$V_-$" of the second connection node. In the power supply unit 10 of the second modification of the third embodiment, the value of the potential of the positive power supply terminal of the first operational amplifier 56 is determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier) in the state where: 1. there is an error of −10% in the electric resistance value $R_{HTR}$ of the load 21, 2. the temperature of the load 21 is within the operating temperature range, and 3. the potential "$V_+$" of the first connection node is equal to or higher than the potential "$V_-$" of the second connection node or the state where: 1. there is an error of +10% in the electric resistance value $R_{HTR}$ of the load 21, 2. the temperature of the load 21 is within the operating temperature range, and 3. the potential "$V_+$" of the first connection node is equal to or higher than the potential "$V_-$" of the second connection node.

As described above, by determining the values of the potentials of the power supply terminals of the first operational amplifier 56 in consideration of the manufacturing error of the load 21, the differential input value of the first operational amplifier 56 is between the potential of the negative power supply terminal and the potential of the positive power supply terminal in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved.

(Third Modification of Third Embodiment of Electric Circuit)

Figure 32:
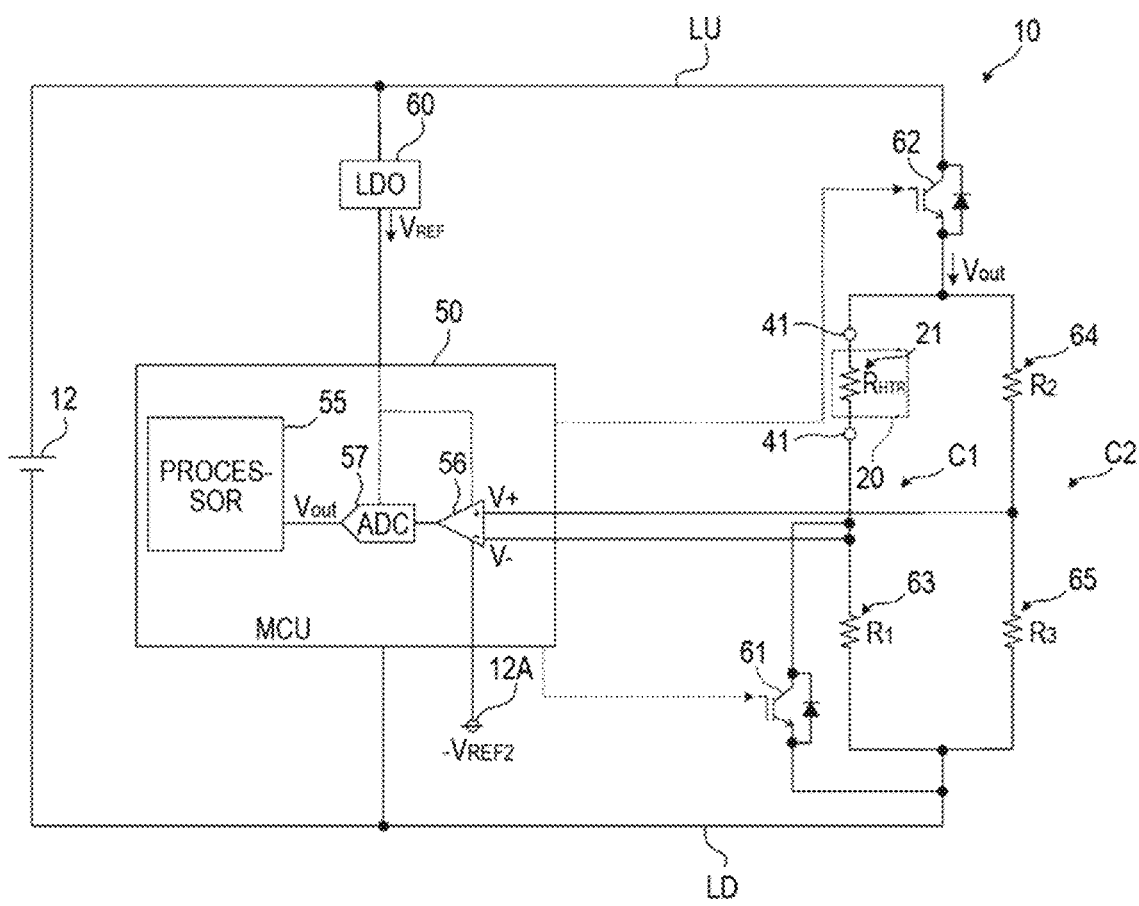
FIG. 32 is a schematic view showing a third modification of the circuit configuration of the power supply unit of the third embodiment shown in FIG. 25.

FIG. 32 is a schematic view showing a third modification of the circuit configuration of the power supply unit of the second embodiment shown in FIG. 25. The power supply unit 10 shown in FIG. 32 is the same as the circuit configuration of FIG. 30 except that the connection relationship between the first operational amplifier 56 and the bridge circuit is changed. In the power supply unit 10 shown in FIG. 32, the inversion input terminal of the first operational amplifier 56 is connected to the first connection node between the first element 63 and the load 21. The non-inversion input terminal of the first operational amplifier 56 is connected to the second connection node between the second element 64 and the third element 65.

Figure 33:
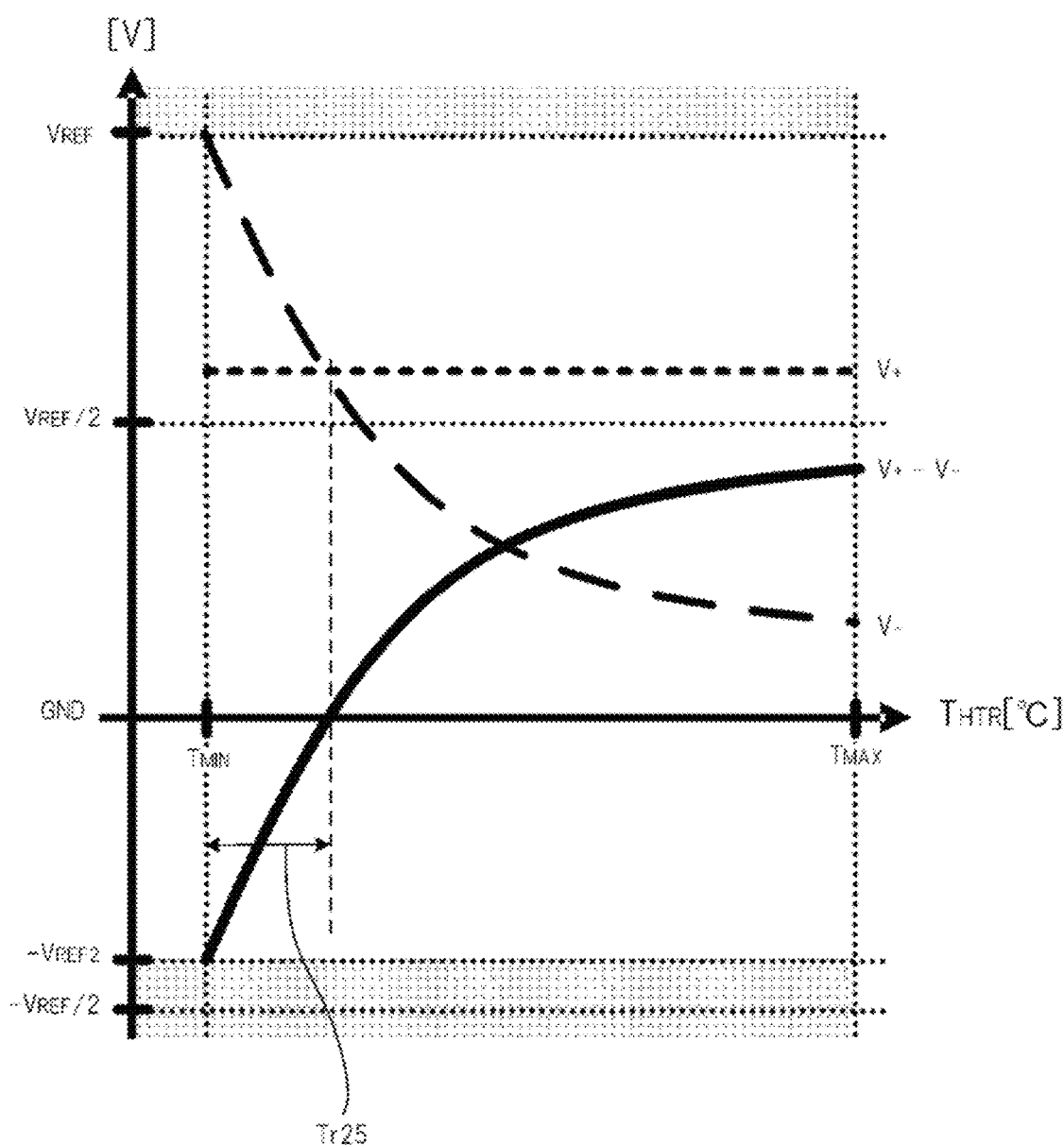
FIG. 33 is a graph showing an example of the differential input value of the first operational amplifier 56 in the power supply unit 10 shown in FIG. 32.

FIG. 33 is a graph showing an example of the differential input value of the first operational amplifier 56 in the power supply unit 10 shown in FIG. 32. In FIG. 33, a graph denoted by "$V_+$" represents the potential of the second connection node between the second element 64 and the third element 65. In FIG. 33, a graph denoted by "V_" represents the potential of the first connection node between the first element 63 and the load 21. In FIG. 33, a graph denoted by "V_+–V_" represents the differential input value of the first operational amplifier 56.

As an example, in the power supply unit 10 shown in FIG. 32, the electric resistance value $R_{HTR}$ of the load 21 is designed in such a manner that the potential "V_+" of the second connection node and the potential "V_" of the first connection node are equal in the state where the temperature of the load 21 is equal to the lower limit temperature $T_{MIN}$. FIG. 33 shows an example in which there is an error of +10% in the electric resistance value $R_{HTR}$ of the load 21.

Since there is an error of +10% in the electric resistance value $R_{HTR}$ of the load 21, in the example shown in FIG. 33, the potential "V_+" of the second connection node is less than the potential "V_" of the first connection node in a temperature range Tr25 in the operating temperature range. In order to prevent the lower limit clip, in the temperature range Tr25, the potential of the negative power supply 12A may be determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier). In the example of FIG. 33, in a range excluding the temperature range Tr25 in the operating temperature range, the potential of the positive power supply terminal of the first operational amplifier 56 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

When there is an error of −10% in the electric resistance value $R_{HTR}$ of the load 21 as compared with the design value, the potential "V_+" of the second connection node is not less than the potential "V_" of the first connection node in the operating temperature range. Therefore, in the state where the temperature of the load 21 is within the operating temperature range while the potential "V_+" of the second connection node is equal to or higher than the potential "V_" of the first connection node, the potential of the positive power supply terminal of the first operational amplifier 56 may be determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier).

In this way, in the power supply unit 10 of the third modification of the third embodiment, the value of the potential of the negative power supply 12A is determined in such a manner that the differential input value of the first operational amplifier 56 is larger than the potential of the negative power supply terminal (the minimum value that can be acquired by the first operational amplifier 56 in the state where the operational amplifier 56 is not the input-output rail-to-rail type operational amplifier) in the state where: 1. there is an error of +10% in the electric resistance value $R_{HTR}$ of the load 21, 2. the temperature of the load 21 is within the operating temperature range, and 3. the potential "V_+" of the second connection node is less than the potential "V_" of the first connection node. In the power supply unit 10 of the third modification of the third embodiment, the value of the potential of the positive power supply terminal of the first operational amplifier 56 is determined in such a manner that the differential input value of the first operational amplifier 56 is smaller than the potential of the positive power supply terminal (the maximum value that can be acquired by the first operational amplifier 56 in the state where the operational amplifier 56 is not the input-output rail-to-rail type operational amplifier) in the state where: 1. there is an error of +10% in the electric resistance value $R_{HTR}$ of the load 21, 2. the temperature of the load 21 is within the operating temperature range, and 3. the potential "V_+" of the second connection node is equal to or higher than the potential "V_" of the first connection node or the state where: 1. there is an error of −10% in the electric resistance value $R_{HTR}$ of the load 21, 2. the temperature of the load 21 is within the operating temperature range, and 3. the potential "V_+" of the second connection node is equal to or higher than the potential "V_" of the first connection node.

As described above, by determining the values of the potentials of the power supply terminals of the first operational amplifier 56 in consideration of the manufacturing error of the load 21, the differential input value of the first operational amplifier 56 is between the potential of the negative power supply terminal and the potential of the positive power supply terminal in the operating temperature range when there is a manufacturing error in the load 21. Therefore, the occurrence of the lower limit clip and the upper limit clip can be prevented in the first operational amplifier 56, and the detection accuracy of the temperature of the load 21 can be improved. As described above, when the first operational amplifier 56 is not the input-output rail-to-rail type operational amplifier, the potential of the negative power supply 12A may be determined in such a manner that the differential input value of the first operational amplifier 56 is between the maximum value and the minimum value that can be acquired by the first operational amplifier 56.

Although the first cartridge 20 including the load 21 is detachably attached to the power supply unit 10 in the above-described embodiments, the first cartridge 20 including the load 21 may also be integrated with the power supply unit 10.

At least the following matters are described in the present specification. Although corresponding constituent elements or the like in the above embodiments are shown in parentheses, the present invention is not limited thereto.

(1)

A power supply unit (power supply unit 10) for an aerosol inhaler (aerosol inhaler 1). The aerosol inhaler includes a power supply (power supply 12) configured to discharge electricity to a load (load 21) which is configured to heat an aerosol generation source and has a correlation between temperature and electric resistance values. The power supply unit for the aerosol inhaler includes:

a first element (first element 63) connected in series to the load and having a first electric resistance value;

a second series circuit (second series circuit C2), which includes a second element (second element 64) having a second electric resistance value, and a third element (third element 65) connected in series to the second element and having a third electric resistance value, the second series circuit being connected in parallel with a first series circuit (first series circuit C1) including the load and the first element;

a first operational amplifier (first operational amplifier 56), which includes a non-inversion input terminal connected to one of a first connection node between the load and the first element and a second connection node between the second element and the third element, and an inversion input terminal connected to the other of the first connection node and the second connection node; and a potential adjustment circuit (second operational amplifier 58, rail splitter circuit 59, negative power supply 12A) connected to the first operational amplifier and configured to prevent a differential input value of the first operational amplifier from being equal to a potential of a negative power supply terminal of the first operational amplifier or a minimum value acquirable by the first operational amplifier, in a state where a first potential of the first connection node or the second connection node which is connected to the non-inversion input terminal is less than a second potential of the first connection node or the second connection node which is connected to the inversion input terminal.

According to (1), even when the first potential is less than the second potential, the differential input value of the first operational amplifier is prevented from being equal to the potential of the negative power supply terminal of the first operational amplifier or the minimum value that can be acquired by the first operational amplifier. Therefore, the temperature of the load can be detected with high accuracy based on an output signal of the first operational amplifier.

(2)

The power supply unit for the aerosol inhaler according to (1), in which the potential adjustment circuit includes a second operational amplifier (second operational amplifier 58), and the second operational amplifier includes: a non-inversion input terminal which is connected to the first connection node or the second connection node which is connected to the inversion input terminal; an inversion input terminal to which a positive predetermined potential is input; and an output terminal connected to the inversion input terminal of the first operational amplifier.

According to (2), the differential input value of the first operational amplifier can be raised by the predetermined potential due to the second operational amplifier. As a result, by setting the predetermined potential to an appropriate value, the differential input value of the first operational amplifier can be prevented from being equal to the potential of the negative power supply terminal of the first operational amplifier or the minimum value that can be acquired by the first operational amplifier, and thus the temperature of the load can be detected with high accuracy.

(3)

The power supply unit for the aerosol inhaler according to (2), in which a value of the predetermined potential is equal to a value of a potential input to a positive power supply terminal of the first operational amplifier, or a value of a voltage applied to the first series circuit and the second series circuit.

According to (3), since a potential used for other purposes in the circuit can be used directly, the differential input value of the first operational amplifier can be raised by the predetermined potential without requiring any complicated circuit.

(4)

The power supply unit for the aerosol inhaler according to (2), in which the predetermined potential is obtained by dividing a potential input to a positive power supply terminal of the first operational amplifier, or a voltage applied to the first series circuit and the second series circuit.

According to (4), since the predetermined potential is generated by dividing or stepping down, it is easy to set the predetermined potential to a desired value. As a result, an appropriate predetermined potential for preventing the differential input value of the first operational amplifier from being equal to the potential of the negative power supply terminal of the first operational amplifier or the minimum value that can be acquired by the first operational amplifier can be provided to the second operational amplifier.

(5)

The power supply unit for the aerosol inhaler according to (2), in which the predetermined potential has a value at which the differential input value of the first operational amplifier is larger than the potential of the negative power supply terminal of the first operational amplifier or the minimum value acquirable by the first operational amplifier in a state where the temperature of the load is equal to or lower than an upper limit temperature ($T_{MAX}$) while the first potential is less than the second potential, or a state where the temperature of the load is equal to or higher than a lower limit temperature ($T_{MIN}$) while the first potential is less than the second potential, the upper limit temperature is an upper limit value of a temperature range in which discharge to the load is performed, and the lower limit temperature is a lower limit value of the temperature range.

According to (5), since the differential input value of the first operational amplifier is larger than the potential of the negative power supply terminal or the minimum value that can be acquired by the first operational amplifier in the temperature range where the discharge to the load is performed, the temperature of the load can be detected with high accuracy within an operating temperature range of the load.

(6)

The power supply unit for the aerosol inhaler according to (2), in which the predetermined potential has a value at which the differential input value of the first operational amplifier is larger than the potential of the negative power supply terminal of the first operational amplifier or the minimum value acquirable by the first operational amplifier, in a state where:

the electric resistance value of the load has an error of −10% as compared with an assumed electric resistance value of the load assumed in a case where the temperature of the load is equal to a lower limit temperature ($T_{MIN}$) or an upper limit temperature ($T_{MAX}$) while the first potential and the second potential are equal, the electric resistance value of the load has an error of +10% as compared with the assumed electric resistance value of the load assumed in a case where the temperature of the load is equal to or higher than the lower limit temperature or equal to or lower than the upper limit temperature while the first potential is lower than the second potential or in the case where the temperature of the load is equal to the upper limit temperature or the lower limit temperature while the first potential and the second potential are equal, and the temperature of the load is equal to or lower than the upper limit temperature or equal to or higher than the lower limit temperature, and the first potential is less than the second potential, the upper limit temperature is an upper limit value of a temperature range in which discharge to the load, and the lower limit temperature is a lower limit value of the temperature range.

According to (6), since the differential input value of the first operational amplifier is larger than the potential of the negative power supply terminal or the minimum value that can be acquired by the first operational amplifier in the temperature range where the discharge to the load is performed, the temperature of the load can be detected with high accuracy within the operating temperature range of the load even when there is an error in the electric resistance value of the load.

(7)

The power supply unit for the aerosol inhaler according to (5) or (6), in which the predetermined potential has a value at which the differential input value of the first operational amplifier is equal to the potential of the negative power supply terminal of the first operational amplifier or the minimum value acquirable by the first operational amplifier, in a state where the temperature of the load exceeds the upper limit temperature while the first potential is less than the second potential, or a state where the temperature of the load is less than the lower limit temperature while the first potential is less than the second potential.

According to (7), the differential input value of the first operational amplifier is allowed to be equal to the potential of the negative power supply terminal or the minimum value that can be acquired by the first operational amplifier outside the temperature range where the discharge to the load is performed, so that it is not necessary to generate an excessive predetermined potential. As a result, a size of the circuit can be reduced.

(8)

The power supply unit for the aerosol inhaler according to (5) or (6), in which the predetermined potential has a value at which the differential input value of the first operational amplifier is lower than a potential of a positive power supply terminal of the first operational amplifier or a maximum value acquirable by the first operational amplifier, in a state where the temperature of the load is equal to or less than the upper limit temperature while the first potential is less than the second potential, or a state where the temperature of the load is equal to or higher than the lower limit temperature while the first potential is less than the second potential.

According to (8), since the differential input value of the first operational amplifier is smaller than the potential of the positive power supply terminal or the maximum value that can be acquired by the first operational amplifier in the temperature range where the discharge to the load is performed, the temperature of the load can be detected with high accuracy within the operating temperature range of the load.

(9)

The power supply unit for the aerosol inhaler according to (1), in which the potential adjustment circuit includes a rail splitter circuit (rail splitter circuit 59) configured to generate a negative potential from an input voltage and a positive potential having a same absolute value as the negative potential, the positive potential is input to a positive power supply terminal of the first operational amplifier, and the negative potential is input to the negative power supply terminal of the first operational amplifier.

According to (9), due to the rail splitter circuit, the differential input value of the first operational amplifier hardly approaches the potential of the negative power supply terminal or the minimum value that can be acquired by the first operational amplifier. Therefore, the differential input value of the first operational amplifier can be effectively prevented from being lower than the potential of the negative power supply terminal of the first operational amplifier or the minimum value that can be acquired by the first operational amplifier, and thus the temperature of the load can be detected with high accuracy.

(10)

The power supply unit for the aerosol inhaler according to (9), in which at least one of a value of the input voltage and an electric resistance value of a resistor included in the rail splitter circuit has a value at which the differential input value of the first operational amplifier is larger than the negative potential in a state where the temperature of the load is equal to or lower than an upper limit temperature ($T_{MAX}$) while the first potential is less than the second potential, or a state where the temperature of the load is equal to or higher than a lower limit temperature ($T_{MIN}$) while the first potential is less than the second potential, the upper limit temperature is an upper limit value of a temperature range in which discharge to the load, and the lower limit temperature is a lower limit value of the temperature range.

According to (10), since the differential input value of the first operational amplifier is larger than the potential of the negative power supply terminal or the minimum value that can be acquired by the first operational amplifier in the temperature range where the discharge to the load is performed, the temperature of the load can be detected with high accuracy within the operating temperature range of the load.

(11)

The power supply unit for the aerosol inhaler according to (9) or (10), in which at least one of the value of the input voltage and the electric resistance value of the resistor included in the rail splitter circuit has a value at which the differential input value of the first operational amplifier is smaller than the positive potential in a state where the temperature of the load is equal to or lower than an upper limit temperature ($T_{MAX}$) or a state where the temperature of the load is equal to or higher than a lower limit temperature ($T_{MIN}$), the upper limit temperature is an upper limit value of a temperature range in which discharge to the load, and the lower limit temperature is a lower limit value of the temperature range.

According to (11), since the differential input value of the first operational amplifier is lower than the potential of the positive power supply terminal or the maximum value that can be acquired by the first operational amplifier in the temperature range where the discharge to the load is performed, the temperature of the load can be detected with high accuracy within the operating temperature range of the load.

(12)

The power supply unit for the aerosol inhaler according to (1), in which the potential adjustment circuit includes a negative power supply (negative power supply 12A) configured to generate a negative potential, and the negative power supply is connected to the negative power supply terminal of the first operational amplifier.

According to (12), due to the negative power supply, the differential input value of the first operational amplifier hardly approaches the potential of the negative power supply terminal or the minimum value that can be acquired by the first operational amplifier. Therefore, the differential input value of the first operational amplifier can be effectively prevented from being lower than the potential of the negative power supply terminal of the first operational amplifier or the minimum value that can be acquired by the first operational amplifier, and thus the temperature of the load can be detected with high accuracy.

(13)

The power supply unit for the aerosol inhaler according to (12), in which the negative potential has a value at which the differential input value of the first operational amplifier is larger than the negative potential in a state where the temperature of the load is equal to or lower than an upper limit temperature ($T_{MAX}$) while the first potential is less than the second potential, or a state where the temperature of the load is equal to or higher than a lower limit temperature ($T_{MIN}$) while the first potential is less than the second potential, the upper limit temperature is an upper limit value of a temperature range in which discharge to the load, and the lower limit temperature is a lower limit value of the temperature range.

According to (13), since the differential input value of the first operational amplifier is larger than the potential of the negative power supply terminal or the minimum value that can be acquired by the first operational amplifier in the temperature range where the discharge to the load is performed, the temperature of the load can be detected with high accuracy within the operating temperature range of the load.

(14)

A power supply unit (power supply unit 10) for an aerosol inhaler (aerosol inhaler 1). The aerosol inhaler includes a power supply (power supply 12) configured to discharge electricity to a load (load 21) which is configured to heat an aerosol generation source and has a correlation between temperature and electric resistance values. The power supply unit for the aerosol inhaler includes:

a first element (first element 63) connected in series to the load and having a first electric resistance value;

a second series circuit (second series circuit C2), which includes a second element (second element 64) having a second electric resistance value, and a third element (third element 65) connected in series to the second element and having a third electric resistance value, the second series circuit being connected in parallel with a first series circuit (first series circuit C1) including the load and the first element;

a first operational amplifier (first operational amplifier 56), which includes a non-inversion input terminal connected to one of a first connection node between the load and the first element and a second connection node between the second element and the third element, and an inversion input terminal connected to the other of the first connection node and the second connection node; and a second operational amplifier (second operational amplifier 58), which includes: a non-inversion input terminal which is connected to the first connection node or the second connection node connected indirectly to the inversion input terminal; an inversion input terminal where a positive predetermined potential (predetermined potential $V_{PSEUDO}$) is input; and an output terminal connected to the inversion input terminal of the first operational amplifier.

According to (14), the differential input value of the first operational amplifier can be raised by the predetermined potential due to the second operational amplifier. As a result, even when the first potential is less than the second potential, the differential input value of the first operational amplifier is prevented from being lower than the potential of the negative power supply terminal of the first operational amplifier or the minimum value that can be acquired by the first operational amplifier. Therefore, the temperature of the load can be detected with high accuracy based on the output signal of the first operational amplifier.

The invention claimed is:

1. A power supply unit for an aerosol inhaler, the aerosol inhaler including a power supply configured to discharge electricity to a load which is configured to heat an aerosol generation source and has a correlation between temperature and electric resistance values, the power supply unit comprising:

a first element connected in series to the load and having a first electric resistance value;

a second series circuit which includes a second element having a second electric resistance value, and a third element connected in series to the second element and having a third electric resistance value, the second series circuit being connected in parallel with a first series circuit including the load and the first element;

a first operational amplifier which includes a non-inversion input terminal connected to one of a first connection node between the load and the first element and a second connection node between the second element and the third element, and an inversion input terminal connected to the other of the first connection node and the second connection node; and a potential adjustment circuit connected to the first operational amplifier and configured to prevent a differential input value of the first operational amplifier from being equal to a potential of a negative power supply terminal of the first operational amplifier or a minimum value acquirable by the first operational amplifier, in a state where a first potential of the first connection node or the second connection node which is connected to the non-inversion input terminal is less than a second potential of the first connection node or the second connection node which is connected to the inversion input terminal.

2. The power supply unit for the aerosol inhaler according to claim 1, wherein the potential adjustment circuit includes a second operational amplifier, and the second operational amplifier includes: a non-inversion input terminal which is connected to the first connection node or the second connection node which is connected to the inversion input terminal; an inversion input terminal to which a positive predetermined potential is input; and an output terminal connected to the inversion input terminal of the first operational amplifier.

3. The power supply unit for the aerosol inhaler according to claim 2, wherein a value of the predetermined potential is equal to a value of a potential input to a positive power supply terminal of the first operational amplifier, or a value of a voltage applied to the first series circuit and the second series circuit.

4. The power supply unit for the aerosol inhaler according to claim 2, wherein the predetermined potential is obtained by dividing or stepping down a potential input to a positive power supply terminal of the first operational amplifier, or a voltage applied to the first series circuit and the second series circuit.

5. The power supply unit for the aerosol inhaler according to claim 2, wherein
the predetermined potential has a value at which the differential input value of the first operational amplifier is larger than the potential of the negative power supply terminal of the first operational amplifier or the minimum value acquirable by the first operational amplifier, in a state where the temperature of the load is equal to or lower than an upper limit temperature while the first potential is less than the second potential, or a state where the temperature of the load is equal to or higher than a lower limit temperature while the first potential is less than the second potential,
the upper limit temperature is an upper limit value of a temperature range in which discharge to the load is performed, and
the lower limit temperature is a lower limit value of the temperature range.

6. The power supply unit for the aerosol inhaler according to claim 2, wherein
the predetermined potential has a value at which the differential input value of the first operational amplifier is larger than the potential of the negative power supply terminal of the first operational amplifier or the minimum value acquirable by the first operational amplifier, in a state where:
the electric resistance value of the load has an error of −10% as compared with an assumed electric resistance value of the load assumed in a case where the temperature of the load is equal to a lower limit temperature or an upper limit temperature while the first potential and the second potential are equal,
the electric resistance value of the load has an error of +10% as compared with the assumed electric resistance value of the load assumed in a case where the temperature of the load is equal to or higher than the lower limit temperature or equal to or lower than the upper limit temperature while the first potential is lower than the second potential or in the case where the temperature of the load is equal to the upper limit temperature or the lower limit temperature while the first potential and the second potential are equal, and
the temperature of the load is equal to or lower than the upper limit temperature or equal to or higher than the lower limit temperature, and the first potential is less than the second potential,
the upper limit temperature is an upper limit value of a temperature range in which discharge to the load, and
the lower limit temperature is a lower limit value of the temperature range.

7. The power supply unit for the aerosol inhaler according to claim 5, wherein
the predetermined potential has a value at which the differential input value of the first operational amplifier is equal to the potential of the negative power supply terminal of the first operational amplifier or the minimum value acquirable by the first operational amplifier, in a state where the temperature of the load exceeds the upper limit temperature while the first potential is less than the second potential, or a state where the temperature of the load is less than the lower limit temperature while the first potential is less than the second potential.

8. The power supply unit for the aerosol inhaler according to claim 5, wherein
the predetermined potential has a value at which the differential input value of the first operational amplifier is lower than a potential of a positive power supply terminal of the first operational amplifier or a maximum value acquirable by the first operational amplifier, in a state where the temperature of the load is equal to or less than the upper limit temperature while the first potential is less than the second potential, or a state where the temperature of the load is equal to or higher than the lower limit temperature while the first potential is less than the second potential.

9. The power supply unit for the aerosol inhaler according to claim 1, wherein
the potential adjustment circuit includes a rail splitter circuit configured to generate a negative potential from an input voltage and a positive potential having a same absolute value as the negative potential,
the positive potential is input to a positive power supply terminal of the first operational amplifier, and
the negative potential is input to the negative power supply terminal of the first operational amplifier.

10. The power supply unit for the aerosol inhaler according to claim 9, wherein
at least one of a value of the input voltage and an electric resistance value of a resistor included in the rail splitter circuit has a value at which the differential input value of the first operational amplifier is larger than the negative potential in a state where the temperature of the load is equal to or lower than an upper limit temperature while the first potential is less than the second potential, or a state where the temperature of the load is equal to or higher than a lower limit temperature while the first potential is less than the second potential,
the upper limit temperature is an upper limit value of a temperature range in which discharge to the load is performed, and
the lower limit temperature is a lower limit value of the temperature range.

11. The power supply unit for the aerosol inhaler according to claim 9, wherein
at least one of the value of the input voltage and the electric resistance value of the resistor included in the rail splitter circuit has a value at which the differential input value of the first operational amplifier is smaller than the positive potential in a state where the temperature of the load is equal to or lower than an upper limit temperature or a state where the temperature of the load is equal to or higher than a lower limit temperature,
the upper limit temperature is an upper limit value of a temperature range in which discharge to the load is performed, and
the lower limit temperature is a lower limit value of the temperature range.

12. The power supply unit for the aerosol inhaler according to claim 1, wherein
the potential adjustment circuit includes a negative power supply configured to generate a negative potential, and
the negative power supply is connected to the negative power supply terminal of the first operational amplifier.

13. The power supply unit for the aerosol inhaler according to claim 12, wherein
the negative potential has a value at which the differential input value of the first operational amplifier is larger than the negative potential in a state where the temperature of the load is equal to or lower than an upper limit temperature while the first potential is less than the second potential, or a state where the temperature of the load is equal to or higher than a lower limit temperature while the first potential is less than the second potential, the upper limit temperature is an upper limit value of a temperature range in which discharge to the load is performed, and the lower limit temperature is a lower limit value of the temperature range.

14. A power supply unit for an aerosol inhaler, the aerosol inhaler including a power supply configured to discharge electricity to a load which is configured to heat an aerosol generation source and has a correlation between temperature and electric resistance values, the power supply unit comprising:

a first element connected in series to the load and having a first electric resistance value;

a second series circuit, which includes a second element having a second electric resistance value, and a third element connected in series to the second element and having a third electric resistance value, the second series circuit being connected in parallel with a first series circuit including the load and the first element;

a first operational amplifier, which includes a non-inversion input terminal connected to one of a first connection node between the load and the first element and a second connection node between the second element and the third element, and an inversion input terminal connected indirectly to the other of the first connection node and the second connection node; and a second operational amplifier, which includes: a non-inversion input terminal which is connected to the first connection node or the second connection node connected indirectly to the inversion input terminal; an inversion input terminal where a positive predetermined potential is input; and an output terminal connected to the inversion input terminal of the first operational amplifier.

\* \* \* \* \*